(12) United States Patent
Rosenthal et al.

(10) Patent No.: US 6,277,820 B1
(45) Date of Patent: *Aug. 21, 2001

(54) METHOD OF DOPAMINERGIC AND SEROTONERGIC NEURON FORMATION FROM NEUROPROGENITOR CELLS

(75) Inventors: Arnon Rosenthal, Burlingame; Mary A. Hynes; Weilan Ye, both of San Mateo, all of CA (US)

(73) Assignee: Genentech, Inc., So. San Francisco, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/057,860

(22) Filed: Apr. 9, 1998

(51) Int. Cl.[7] .................................................. A61K 38/18

(52) U.S. Cl. .................................................. 514/12; 514/2

(58) Field of Search .......................................... 514/2, 12

(56) References Cited

U.S. PATENT DOCUMENTS

| | | |
|---|---|---|
| 5,182,111 | 1/1993 | Aebischer et al. . |
| 5,334,640 | 8/1994 | Desai et al. . |
| 5,589,376 | 12/1996 | Anderson et al. . |
| 5,602,309 | 2/1997 | Albers et al. . |
| 5,651,980 | 7/1997 | Lanza et al. . |
| 5,656,481 | 8/1997 | Baetge et al. . |
| 5,672,499 | 9/1997 | Anderson et al. . |
| 5,733,875 | 3/1998 | Martin . |

FOREIGN PATENT DOCUMENTS

| | | |
|---|---|---|
| 2717824 | 9/1995 | (FR) . |
| WO 91/01739 | 2/1991 | (WO) . |
| WO 93/00439 | 1/1993 | (WO) . |
| WO 94/03199 | 2/1994 | (WO) . |
| WO 95/10611 | 4/1995 | (WO) . |
| WO 95/26409 | 10/1995 | (WO) . |
| WO 96/04368 | 2/1996 | (WO) . |
| WO 96/15224 | 5/1996 | (WO) . |
| WO 96/23003 | 8/1996 | (WO) . |
| WO 98/08864 | 3/1998 | (WO) . |

OTHER PUBLICATIONS

Alvarado–Mallart et al., "Pluripotentiality of the 2–day–old avian germinative neuroepithelium" *Developmental Biology* 139(1) :75–88 (May 1990).

Apostolides et al., "Glial cell line–derived neurotrophic factor improves intrastriatal graft survival of stored dopaminergic cells" *Neuroscience* 83(2) :363–32 (Mar. 1998).

Asberg and Martensson, "Serotonin Selective Antidepressant Drugs: Past, Present, Future" *Clinical Neuropharmacology* 16(Suppl. 3) :S32–S44 (1993).

Asberg et al., "Therapeutic effects of serotonin uptake inhibitors in depression" *Journal of Clinical Psychiatry* 47(4 Suppl.) :23–35 (Apr. 1986).

Bally–Cuif and Wassef, "Determination events in the nervous system of the vertebrate embryo" *Current Opinion in Genetics & Development* 5(4) :450–458 (Aug. 1995).

Bally–Cuif et al., "Relationship between Wnt–1 and En–2 expression domains during early development of normal and ectopic met–mesencephalon" *Development* 115(4) :999–1009 (Aug. 1992).

Barinaga, M., "Researchers Broaden the Attack on Parkinson's Disease" *Science* 267:455–456 (Jan. 27, 1995).

Briley and Moret, "Neurobiological Mechanisms Involved in Antidepressant Therapies" *Clinical Neuropharmacology* 16(5) :387–400 (1993).

Brown and Linnoila, "CSF serotonin metabolite (5–HIAA) studies in depression, impulsivity, and violence" *Journal of Clinical Psychiatry* 51(4) Suppl.) :31–41 (Apr. 1990).

Bueno et al., "Spatial and temporal relationships between Shh, Fgf4, and Fgf8 gene expression at diverse signalling centers during mouse development" *Developmental Dynamics* 207 (3):291–299 (Nov. 1996).

Chiang et al., "Cyclopia and defective axial patterning in mice lacking Sonic hedgehog gene function" *Nature* 383(6599):407–413 (Oct. 3, 1996).

(List continued on next page.)

*Primary Examiner*—Gary L. Kunz
*Assistant Examiner*—Stephen Gucker
(74) *Attorney, Agent, or Firm*—David A. Carpenter

(57) ABSTRACT

The present invention relates to neuronal formation and methods of treating diseases characterized by abnormalities in the activity of dopaminergic (DA) and serotonergic (5HT) neurons. In particular, the invention relates to a method of forming serotonergic neurons in vitro by contacting neuroprogenitor cells to an effective amount of native sequence, variants and functional fragments of FGF-4, FGF-8 and Shh. Additionally, disclosed is a method for forming dopaminergic neurons by contacting neuroprogenitor cells to an effective amount of FGF-8 and Shh. Further described are compositions, cell culture compositions and medical devices which contain sufficient amount of FGF-8, Shh or FGF-8, Shh and FGF-4 to stimulate differentiation into dopaminergic or serotonergic neurons, respectively. Further described are methods of using serotoneurgic neurons to treat disorders relating to food intake, hormone secretion, stress response, pain and immune function, sexual activity, cardiovascular function and temperature regulation, in particular, depression, proclivity to suicide, violent aggressive behavior, obsessive-compulsive behavior and anorexia/bulimia and schizophrenia. Further described are methods of using dopaminergic neurons to treat disorders relating postural reflexes, movement and reward-associated behaviors, specifically, Parkinson's disease, schizophrenia and drug addiction. Further described is the coadministration of a neuronal survival factor, for example, NGF, CNTF, BDNF, NT-3, NT-4, aFGF, IL-1β, TNFα, IGF-1, IGF-2, TGF-β, TGF-β1 or skeletal muscle extract.

3 Claims, 18 Drawing Sheets

(8 of 18 Drawing Sheet(s) Filed in Color)

OTHER PUBLICATIONS ollier et al., "Cryopreservation of fetal rat and non–human primate mesencephalic neurons: viability in culture and neural transplantation" *Progress in Brain Research* 78:631–636 (1988).

Collier et al., "Intracerebral grafting and culture of cryopreserved primate dopamine neurons" *Brain Research* 436 (2):363–366 (Dec. 15, 1987).

Cox and Hemmati–Brivanlou, "Caudalization of neural fate by tissue recombination and bFGF" *Development* 121 (12):4349–4358 (Dec. 1987).

Crossley et al., "Midbrain development induced by FGF8 in the chick embryo" *Nature* 380 (6569):66–68 (Mar. 7, 1996).

Dale et al., "Cooperation of BMP7 and SHH in the induction of forebrain ventral midline cells by prechordal mesoderm" *Cell* 90 (2):257–259 (Jul. 25, 1997).

Dunnett et al., "Intracerebral grafting of neuronal cell susupensions. V. behavioural recovery in rats with bilateral 6–OHDA lesions following implantation of nigral cell suspensions" *Acta Physiologica Scandinavica* 522(Suppl.):39–47 (1983).

Echelard et al., "Sonic hedgehog, a member of a family of putative signaling molecules, is implicated in the regulation of CNS polarity" *Cell* 75:1417–1430 (1993).

Eichelman, B.S., "Neurochemical and psychopharmacologic aspects of aggressive behavior" *Annual Review of Medicine* 41:149–158 (1990).

Ericson et al., "two critical periods of Sonic Hedgehog signaling required for the specification of motor neuron identity" *Cell* 87(4):661–673 (Nov. 15, 1996).

Ferder et al., "Effects of enalapril on renal parameters in patients with primary glomerulophathies associated with chronic renal failure" *Drugs* 39(Suppl. 2) :40–48 (1990).

Foley et al., "The prechordal region lacks neural inducing ability, but can confer anterior character to more posterior neuroepithelium" *Development* 124(15):2983–2996 (Aug. 1997).

Fuller, R., "Mechanisms and Functions of Serotonin Neuronal Systems. Opportunities for Neuropeptide Interactions" *Neuropeptides : basic and clinical advances* (Annals of the New York Academy of Sciences series), New York:New York Academy of Sciences vol. 780:176–184 (1996).

Fuller, R., "Pharmacologic Modification of Serotonergic Function: Drugs for the Study and Treatment of Psychiatric and Other Disorders" *J. Clin. Psychiatry* 47(4 Suppl.):4–8 (Apr. 1986).

Fuller, R.W., "Serotonin uptake inhibitors: uses in clinical therapy and in laboratory research" *Progress in Drug Research* 45:167–204 (1995).

Galler et al., "Current trends in the pharmacologic and surgical treatment of Parkinson's disease" *Journal of the American Osteopathic Association* 96(4):228–232 (Apr. 1996).

Gardner and Barald, "The cellular environment controls the expression of engrailed–like protein in the cranial neuroepithelium of quail–chick chimeric embryos" *Development* 113(3):1037–1048 (Nov. 1991).

Granholm et al., "Glial cell line–derived neurotrophic factor improves survival of ventral mesencephalic grafts to the 6–hydroxydopamine lesioned striatum" *Experimental Brain Research* 116(1):20–39 (Aug. 1997).

Grapin–Botton et al., "Hox gene induction in the neural tube depends on three parameters: competence, signal supply and paralogue group" *Development* 124(4):849–859 (Feb. 1997).

Haque et al., "The neurotrophin NT4/5, but not NT3, enhances the efficacy of nigral grafts in a rat model of Parkinson's disease" *Brain Research* 712(1):45–52 (Mar. 11, 1996).

Harland and Gerhart, "Formation and function of Spemann's organizer" *Annual Review of Cell & Developmental Biology* 13:611–667 (1997).

Heikinheimo et al., "Fgf–8 expression in the post–gastrulation mouse suggests role in the development of the face, limbs and central nervous system" *Mechanisms of Development* 48(2):129–138 (Nov. 1994).

Henderson et al., "Neurotrophic factors in development and plasticity of spinal neurons" *Restorative Neurology and Neuroscience* 5:15–28 (1993).

Henry et al., "Electron microscopic study following GDNF injection into *substantia nigra* reveals sprouting and synaptogenesis within the striatum" *Society for Neuroscience Abstracts* (Abstract #275.4) 19:652 (1993).

Hofer and Barde, "Brain–derived neurotrophic factor prevents neuronal death in vivo" *Nature* 331(6153):261–2626 (Jan. 21, 1988).

Hornykiewicz, O., "Neurochemical Pathology and the Etiology of Parkinson's Disease: Basic Facts and Hypothetical Possibilities" *Mt. Sinai J. Med.* 55:11–20 (1988).

Houart et al., "A small population of anterior cells patterns the forebrain during zebrafish gastrulation" *Nature* 391(6669):788–792 (Feb. 19, 1998).

Hynes et al., "Control of neuronal diversity by the floor plate:contact–mediated induction of midbrain dopaminergic neurons" *Cell* 80:95–101 (1995).

Hynes et al., "Induction of Midbrain Dopaminergic Neurons by Sonic Hedgehog" *Neuron* 15:35–44 (1995).

Ip et al., "The neurotrophins and CNTF: specificity of action towards PNS and NCS neurons" *Journal de Physiologie* 85(3):123–130 (1991).

Itasaki et al., "Reprogramming Hox expression in the vertebrate hindbrain: influence of paraxial mesoderm and rhombomere transposition" *Neuron* 16(3)487–500 (Mar. 1996).

Jacobs and Gelperin *Serotonin Neurotransmission and Behavior*, Cambridge, MA:The MIT Press (1981).

Joyner, A., "Engrailed, Wnt and Pax genes regulate midbrain—hindbrain development" *Trends in Genetics* 12(1):15–20 (Jan. 1996).

Kengaku and Okamoto, "bFGF as a possible morphogen for the anteroposterior axis of the central nervous system in Xenopus" *Development* 121(9):3121–3130 (Sep. 1995).

Krobert et al., "Astrocytes promote or impair the survival and function of embryonic ventral mesencephalon co–grafts: effects of astrocyte age and expression of recombinant brain–derived neurotrophic factor" *Experimental Neurology* 145:511–523 (Jun. 1997).

Kupsch et al., "Neuronal transplantation and neurotrophic factors in the treatment of Parkinson's disease—update Feb. 1995" *Journal of Neural Transmission* 46(Suppl.):193–207 (1995).

Lamb and Harland, "Fibroblast growth factor is a direct neural inducer, which combined with noggin generates anterior–posterior neural pattern" *Development* 121(11):3627–3636 (Nov. 1995).

Lauder and Bloom, "Ontogeny of monoamine neurons in the *locus coeruleus, Raphe nuclei* and *substantia nigra* of the rat. I. cell differentiation" *Journal of Comparative Neurology* 155(4):469–4814 (Jun. 15, 1974).

Lee et al., "Evidence that FGF8 signalling from the midbrain–hindbrain junction regulates growth and polarity in the developing midbrain" *Development* 124(5):959–969 (Mar. 1997).

Lester, D., "The concentration of neurotransmitter metabolites in the cerebrospinal fluid of suicidal individuals: a meta–analysis" *Pharmacopsychiatry* 28(2):45–50 (Mar. 1995).

Levivier et al., "Intrastriatal implantation of fibroblasts genetically engineered to produce brain–derived neurotrophic factor prevents degeneration of dopaminergic neurons in a rat model of Parkinson's disease" *Journal of Neuroscience* 15(12):7810–7820 (Dec. 1995).

Liem et al., "A role for the roof plate and its resident TGFβ–related proteins in neuronal patterning in the dorsal spinal cord" *Cell* 91(1):127–138 (Oct. 3, 1997).

Lin et al., "GDNF: A Glial Cell Line–Derived Neurotrophic Factor for Midbrain Dopaminergic Neurons" *Science* 260:1130–1132 (1993).

Lin et al., "Purification and initial characterization of rat B49 glial cell line–derived neurotrophic factor" *Journal of Neurochemistry* 63(2):758–768 (Aug. 1994).

Lumsden and Krumlauf, "Patterning the vertebrate neuraxis" *Science* 274(5290) :1109–1115 (Nov. 15, 1996).

MacArthur et al., "FGF–8 isoforms activate receptor splice forms that are expressed in mesenchymal regions of mouse development" *Development* 121(11):3603–3613 (Nov. 1995).

Malmgren, R., "The central serotoninergic system" *Cephalalgia* 10:199–204 (1990).

Marin and Puelles, "Patterning of the embryonic avian midbrain after experimental inversions: a polarizing activity from the isthmus" *Developmental Biology* 163(1):19–37 (May 1994).

Martinez et al., "Induction of ectopic engrailed expression and fate change in avian rhombomeres: intersegmental boundaries as barriers" *Mechanisms of Development* 51(2–3):289–303 (Jun. 1995).

Merrifield, R.B., "Solid Phase Peptide Synthesis. I. the Synthesis of a Tetrapeptide" *J. Am. Chem. Soc.* 85:2149–2154 (1963).

Meyers et al., "An Fgf8 mutant allelic series generated by Cre– and Flp–mediated recombination" *Nature Genetics* 18(2):136–141 (Feb. 1998).

Miller et al., "Central administration of rhGDNF causes augmentation of dopaminergic activity in vivo" *Society for Neuroscience Abstracts* (Abstract #535.7) 20:1300 (1994).

Muhr et al., "Assignment of early caudal identity to neural plast cells by a signal from caudal paraxial mesoderm" *Neuron* 19(3):487–502 (Sep. 1997).

Nadaud et al., "Functional recovery following transplantation of ventral mesencephalic cells in rat subjected to 6–OHDA lesions of the mesolimbic dopaminergic neurons" *Brain Research* 304(1):137–141 (Jun. 18, 1984).

Niswander and Martin, "Fgf–4 expression during gastrulation, myogenesis, limb and tooth development in the mouse" *Development* 114(3):755–769 (Mar. 1992).

Ohuchi et al., "Involvement of androgen–induced growth factor (FGF–8) gene in mouse embryogenesis and morphogenesis" *Biochemial & Biophysical Research Communications* 204(2) :882–888 (Oct. 28, 1994).

Pownall et al., "eFGF, Xcad3 and Hox genes form a molecular pathway that establishes the anteroposterior axis in Xenopus" *Development* 122(12):3881–3892 (Dec. 1996).

Rosenblad et al., "Glial cell line–derived neurotrophic factor increases survial, growth and function of intrastriatal fetal nigral dopaminergic grafts" *Neuroscience* 75(4):979–985 (Dec. 1996).

Rosenthal, A., "Auto Transplants for Parkinson's Disease" *Neuron* 20:169–172 (Feb. 1998).

Rubenstein, et al., "The embryonic vertebrate forebrain: the prosomeric model" *Science* 266(5185):578–580 (Oct. 28, 1994).

Shimamura and Rubenstein, "Inductive interactives direct early regionalization of the mouse forebrain" *Development* 124(14) :2709–2718 (Jul. 1997).

Shimamura et al., "Longitudinal organization of the anterior neural plate and neural tube" *Development* 121(12):3923–3933 (Dec. 1995).

Silberstein, S., "Serotonin (5–HT) and Migraine" *Headache* 34:408–417 (Jul./Aug. 1994).

Simon et al., "Independent assignment of antero–posterior and dorso–ventral positional values in the developing chick hindbrain" *Current Biology* 5(2):205–214 (Feb. 1, 1995).

Smidt et al., "A homeodomain gene Ptx3 has highly restricted brain expression in mesencephalic dopaminergic neurons" *Proc. Natl. Acad. Sci. USA* 94(24):13305–13310 (Nov. 25, 1997).

Snyder et al., "Drugs, Neurotransmitters, and Schizophrenia" *Science* 184:1243–1253 (Jun. 21, 1974).

Specht et al., "Light–microscopic immunocytochemical localization of tyrosine hydroxylase in prenatal rat brain. II. Late ontogeny" *Journal of Comparative Neurology* 199(2):255–276 (Jun. 20, 1981).

Stewart et al. *Solid–Phase Peptide Synthesis*, San Francisco, CA:W.H. Freeman Co. (1969).

Stromberg et al., "Glial Cell Line–Derived Neurotrophic Factor is Expressed in the Developing but Not Adult Striatum and Stimulates Developing Dopamine Neurons in Vivo" *Exp. Neurol.* 24:401–412 (1993).

Sutcliffe, J., "Complete nucleotide sequence of the *Escherichia coli* plasmid pBR322" Cold Spring Habor Symposia on Quantitative Biology 43:77–90 (1979).

Tanabe and Jessell, "Diversity and pattern in the developing spinal cord" *Science* 274(5290):1115–1123 (Nov. 15, 1996).

Ungerstedt, U., "Adipsia and aphagia after 6–hydroxydopamine induced degeneration of the nigro–striatal dopamine system" *Acta Physiologica Scandinavica* 367(Suppl.) :95–122 (1971).

Walsh and Doherty, "Neural cell adhesion molecules of the immunoglobulin superfamily: role in axon growth and guidance" *Annual Review of Cell & Developmental Biology* (see pp. 441–446) 13:425–456 (1997).

Welch, K., "The therapeutics of migraine" *Current Opinion in Neurology & Neurosurgery* 6:264–269 (Apr. 1993).

Wellstein et al., "Autocrine growth stimulation by secreted Kaposi fibroblast growth factor but not by endogenous basic fibroblast growth factor" *Cell Growth & Differentiation* 1(2):63–71 (Feb. 1990).

Wilder et al., "Inactivation of the FGF-4 gene in embryonic stem cells alters the growth and/or the survival of their early differentiated progeny" *Developmental Biology* 192(2):614–629 (Dec. 15, 1997).

Wolpert, L., "Positional information and the spatial pattern of cellular differentiation" *Journal of Theoretical Biology* 25(1):1–47 (Oct. 1969).

Yansura and Simmons, "Nucleotide Sequence Selection for Increased Expression of Heterologous Genes in *Escherichia Coli*" *Methods: A companion to Methods in Enzymology* 4(2):151–158 (1992).

Ye et al., "Intersections of the FGF8 and Shh Signals Create Inductive Centers for Dopaminergic and Serotonergic Neurons in the Anterior Neural Plate" *Keystone Symposia on Molecular and Cellular Biology* (Abstract #243, Steamboat Springs, Colorado Apr. 3–8,1998) pp. 100 (1998).

Yoshida et al., "Genomic sequence of hst, a transforming gene encoding a protein homologous to fibroblast growth factors and the int–2–encoded protein" *Proc. Natl. Acad. Sci. USA* 84(20):7305–7309 (Oct. 1987).

Yurek and Sladek, "Dopamine Cell Replacement: Parkinson's Disease" *Annual Review of Neuroscience* 13:415–440 (1990).

Zanella et al., "Angiotensin–converting enzyme (ACE) inhibition. Therapeutic option for diabetic hypertensive patients" *Drugs* 39(Suppl. 2):33–39 (1990).

Zeng et al., "Altered motor function and graft survival produced by basic fibroblast growth factor in rats with 6–OHDA lesions and fetal ventral mesencephalic grafts are associated with glial proliferation" *Experimental Neurology* 139(2):214–226 (Jun. 1996).

Zhou et al., "Influence of BDNF on the expression of the dopaminergic phenotype of tissue used for brain transplants" *Developmental Brain Research* 100(1):43–51 (May 20, 1997).-

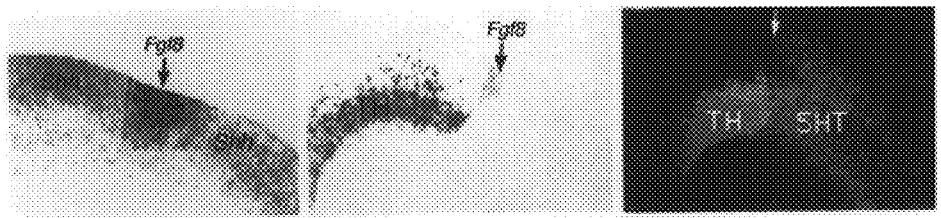
FIG. IA  FIG. IB  FIG. IC
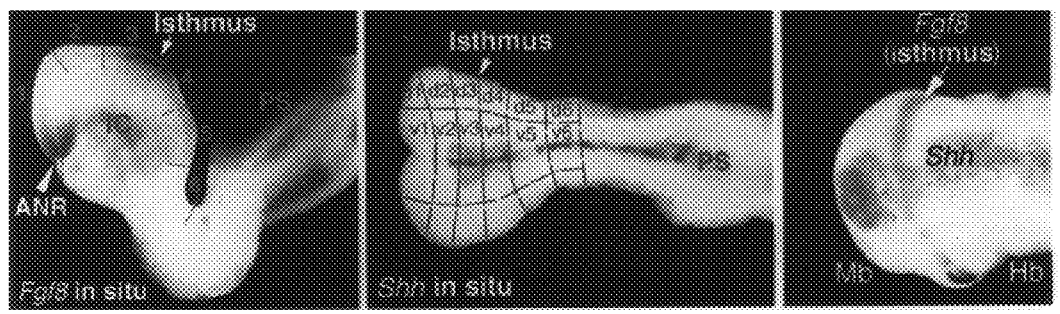
FIG. ID  FIG. IE  FIG. IF
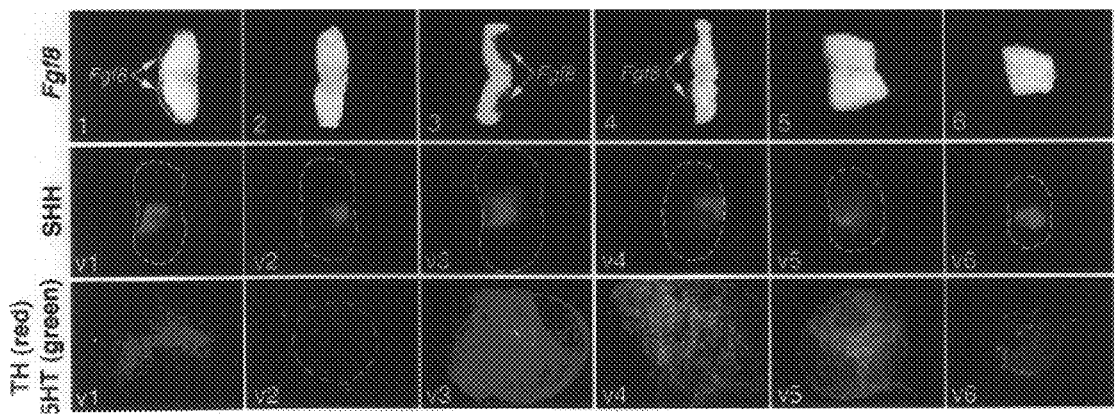
FIG. IG

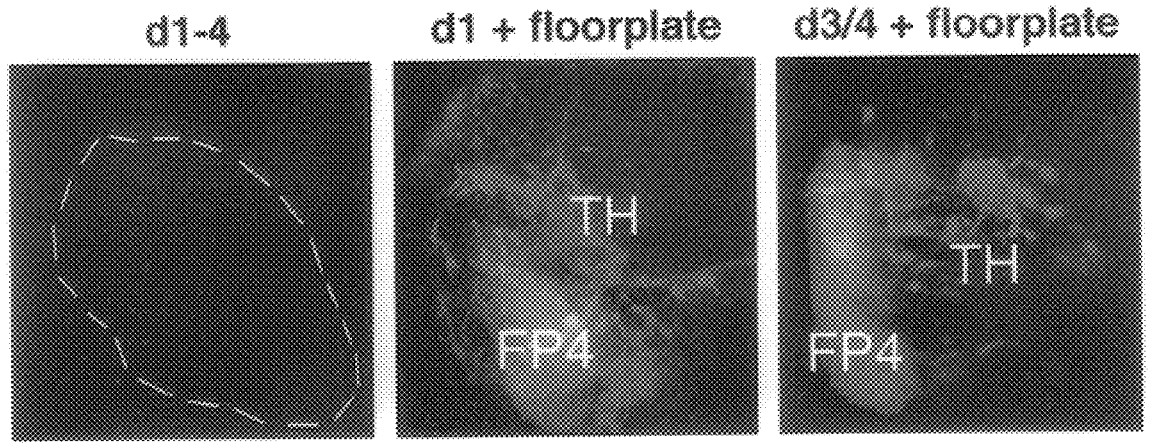
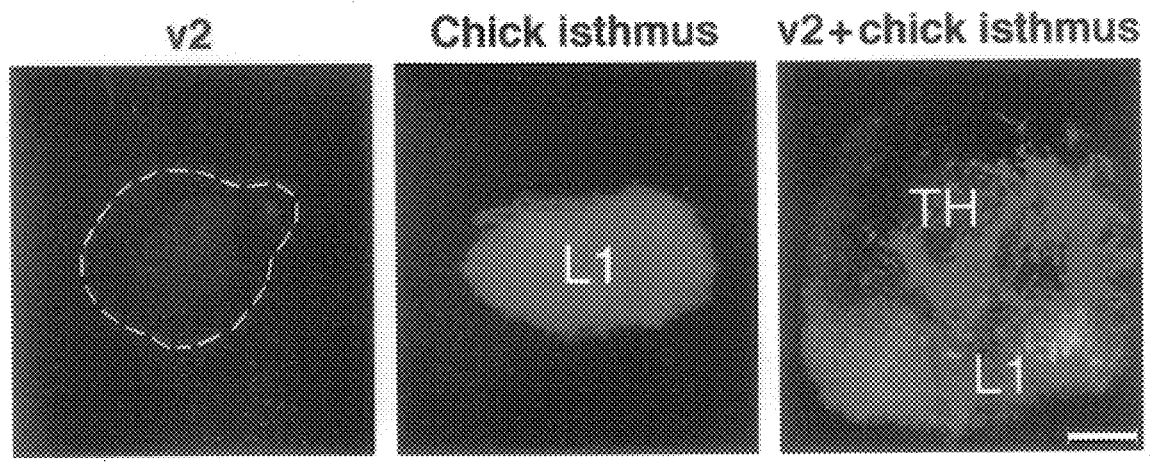

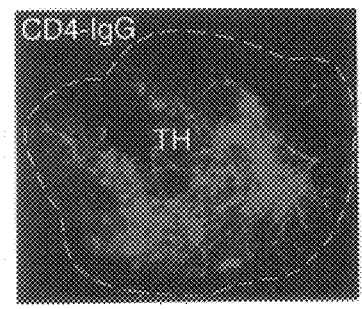
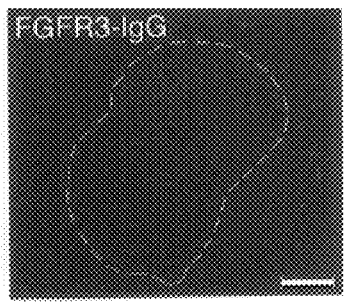
FIG. 6A FIG. 6B
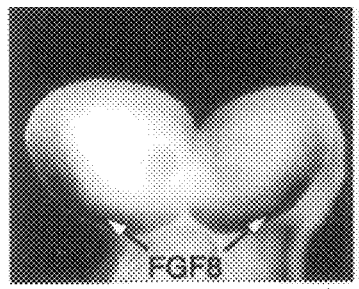
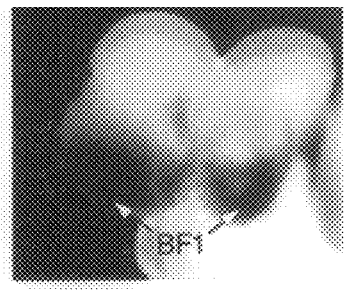
FIG. 6C FIG. 6D
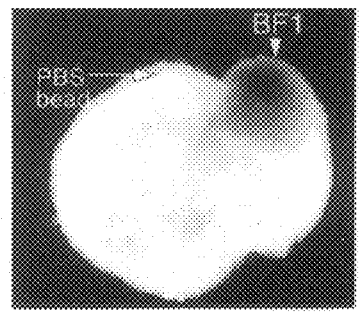
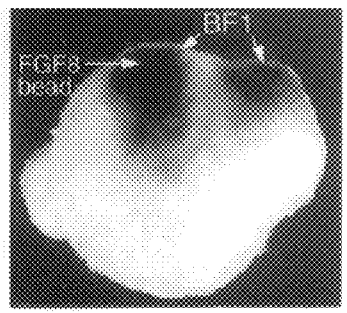
FIG. 6E FIG. 6F
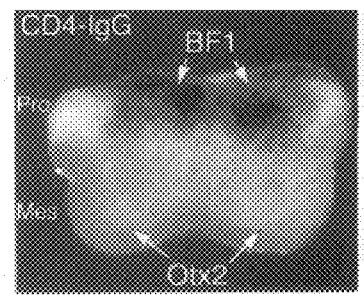
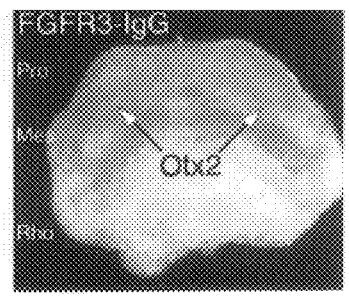
FIG. 6G FIG. 6H

```
> Wed Apr 1 1998 15:28:51
> ss.untitled19 [MUSFGFB]
> 0 Sites [No Sites]
> length: 609 bp (circular)
>MUSFGFB    Mouse K-fibroblast growth factor (Fgfk) mRNA, complete cds. 609 bp 1 ATGGCGAAAC GCGGGCCGAC CACAGGACG CTGCTGCCCA GGGTCCTGCT GGCCCTGGTG GTGGCCCTGG CGGACCGAGG GACCGCCGAG CCCAACGGCA  SEQ ID NO 1
    TACCGCTTTG CGCCCGGCTG GTGTCCCTGC GACGACGGGT CCCAGGACGA CCGGGACCAC CACCGGGACC GCCTGGGCTCC CTGGCGGCGT GGGTTGCCGT        SEQ ID NO 2
  1  M  A  K  R  G  P  T  T  G  T  L  L  P  R  V  L  L  A  L  V  V  A  L  A  D  R  G  T  A  E  P  N  G  T 101 CGCGGCACGC AGAATTGGGG CACGGGCTGG ACGGCTTGGT GGCCCGCTCG CTGGCACGCC TGCCGGTGGC CCGCAGCCC CGGCAGGCGG CGGTCCGCAG
    GCGCCGTGCG TCTTAACCCC GTGCCGACCC TGCCGAACCA CCGGGCGAGC GACCGTGCGG GACCGTGCGG ACGGCCACCG GGCGTCCGCC GCCAGGCGTC
 35  R  H  A  E  L  G  H  G  W  D  G  L  V  A  R  S  L  A  R  L  P  V  A  A  Q  P  P  Q  A  A  V  R  S 201 CGGCGCAGGG GACTACCTGC TGGGCCTCAA AAGGCTTCGG CGGCTCTACT GCAACGTGGG CATCGGATTC CACCTGCAGG TGCTGCCCGA CGGCCGGATC
    GCCGCGTCCC CTGATGGACG ACCCGGAGTT TTCCGAAGCC GCCGAGATGA CGTTGCACCC GTAGCCTAAG GTGGACGTCC ACGACGGGCT GCCGGCCTAG
 68  G  A  G  D  Y  L  L  G  L  K  R  L  R  R  L  Y  C  N  V  G  I  G  F  H  L  Q  V  L  P  D  G  R  I 301 GGTGGTGTGC ACGCAGACAC GAGGGACAGT CTCCCTGTCA GAAGACCTCG AGAGAGGCCA CGTCGCTCCG CAGCGAGGC GTGGTGAGCA TCTTCGGAGT GGCCAGCCGG TCTTCGTGG
    CCACCACACG TGCGTCTGTG CTCCCTGTCA GAGAGGACAGT CTCTGGAGC TCTCTCCGGT CAGCGAGGC CGTCGCTCCG CACCACTCGT AGAAGCCTCA CCGGTCGGCC AAGAAGCACC
101  G  V  H  A  D  T  R  D  S  L  L  E  L  S  P  V  Q  R  G  V  V  S  I  F  G  V  A  S  R  F  F  V  A 401 CCATGAGCAG CAGGGGCAAG CTCTTCGGTG TGCCTTCTT TACCGACGAG TGTAAATTCA AAGAATACT TCTGCCCAAC AACTACAACG CCTACGAATC
    GGTACTCGTC GTCCCCGTTC GAGAAGCCAC ACGGAAGAA ATGGCTGCTC ACATTTAAGT TTCTTATGA AGACGGGTTG TTGATGTTGC GGATGCTTAG
135  M  S  S  R  G  K  L  F  G  V  P  F  F  T  D  E  C  K  F  K  E  I  L  L  P  N  N  Y  N  A  Y  E  S 501 CTACGCGTAC CCCGGTATGT TCATGGCCCT CAGTAAGCCT CAGTAAGCCC AGAAGGGGAA CCGAGTGTCG CCTACCATGA AGTAACCCA CTTCCTTCCT
    GATGCGCATG GGGCCATACA AGTACCGGGA GTCATTCTTG TCATTCGGG TCTTCCCCTT GGCTCACAGC GGATGGTACT TCCATTGGGT GAAGGAAGGA
168  Y  A  Y  P  G  M  F  M  A  L  S  K  N  G  R  T  K  K  G  N  R  V  S  P  T  M  K  V  T  H  F  L  P

601 AGACTGTGA
    TCTGACACT
201  R  L  O
```

FIG. 9

```
> Wed Apr 1 1998 15:41:40
> ss.untitled22 [MUSAIGF1]
> 0 Sites [No Sites]
> length: 997 bp (circular)
>MUSAIGF1 (FGF-8)    Mouse mRNA for fibroblast growth factor, complete cds. 997 bp
```

```
  1 CGCGCGCGGC GAGCACGACA TTCCACGGGA CCCGCCGAGC CGCGTCGGGA TAGCCGCTGG CCTCCCGCAC CCCGACCTCC CTCAGCCTCC GCACCTTCGG   SEQ ID NO 3
    GCGCGCGCCG CTCGTGCTGT AAGGTGGCCT GGGCGGCTCG GCGCAGCCCT ATCGGCGACC GGAGGGCGTG GGGCTGGAGG GAGTCGGAGG CGTGGAAGCC

101 CTTGTCCCCC CGGCGCCTCC AGTGGGACGG CGTGACCCCG CTCGGGCTCT CAGTGCTCCC GGGGCCGCGC GCCATGGGCA GCCCCCGCTC CGGCTGAGC    SEQ ID NO 4
    GAACAGGGGG GCCGCGGAGG TCACCCTGCC GCACTGGGGC GAGCCCGAGA GTCACGAGGG CCCCGGCGCG CGGTACCCGT CGGGGCCGAG GCCGACTCG
  1                                                                                          M G S  P R S    A L S

201 TGCCTGCTGT TGCACTTGCT GGTTCTCTGC CTCCAAGCCC AGTTAACTGT TCAGTCCTCA CCTAATTTTA CACAGATGT GAGGGAGCAG AGCCTGGTGA
    ACGGACGACA ACGTGAACGA CCAAGACACG GAGGTTCGGG TCAATTGACA AGTCAGGAGT GGATTAAAAT GTGTCGTACA CTCCCTCGTC TCGGACCACT
 10  C L L L  H L L  V L C  L Q A Q  V T V  Q S S   P N F T   Q H V   R E Q    S L V T

301 CGGATCAGCT CAGCCCCCGC CTCATCCGGA CCTACCAGCT CTACAGCCGC ACCAGCGGGA AGCACGTGCA GGTCCTCGCC AACAAGCGCA TCAACGCCAT
    GCCTAGTCGA GTCGGGGGCG GAGTAGGCCT GGATGGTCGA GATGTCGGCG TGGTCGCCCT TCGTGCACGT CCAGGACGCG TTGTTCGCGT AGTTGCGGTA
 44  D Q L  S R R   L I R T  Y Q L   Y S R   T S G K   H V Q   V L A   N K R I   N A M

401 GGCAGAAGAC GGAGACCCCT TCCGCAAGCT CATTGTGGAG ACCGATACTT TTGGAAGCAG AGTCCGAGTT CGGGGCGCAG AGACAGGTCT CTACATCTGC
    CCGTTCTTCTG CCCTGGGGA AGGCGTTCGA GTAACACCTC TGGCTATGAA AACCTTCGTC TCAGGCTCAA GCCCCGCGTC TCTGTCCAGA GATGTAGACG
 77  A E D   G D P F   A K L   I V E   T D T F   G S R   V R V   R G A E   T G L   Y I C

501 ATGAACAAGA AGGGGAAGCT AATTGCCAAG AGCAACGGCA AAGGCAAGGA CTGCGTATTC ACAGAGATCG TGCTGGAGAA CAACTACACG GCGCTGCAGA
    TACTTGTTCT TCCCCTTCGA TTAACGGTTC TCGTTGCCGT TTCCGTTCCT GACGCATAAG TGTCTCTAGC ACGACCTCTT GTTGATGTGC CGCGACGTCT
110  M N K K   G K L   I A K   S N G K   G K D   C V F   T E I V   L E N   N Y T   A L Q N

601 ACGCCAAGTA CGAGGGCTGG TACATGGCCT TTACCCGCAA GCAGCACCAG GGGCCGGCCC CGCTTCGAGT TCCTCAACTA CCCGCCCTTC ACGGCCAGCC
    TGCGGTTCAT GCTCCCGACC ATGTACCGGA AATGGGCGTT CGTCGTGGTC CCCGGCCGGG GCGATTCATC AGGAGTTGAT GGGCGGGAAG TGCCGGTCGG
144  A K Y   E G W   Y M A F   T R K   Q H Q   G R P   R K G S   K T R   Q H Q   R E V H   F M K

701 GCGCCCTGCC CGGGGCCACC ACACCACGGA GCAGAGCCTG CGCTTCGAGT TCCTCAACTA CCCGCCCTTC ACGCGCAGCC TGCGCGGCAG CCAGAGGACT
    CGCGGGACGG GCCCCGGTGG TGTGGTGCCT CGTCTCGGAC GCGAAGCTCA AGGAGTTGAT GGGCGGGAAG TGCGCGTCGG ACGCGCCGTC GGTCTCCTGA
177  R L P   R G H H   T T E   Q S L   R F E F   L N Y   P P F   T R S L   R G S   Q R T

801 TGGGCCCCGG AGCCCCGATA GGCGCTCGCC CAGCTCCTCC GCCGAGGAGG GGTGGGTCGG CCGGCTCCCT AGTTCGCCCT GCTCGGCGGC ACAGCAAAGG GGAGGGCTG
    ACCCGGGGCC TCGGGGCTAT CCGCAGCGGG GTCGAGGAGG CGGCTCCTCC CCACCCAGCC GGCCGAGGGA TCAAGCGGGA CGAGCCGCCG TGTCGTTTCC CCTCCCCGAC
210  W A P E  P R O

901 GGGAGCTGCC TTCTAGTTGT GCATATTGTT TGCTGTTGGG TTTTTTGTT TTTTGTTTT TGTTTTTGTT TTTTGTTTT TAAACAAAAG AGAGGCG
    CCCTCGACGG AAGATCAACA CGTATAACAA ACGACAACCC AAAAAACAA AAAACAAAA ACAAAACAA AAAACAAAA ATTTGTTTTC TCTCCGC
```

FIG. 10

```
> Wed Apr 1 1998 15:34:33
> ss.untitled21 [MMSHH]
> 0 Sites [No Sites]
> length: 1314 bp (circular)
>MMSHH        M.musculus (C57BL/6J) Shh mRNA. 1314 bp, RNA, ROD 04-NOV-1997

1 ATGCTGCTGC TGCTGGCCAG ATGTTTTCTG GTGATCCTTG CTTCCTCGCT GCTGGTGTGC CCCGGGCTGG CCTGTGGGCC CGGCAGGGGG TTTGAAAGA    SEQ ID NO 5
    TACGACGACG ACGACCGGTC TACAAAGAC CACTAGGAAC GAAGGAGCGA CGACCACACG GGGCCCGACC GGACACCCGG GCCGTCCCCC AAACTTTCT    SEQ ID NO 6
  1 M  L  L  L  A  R   C  F  L   V  I  L  A   S  S  L   L  V  C   P  G  L   A  C  G  P   G  R  G   F  G  K  R

101 GGCGGCACCC CAAAAAGCTG ACCCCTTTAG CCTACAAGCA GTTTATTCCC AACGTAGCCG AGAAGACCCT AGGGGCCAGC AGGAGATATG AAGGGAAGAT
    CCGCCGTGGG GTTTTTCGAC TGGGGAAATC GGATGTTCGT CAAATAAGGG TTGCATCGGC TCTTCTGGGA TCCCCGGTCG CCGTCTATAC TTCCCTTCTA
 35 R  H  P  K  K  L   T  P  L  A   Y  K  Q   F  I  P   N  V  A  E   K  T  L   G  A  S   R  R  Y  E   G  K  I

201 CACAAGAAAC TCCGAACGAT TTAAGGAACT TACAACCCCG ACATCATATT TAAGGATGAG GAAAAACACG GAGCAGAGCG GCTGATGACT
    GTGTTCTTTG AGGCTTGCTA AATTCCTTGA ATGTTGGGGC TGTAGTATAA ATTCCTACTC CTTTTGTGCC CTCGTCTCGC CGACTACTGA
 68 T  R  N   S  E  R  F   K  E  L   T  P  N   Y  N  P  D   I  I  F   K  D  E   E  N  T  G   A  D  R   L  M  T

301 CAGAGGTGCA AAGACAAGT AAATGCCTTG GCCATCTCTG TGATGAACCA GTGGCCTGGA GTGAAGCTGC GAGTGACCGA GGGCTGGGAT GAGGACGGCC
    GTCTCCACGT TTCTGTTCAA TTTACGGAAC CGGTAGAGAC ACTACTTGGT CACCGGACCT CACTTCGACG CTCACTGGCT CCCGACCCTA CTCCTGCCGG
101 Q  R  C  K   D  K  L   N  A  L   A  I  S  V   M  N  Q   W  P  G   V  K  L  R   V  T  E   G  W  D   E  D  G  H

401 ATCATTCAGA GGAGTCTCTA CACTATGAGG GTCGAGCAGT GGACATCACC ACGTCCGACC CCTGGTGTGG CAAGTACGGC ATGCTGGCTC GCCTGGCTGT
    TAGTAAGTCT CCTCAGAGAT GTGATACTCC CAGCTCGTCA CCTGTAGTGG TGCAGGCTGG GGACCACGTC GTTCATGCCG TACGACCGAG CGGACCGACA
135 H  S  E   E  S  L   H  Y  E  G   R  A  V   D  I  T   T  S  D  R   P  W  C  G   K  Y  G   M  L  A  R   L  A  V

501 GGAAGCAGGT TTCGACTGGG TCTACTATGA ATCCAAAGCT CACATCCACT GTTCTGTGAA AGCAGAGAAC TCCGTGGCGG CCAAATCCGG CGGCTGTTTC
    CCTTCGTCCA AAGCTGACCC AGATGATACT TAGGTTTCGA GTGTAGGTGA CAAGACACTT TCGTCTCTTG AGGCACCGCC GGTTTAGGCC GCCGACAAAG
168 E  A  G   F  D  W  V   Y  Y  E   S  K  A   H  I  H  C   S  V  K   A  E  N   S  V  A  A   K  S  G   G  C  F

601 CCGGGATCCG CCACCCTGCA GGCGGCACCA AGCTGGTGAA GGACTTGAGG CCCGGAGACC GGGTGCTGGC GGCTGACGAC CAGGGCCGGC
    GGCCCTAGGC GGTGGGACGT CCGCCGTGGT TCGACCACTT CCTGAATGCA GGGCCTCTGG CCCACGACCG CCGACTGCTG GTCCCGGCCG
201 P  G  S  A   T  V  H   L  E  Q   L  V  K   D  L  R   P  G  D  R   V  L  A   A  D  D   Q  G  R  L

701 TGCTGTACAG CGACTTCCTC ACCTTCCTGG ACCGCGACGA AGGCGCCAAG AAGGTCTTCT ACGTGATCGA GACGCTGGAG CCGCGCGAGC GCCTGCTGCT
    ACGACATGTC GCTGAAGGAG TGGAAGGACC TGGCGCTGCT TTCCAGAAGA TGCACTAGCT CTGCGACCTC GGCGCGCTCG CGGACGACGA
235 L  Y  S   D  F  L   T  F  L  D   R  D  E   G  A  K   K  V  F  Y   V  I  E   T  L  E   P  R  E  R   L  L  L

801 CACCCGCCGG CACCTGCTCT TCGTGGCGCC GCACAACGAC TCGTGGCCCC AAGCCGGGTC TTCGGACGAC TTTGCCAGCC AAGCGCGCTC GCCTGCGCCC
    GTGGGCGGCC GTGGACGAGA AGCACCGCGG CGTGTTGCTG AGCACCGGGG TTCGGCCCAG AAGCCTGCTG AAACGGTCGG TTCGCGCGAG CGGACGCGGG
268 T  A  A   H  L  L  F   V  A  P   H  N  D   S  G  P  T   P  G  P   S  A  L   F  A  S  R   V  R  P   G  Q  R
```

FIG. IIA

```
 901 GTGTACGTGG TGGCTGAACG CGGCGGGGAC CGCCGGCTGC TGCCCGCCGC GGTGCACAGC GTGACGCTGC GAGAGGAGGA GGCGGGCGCC TACGCGCGGC
     CACATGCACC ACCGACTTGC GCCGCCCCTG GCGGCCGACG ACGGGCGGCG CCACGTGTCG CACTGCGACG CTCTCCTCCT CCGCCCGCGG ATGCGCGGCG
 301  V  Y  V  V  A  E  R  G  G  D  R  R  L  L  P  A  A  V  H  S  V  T  L  R  E  E  E  A  G  A  Y  A  P  L

1001 TCACGGCGCA CGGCACCATT CTCATCAACC GGGTGCTCGC GCTGTCATCG AGGAGCACAG CTGGCACACA CGGCCTTCG CGCCTTTCCG
     AGTGCCGCGT GCCGTGGTAA GAGTAGTTGG CCCACGAGCG CGACAGTAGC TCCTCGTGTC GACCGTGTGT GCCGGAAGC GCGGAAAGGC
 335  T  A  H  G  T  I  L  I  N  R  V  L  A  S  C  Y  A  V  I  E  E  H  S  W  A  H  R  A  F  A  P  F  F  R

1101 CCTGGCGCAC GCGCTGCTGG CCGGCGCTGGC ACGGACGGCG GGGGCGGGGG CAGCATCCCT GCAGCGGCAAT CTGCAACGGA AGCGAGGGGC
     GGACCGCGTG CGCGACGACC GGCCGCGACCG TGCCTGCCGC CCCCGCCCCC GTCGTAGGGA CGTCGCCGTTA GACGTTGCCT TCGCTCCCCG
 368  L  A  H  A  L  L  A  A  L  A  P  A  R  T  D  G  G  G  G  G  S  I  P  A  A  Q  S  A  T  E  A  R  G

1201 GCGGAGCCGA CTGCGGGCAT CCACTGGTAC TCGCAGCTGC TGGTTGGACA GCGAGACCAT GCATCCCTTG GGAATGGCGG
     CGCCTCGGCT GACGCCCGTA GGTGACCATG AGCGTCGACG GACAACCTGT CGCTCTGGTA CGTAGGGAAC CCTTACCGCC
 401  A  E  P  T  A  G  I  H  W  Y  S  Q  L  L  D  S  E  T  M  H  P  L  G  M  A  V

1301 TCAAGTCCAG CTGA
     AGTTCAGGTC GACT
 435  K  S  S  O
```

FIG. IIB

```
> Mon Apr 6 1998 10:30:23
> /Macintosh HD/Desktop Folder/ss.CD4
> 0 Sites [No Sites]
> length: 1383 bp (circular)
>rat CD4 ECD 1 ATGTGCCAG GCTTCTCTTT CAGGCACTTG CTGCCGCTGC TGCTCCTGCA GCTGTCAAAA CTCCTAGTTG TCACCCAAGG AAAGACCGTG GTGCTGGGGA SEQ ID NO 7
     TACACGGCTC CGAAGAGAAA GTCCGTGAAC GACGGCACG ACGAGGACGT CGACAGTTT GAGGATCAAC AGTGGGTTCC TTTCTGGCAC CACGACCCCT 101 AGGAAGGGGG TTCAGCAGAA CTGCCCTGTG AAAGTACCTC GAGGAGGAGT GCATCCTTCG CGTGGAAGTC CTCTGACCAA AAGACAATTC TGGGATATAA
     TCCTTCCCCC AAGTCGTCTT GACGGGACAC TTTCATGGAG CTCCTCCTCA CGTAGGAAGC GCACCTTCAG GAGACTGGTT TTCTGTTAAG ACCCTATATT 201 GAACAAGTA TTGATTAAAG GTTCACTTGA GCTGTATAGT CGTTTTGATT CCAGAAAAAA TGCATGGGAG AGAGGATCAT TTCCCCTCAT CATCAATAAA
     CTTGTTCAAT AACTAATTTC CAAGTGAACT CGACATATCA GCAAAACTAA GGTCTTTTTT ACGTACCCTC TCTCCTAGTA AAGGGGAGTA GTAGTTATTT 301 CTTAGGATGG AGGACTCTCA GACTTATGTC TGCGAGCTGG AGAACAAGAA AGAGGAGGTG CAGTTGTGG TCTTTCAGAGT GACCTTCAAT CCGGGTACCA
     GAATCCTACC TCCTGAGAGT CTGAATACAG ACGCTCGACC TCTTGTTCTT TCTCCTCCAC CTCAACACCC AGAAGTCTCA CTGGAAGTTA GGCCCATGGT 401 GACTGTGCA GGGGCAGAGC CTGACCCTGA TCTTGGATAG CAACCCTAAG GTCTCTGACC CCCGATAGA GTGCAAACAC AAAAGCAGTA ACATTGTCAA
     CTGACAACGT CCCCGTCTCG GACTGGGACT AGAACCTATC GTTGGGATTC CAGAGACTGG GGGGCTATCT CACGTTTGTG TTTTCGTCAT TGTAACAGTT 501 GGACTCCAAA GCTTTCTCCA CGGACAGCCT AAGGATTCAG GACAGTGGCA TCTGAACTG CACCGTGACC CTGAACCAGA AGAAGCACTC ATTTGACATG
     CCTGAGGTTT CGAAAGAGGT GCCTGTCGGA TTCCTAAGTC CTGTCACCGT AGACCTTGAC GTGGCACTGG GACTTGGTCT TCTTCGTGAG TAAACTGTAC 601 GGACTCCAAA TGCTGGGCTT AAGAAAATTG TGCCAAGGA AAGAAAATTG TGCCAAGGGA ATGCAATCCT TGTGACTGTA CAGGCTCAGA AGTATCATCT GTCTTCATCT
     TTTGAGAGTC ACGACCCGAA ACGCCAGCTG TTCTTTTAAC ACGGTTCCCT TACGTTAGGA ACACTTACAT GTCCGAGTCT TCATAGTAGA CAGAAGTAGA
                                                                                           ^Hinge region
                                                                This is the rat IgG2a sequence of the PCR clone from rat spleen poly A RNA 701 TCCCCCCAAA GACCAAAGAT GTGCTCACCA TCACTCTGAC TCCTAAGGTC ACGTGTGTTG TGGTAGACAT TAGCCAGAAT GATCCCGAGG TCCGGTTCAG
     AGGGGGGTTT CTGGTTTCTA CACGAGTGGT AGTGAGACTG AGGATTCCAG TGCACACAAC ACCATCTGTA ATCGGTCTTA CTAGGCTCC AGGCCAAGTC
     ^CH2 region 801 CTGGTTTATA GATGACGTGG AAGTCCACAC AGCTCAGACT CATGCCCCGG AGAAGCAGTC CAACAGCACT TTACGCTCAG TCAGTGAACT CCCCATCGTG
     GACCAAATAT CTACTGCACC TTCAGGTGTG TCGAGTCTGA GTACGGGCC TCTTCGTCAG GTTGTCGTGA AATGCGAGTC AGTCACTTGA GGGGTAGCAC 901 CACCGGGACT GGCTCAATGG CAAGACGTTC AAATGCAAAG TCAACAGTGA AGCATTCCCT GCCCCCATCG AGAAAAGCAT CTCCAAACCC GAAGGCACAC
     GTGGCCCTGA CCGAGTTACC GTTCTGCAAG TTTACGTTTC AGTTGTCACC TCGTAAGGGA CGGGGGTAGC TCTTTTCGTA GAGGTTTGGG CTTCCGTGTG
                                                                                                       ^CH3 region 1001 CACGAGGTCC ACAGGTATAC ACCATGGCGC CTCCAAGGA CAGAGATGACC CAGAGTCAAG TCAGTATAC CTGATGGTA AAAGGCTTCT ATCCCCCAGA
     GTGCTCCAGG TGTCCATATG TGGTACCGCG GAGGGTTCCT TCTCTACTGG GTCTCAGTTC AGTCATAGTG GACTACCAT TTTCCAAGA TAGGGGTCT 1101 CATTTATACG GAGTGGAAGA TGAACGGGCA GCCACAAGAA AACTACAAGA ACACTCCACC TACGATGGAC ACAGATGGAA GTTACTTCCT CTACAGCAAG
     GTAAATATGC CTCACCTTCT ACTTGCCCGT CGGTGTTCTT TTGATGTTCT TGTGAGGTGG ATGCTACCTG TGTCTACCCT CAATGAAGGA GATGTCGTTC
```

FIG. 12A

```
1201 CTCAATGTAA AGAAAGAAAC ATGGCAGCAG GGAAACACTT TCACGTGTTC TGTGCTGCAT GAGGGCCTGC ACAACCACCA TACTGAGAAG AGTCTCTCCC
     GAGTTACATT TCTTTCTTTG TACCGTCGTC CCTTTGTGAA AGTGCACAAG ACACGACGTA CTCCCGGACG TGTTGGTGGT ATGACTCTTC TCAGAGAGGG

1301 ACTCTCCTGG TAAATGACCC AGAGAATTCA ATCGATGGCC GCCATGGCCC AACTTGTTTA TTGCAGCTTA TAATGGTTAC AAA
     TGAGAGGACC ATTTACTGGG TCTCTTAAGT TAGCTACCGG CGGTACCGGG TTGAACAAAT AACGTCGAAT ATTACCAATG TTT
                                                          ^sv40 early poly A
```

FIG. 12B

```
> Mon Apr 6 1998 10:29:09
> /Macintosh HD/Desktop Folder/ss.FGFR1
> 0 Sites [No Sites]
> length: 1983 bp (circular)
>mouse FGFR1 ECD 1 ATGTGGGGCT GGAAGTGCCT CCTCTTCTGG GCTGTGCTGG TCACAGCCAC TCTCTGCACT GCCAGGCCAG CCCCAACCTT GCCCGAACAA GCTCAGCCCT  SEQ ID NO 8
     TACACCCCGA CCTTCACGGA GGAGAAGACC CGACACGACC AGTGTCGGTG AGAGACGTGA CGGTCCGGTC GGGGTTGGAA CGGGCTTGTT CGAGTCGGGA 101 GGGGAGTCCC TGTGGAAGTG GAGTCCCTCC TGGCGACCTG CTACAGCTTC CTGTCGCCT  TCGCGATGAT GTGCAGAGCA TCAACTGGCT
     CCCCTCAGGG ACACCTTCAC CTCAGGGAGG ACCAGGTGGG ACCGCTGGAC GATGTCGAAG GACAGCGGA  AGCCTACTA  CACGTCTCGT AGTTGACCGA 201 GCGGGATGGG GTGCAGCTGG TGGAGACCAA CCCTACCGC  ATCACAGGGG AGGAGGTGGA GGTGCGGGAC TCCATCCCG  AGTAGGGGC  CTGACTCTGG CCTCTACGCT
     CGCCCTACCC CACGTCGACC ACCTCTCGTT GGGATGGCG  TAGTGTCCCC TCCTCCACCT CCACGCCCTG AGTAGGGGC  TCATCCCCG  GACTGAGACC GGAGATGCGA 301 TGGCTGACCA GCAGCCCTC  TGGCAGCGAT ACCACCTACT TCTCCGTCAA TGTCTCAGAT CCTCGGAAGA TGATGACGAC GACGATGACT
     ACGACTGGT  CGTCGGGGAG ACCGTCGCTA TGGTGGATGA AGAGGCAGTT ACAGAGTCTA GGAGCCTTCT ACTACTGCTG CTGCTACTGA 401 CCCTCCTCGA GGAGAAAGAG ACGGACAACA CCAAACCAAA CCCTGTAGCT CCCTACTGGA CATCCCCAGA GAAAATGGAG AAGAAACTGC ATGCCGTGCC
     GGAGGAGCCT CCTCTTTCTC TGCCTGTTGT GGTTTGGTTT GGGACATCGA GGGATGACCT GTAGGGGTCT CTTTTACCTC TTCTTGACG  TACGCCACGG 501 CGCTCCAAG  ACGGTGAAGT TCAAGTGCCC GTCGAGTGGG ACACCCAACC CCACTCTGCG CTGGTTGAAA AATGGCAAAG AGTTAAGCC  TGACACCGA
     GCGACGGTTC TGCCACTTCA AGTTCACGGG CAGCTCACCC TGTGGGTTGG GGTGAGACGC GACCAACTTT TTACCGTTTC TCAAATTCGG ACTGTGGCT 601 ATTGAGGGT  ACAAGGTTCA CTATGCCACC TGGAGCATCA TAATGATTC  TGTGGTGCCT TCTGACAAGG GCAACTACAC CTGCATCGTG GAGAATGAGT
     TAACCTCCGA TGTTCCAAGT GATACGGTGG ACCTCGTAGT ATTACCTAAG ACACCACGGA AGACTGTTCC CGTTGATGTG GACGTAGCAC CTCTTACTCA 701 ATGGGAGCAT CAACCACACC TACCAGCTTG ACGTCGTGGA ACGATCTCCG CACCGACCCA TCCTTCAGGC AGGGCTGCCT GCCAACAAGA CAGTGGCCCT
     TACCCTCGTA GTTGGTGTGG ATGGTCGAAC TGCAGCACCT TGCTAGAGGC GTGGCTGGGT AGGAAGTCCG TCCCGACGGA CGGTTGTTCT GTCACCGGGA 801 GGGCAGCAAT GTGGAGTTCA TGTGTAAGGT GTACAGCGAT CCGCAGCCTC ACATTCAGTG GCTGAAGCAC ATCGAGGTGA GATCGGGCCA
     CCCGTCGTTA CACCTCAAGT ACACATTCCA CATGTCGCTA GGCGTCGGAG TGTAAGTCAC CGACTTCGTG TAGCTCCACT CTAGCCCGGT 901 GACAACTTGC CGTATGTCCA GATCTGAAG  TTAATACCAC CGACAAGGAA ATGGAGGTGC TTCATCTACG GAATGTCTCC TTTGAGGATG
     CTGTTGAACG GCATACAGGT CTAGGACTTC AATTATGGTG GCTGTTCCTT TACCTCCACG AAGTAGATGC CTTACAGAGG AAACTCCTAC 1001 CGGGGAGTA  TACGTGCTTG GCGGTAACT  CTATCGGACT CTCCCATCAC TCTGCATGGT TGACCGTTCT GAAGCCCTG  GAAGAGAGAC CAGCTGTGAT
     GCCCCTCAT  ATGCACGAAC CGCCATTGA  GATAGCCTGA GAGGGTAGTG AGACGTACCA ACTGGCAAGA CCTTCGGGAC CTTCTCTCTG GTCGACACTA 1101 GACCTCACCG CTCTACGTCG ACAAGAAAAT TGTGCCAAGG GAATGCAATC CTTGTGGATG TACAGGCTCA GAAGTATCAT GAAGTATCAT CTGTCTTCAT CTTCCCCCA
     CTGGAGTGGC GAGATGCAGC TGTTCTTTTA ACACGGTTCC CTTACGTTAG GAACACGTAC ATGTCCGAGT CTTCATAGTA GACAGAAGTA GAAGGGGGT ^Hinge region                                     ^CH2 region ^This is the rat IgG2a sequence of the PCR clone from rat spleen poly A RNA

FIG. 13A
```

```
1201 AAGACCAAAG ATGTGCTCAC CATCACTCTG ACTCCTAAGG TCACGTGTGT TGTGGTAGAC ATTAGCCAGA ATGATCCCGA GGTCCGGTTC AGCTGTTTA
     TTCTGGTTTC TACACGAGTG GTAGTGAGAC TGAGGATTCC AGTGCACACA ACACCATCTG TAATCGGTCT TACTAGGGCT CCAGGCCAAG TCGACCAAAT

1301 TAGATGACGT GGAAGTCCAA ACAGCTCAGA CTCATGCCCC GGAGAAGCAG TCCAACAGCA CTTTACGCTC AGTCAGTGAA CTCCCCATCG TGCACCGGA
     ATCTACTGCA CCTTCAGTG TGTCGAGTCT GAGTACGGGG CCTCTTCGTC AGGTTGTCGT GAAATGCAAG TCAGTCACTT GAGGGTAGC ACGTGGCCCT

1401 CTGGCTCAAT GGCAAGACGT TCAAATGCAA AGTCAACAGT GGAGCATTCC CTGCCCCCAT CGAGAAAAGC ATCTCCAAAC CCGAAGGCAC ACCACGAGGT
     GACCGAGTTA CCGTTCTGCA AGTTTACGTT TCAGTTGTCA CCTCGTAAGG GACGGGGGTA GCTCTTTTCG TAGAGGTTTG GGCTTCCGTG TGGTGCTCCA
                                                                                                        ^CH3 region 1501 CCACAGGTAT ACACCATGGC GCCTCCCAAG GAAGAGATGA CCCAGAGTCA AGTCAGTATC ACCTGCATGG TAAAAGGCTT CTATCCCCCA GACATTATA
     GGTGTCCATA TGTGGTACCG CGGAGGGTTC CTTCTCTACT GGGTCTCAGT TCAGTCATAG TGGACGTACC ATTTTCCGAA GATAGGGGT CTGTAAATAT 1601 CGGAGTGGAA GATGAACGGG CAGCCACAGG GAACACTACA CCTACGATGG ACACAGATGG GAGTTACTTC CTCTACAGCA AGCTCAATGT
     GCCTCACCTT CTACTTGCCC GTCGGTGTCC TTGTGATGTT GGATGCTACC TGTGTCTACC CTCAATGAAG GAGATGTCGT TCGAGTTACA 1701 AAAGAAAGAA ACATGCGCAG AGGGAAACAC TTTCACGTGT TCTGTGCTGC ATGAGGGCCT GCACAACCAC CATACTGAGA AGAGTCTCTC CCACTCTCCT
     TTTCTTTCTT TGTACGCGTC TCCCTTTGTG AAGTGCACA AGACACGACG TACTCCCGGA CGTGTTGGTG GTATGACTCT TCTCAGAGAG GGTGAGAGGA 1801 GGTAAATGAC CCAGAGAATT CAATCGATGG CCGCCATGGC GGTTGAACAA ATAACGTCGA TATATTACCAA TGTTTATTTC GTTATCGTAG TGTTTAAAGT
     CCATTACTG GGTCTCTTAA GTTAGCTACC GGCGGTACCG GGTTGAACAA ATAACGTCGA ATATTACCAA TGTTTATTTC GTTATCGTAG TGTTTAAAGT
                                                ^sv40 early poly A 1901 CAAATAAAGC ATTTTTTTCA CTGCATTCTA GTTGTGGTTT GTCCAAACTC ATCAATGTAT CTTATCATGT CTGGATCGAT CGG
     GTTTATTTCG TAAAAAAAGT GACGTAAGAT CAACACCAAA CAGGTTTGAG TAGTTACATA GAATACTACA GACCTAGCTA GCC
```

FIG. 13B

```
> Mon Apr 6 1998 10:28:13
> /Macintosh HD/Desktop Folder/ss.FGFR3
> 0 Sites [No Sites]
> length: 1968 bp (circular)
>mouse FGFR3 ECD 1 ATGGTAGTCC CGGCCTGCGT GCTAGTGTTC TCGTGGCGG AGCTACTTCC GAGCCTCCTG GTCCAGAGCA GCGAGTGTG CGGAGAGCGG  SEQ ID NO 9
     TACCATCAGG GCCGGACGCA CGATCACAAG ACGACCGCC TCGATGAAGG CTCGGAGGAC CAGGTCTCGT CGCTCAACAC GCCTCTCGCC 101 CAGAGGTTCC AGGGCCTGAA CCTAGCCAGC AGGAGCAGT GGCCTTCGGC AGTGGGACA CCGTGGAGCT GAGCTGCCAT CCTCCTGAG GTCCCCCAC
     GTCTCCAAGG TCCCGGACTT GGATCGGTCG TCCTCGTCCA CCGGAAGCCG TCACCCCTGT GGCACCTCGA CTCGACGGTA GGAGGACCTC CACGGGGGTG 201 AGGGCCCACG GTCTGGGCTA AGGATGGTAC AGTGTCTGTG GCCTCCACC GCATCCTCGT GGGGCCTCAG AGGCTGCAAG TGCTAAATGC CTCCACGAA
     TCCCGGGTGC CAGACCCGAT TCCTACCATG TCACAGACAC CGGAGGTGG CGTAGGACCA CCCCGGAGTC TCCGACGTTC ACGATTTACG GAGGGTGCTT 301 GATGCAGGGG TCTACAGCTG CCAGCACCGG CTCACTCGGC GTGTGCTGTG CCACTTCAGT GTGCGTGTAA CAGATGCTCC ATCCTCAGGA GATGACGAAG
     CTACGTCCCC AGATGTCGAC GGTCGTGGCC GAGTGAGCCG CACACGACAC GGTGAAGTCA CACGCACATT GTCTACGAGG TAGGAGTCCT CTACTGCTTC 401 ATGGGGAGGA CGTGGCTGAA GACACAGGGG CTCCTTATTG GACTGCCCCG GAGCGAATGG ATAAGAAACT GCTGGCTGTG CCAGCCCGCA ACACTGTCCG
     TACCCCTCCT GCACCGACTT CTGTGTCCCC GAGGAATAAC CTGACGGGGC CTCGCTTACC CTCGCTTTGA CGACCGACAC GGTCGGGCGT TGTGACAGGC 501 CTTCCGCTGC CCAGTGCTG GCAAACCCTAC TCCTGCTGA AGAATGGCAA AGAATTCCGA GGGCAGCATC GCATTGGGG CATCAAGCTC
     GAAGGCGACG GGTCACGAC CGTTGGGATG AGGACCGACT TCTTACCGTT TCTTAAGGCT CCCGTCGTAG CGTAACCCCC GTAGTTCGAG 601 CGGCACCAGC AGTGGAGCTT GGTCATGGAA AGTGTGGTAC CCTCCGATCG TGGCAACTAT ACCTGTGTAG TTGAGAACAA GTTTGGCAGC ATCCGGCAGA
     GCCGTGGTCG TCACCTCGAA CCAGTACCTT TCACACATG GGAGGCTAGC ACCGTTGATA TGGACACATC AACTCTTGTT CAAACCGTCG TAGGCCGTCT 701 CATACACACT GGATGTGCTG GAGCGCTTCC CACACCGGCC CATCCTGCAG GCTGGGCTGC CGGCCAACCA GACAGCCATT CTAGGCAGTG ACGTGGAGTT
     GTATGTGTGA CCTACACGAC CTCGCGAAGG GTGTGGCCGG GTAGGACGTC CGACCCGACG GCCGGTTGGT CTGTCGGTAA GATCCGTCAC TGCACCTCAA 801 CCACTGCAAG GTGTACAGCG ATGCACAGCC ACACATCCAG TGGCTGAAGC ACGTGGAAGT GAACGGCAGC CTTGCCGTCG TGCACCTTCA AAGGTGGGCC CTGACGGCAC GCCCTACGAC
     GGTGACGTTC CACATCGTCG TACGTGTCGG TGTGTAGGTC ACCGACTTCA TGCACCTTCA CTTGCCGTCG GAACGGCAGC TTCCACCCGG GACTGCCGTG CGGATGCTG 901 ACTGTACTCA AGACTGCAGG CGCTAACACC ACCGACAAGG AGCTAGAAGT TCTGTCCCTTG CACAATGTCA CCTTTGAGGA CGCGGGGGAG TACACCTGCC
     TGACATGAGT TCTGACGTCC GCGATTGTGG TGGCTGTTCC TCGATCTCCA AGACAGGAAC GTGTTACAGT GGAAACTCCT GCGCCCCCTC ATGTGGACGG 1001 TGGGGGCAA TTCTATTGGG TTTTCCCATC ACTCTGCGTG CTGGTGGTG CTGCCAGCTG AGGAGGAGCT GATGAAACT GATGAGGCTG GCAGCGTGTA
     ACCGGCCCGTT AAGATAACCC AAAAGGGTAG TGAGACGCAC CGACCACCAC GACGGTCGAC TCCTCCTGA CTACTCCGAC CGTCGCACAT 1101 CGTCGACAAG AAAATTGTGC CAAGGAATG CAATCCTTGT GGATGTACAG GCTCAGAAGT ATCATCTGTC CCCAAAGAC CAAAGATGTG
     GCAGCTGTTC TTTTAACACG GTTCCCTTAC CCTAGAACA CCTACATGTC CGAGTCTTCA TAGTAGACAG AAGTAGAAGG GGGGTTTCTG GTTTCTACAC ^This is the rat IgG2a sequence of the PCR clone from rat spleen poly A RNA
     ^Hinge region     ^CH2 region
```

FIG. 14A

```
1201  CTCACCATCA CTCTGAGCTCC TAAGGTCACG TGTGTTGTGG TAGACATTAG CCAGAATGAT CCCGAGGTCC GGTTCAGCTG GTTTATAGAT GACGTGAAG
      GAGTGGTAGT GAGACTGAGG ATTCCAGTGC ACACAACACC ATCTGTAATC GGTCTTACTA GGGCTCCAGG CCAAGTCGAC CAAATATCTA CTGCACCTTC

1301  TCCACACAGC TCAGACTCAT GCCCCGGAGA AGCAGTCCAA CGCTCAGTCA CGCTCAGTCA GTGAACTCCC CATCGTGCAC CGGGACTGGC TCAATGGCAA
      AGGTGTGTCG AGTCTGAGTA CGGGGCCTCT TCGTCAGGTT GCGAGTCAGT CGCGAGTCAGT CACTTGAGGG GTAGCACGTG GCCCTGACCG AGTTACCGTT

1401  GACGTTCAAA TGCAAAGTCA ACAGTGGAGC ATTCCCTGCC CCCATCGAGA AAAGCATCTC CAAACCCGAA GGCACACCAC GAGGTCCACA GGTATACACC
      CTGCAAGTTT ACGTTTCAGT TGTCACCTCG TAAGGGACGG GGGTAGCTCT TTTCGTAGAG GTTTGGGCTT CCGTGGTGTG CTCCAGGTGT CCATATGTGG
                                                                                  ^CH3 region
1501  ATGGGCGCCTC CCAAGGAAGA GATGACCCAG AGTCAAGTCA GTATCACCTG CCCCAGACAT GGCTTCTATC CCCAGACAT TTATACGGAG TGGAAGATGA
      TACCGCGGAG GGTTCCTTCT CTACTGGGTC TCAGTTCAGT CATAGTGGAC GGGGTCTGTA CCGAAGATAG AATATGCCTC ACCTTCTACT 1601  ACGGGCAGCC ACAGGAAAAC TACAAGAACA CTCCACCTAC GATGGACACA CTACCTGTGT CAGCAAGCTC ACTTCCCTCTA AAGAACATG
      TGCCCGTCGG TGTCCTTTTG ATGTTCTTGT GAGGTGGATG CTACCTGTGT GTCGTTCGAG TGAAGGAGAT GTCGTTCGAG TTACATTTCT TTCTTTGTAC 1701  GCAGCAGGGA AACACTTTCA CGTGTTCTGT GCTGCATGAG GGCCTGCACA ACCACCATAC TGAGAAGAGT CTCTCCCCACT CTCCTGGTAA ATGACCCAGA
      CGTCGTCCCT TTGTGAAAGT GCACAAGACA CGACTACTC CCGGACGTGT TGGTGGTATG ACTCTTCTCA GAGAGGGTGA GAGGACCATT TACTGGGTCT 1801  GAATTCAATC GATGGCCCGCC TTGTTTATTG CAGCTTATAA TAAAGCAATA GCATCACAAA TTTCACAAAT AAAGCATTTT
      CTTAAGTTAG CTACCGGGCGG AACAAATAAC GTCGAATATT ATTTCGTTAT CGTAGTGTTT AAAGTGTTTA TTTCGTAAAA
      ^sv40 early poly A 1901  TTTCACTGCA TTCTAGTTGT GGTTTGTCCA AACTCATCAA TGTATCTTAT CATGTCTGGA TCGATCGG
      AAAGTGACGT AAGATCAACA CCAAACAGGT TTGAGTAGTT ACATAGAATA GTACAGACCT AGCTAGCC
```

FIG. 14B

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 609 base pairs
      (B) TYPE: Nucleic Acid
      (C) STRANDEDNESS: Single
      (D) TOPOLOGY: Circular (xi) SEQUENCE DESCRIPTION: SEQ ID NO:1:

ATGGCGAAAC GCGGGCCGAC CACAGGGACG CTGCTGCCCA GGGTCCTGCT    50

| | |
|---|---|
| GGCCCTGGTG GTGGCCCTGG CGGACCGAGG GACCGCCGCA CCCAACGGCA | 100 |
| CGCGGCACGC AGAATTGGGG CACGGCTGGG ACGGCTTGGT GGCCCGCTCG | 150 |
| CTGGCACGCC TGCCGGTGGC CGCGCAGCCC CCGCAGGCGG CGGTCCGCAG | 200 |
| CGGCGCAGGG GACTACCTGC TGGGCCTCAA AAGGCTTCGG CGGCTCTACT | 250 |
| GCAACGTGGG CATCGGATTC CACCTGCAGG TGCTGCCCGA CGGCCGGATC | 300 |
| GGTGGTGTGC ACGCAGACAC GAGGGACAGT CTTCTGGAGC TCTCTCCGGT | 350 |
| GCAGCGAGGC GTGGTGAGCA TCTTCGGAGT GGCCAGCCGG TTCTTCGTGG | 400 |
| CCATGAGCAG CAGGGGCAAG CTCTTCGGTG TGCCTTTCTT TACCGACGAG | 450 |
| TGTAAATTCA AGAAAATACT TCTGCCCAAC AACTACAACG CCTACGAATC | 500 |
| CTACGCGTAC CCCGGTATGT TCATGGCCCT CAGTAAGAAC GGGCGGACCA | 550 |
| AGAAGGGGAA CCGAGTGTCG CCTACCATGA AGGTAACCCA CTTCCTTCCT | 600 |
| AGACTGTGA | 609 |

(2) INFORMATION FOR SEQ ID NO:2:

(i) SEQUENCE CHARACTERISTICS:
        (A) LENGTH: 202 amino acids
        (B) TYPE: Amino Acid
        (D) TOPOLOGY: Linear (xi) SEQUENCE DESCRIPTION: SEQ ID NO:2:

```
Met Ala Lys Arg Gly Pro Thr Thr Gly Thr Leu Leu Pro Arg Val
 1               5                  10                  15

Leu Leu Ala Leu Val Val Ala Leu Ala Asp Arg Gly Thr Ala Ala
                20                  25                  30

Pro Asn Gly Thr Arg His Ala Glu Leu Gly His Gly Trp Asp Gly
                35                  40                  45

Leu Val Ala Arg Ser Leu Ala Arg Leu Pro Val Ala Ala Gln Pro
                50                  55                  60

Pro Gln Ala Ala Val Arg Ser Gly Ala Gly Asp Tyr Leu Leu Gly
                65                  70                  75

Leu Lys Arg Leu Arg Arg Leu Tyr Cys Asn Val Gly Ile Gly Phe
                80                  85                  90

His Leu Gln Val Leu Pro Asp Gly Arg Ile Gly Gly Val His Ala
                95                  100                 105

Asp Thr Arg Asp Ser Leu Leu Glu Leu Ser Pro Val Gln Arg Gly
                110                 115                 120

Val Val Ser Ile Phe Gly Val Ala Ser Arg Phe Phe Val Ala Met
                125                 130                 135

Ser Ser Arg Gly Lys Leu Phe Gly Val Pro Phe Phe Thr Asp Glu
                140                 145                 150

Cys Lys Phe Lys Glu Ile Leu Leu Pro Asn Asn Tyr Asn Ala Tyr
                155                 160                 165

Glu Ser Tyr Ala Tyr Pro Gly Met Phe Met Ala Leu Ser Lys Asn
                170                 175                 180

Gly Arg Thr Lys Lys Gly Asn Arg Val Ser Pro Thr Met Lys Val
                185                 190                 195

Thr His Phe Leu Pro Arg Leu
                200     202
```

(2) INFORMATION FOR SEQ ID NO:3:

(i) SEQUENCE CHARACTERISTICS:
        (A) LENGTH: 997 base pairs
        (B) TYPE: Nucleic Acid
        (C) STRANDEDNESS: Single
        (D) TOPOLOGY: Circular (xi) SEQUENCE DESCRIPTION: SEQ ID NO:3:

```
CGCGCGCGGC GAGCACGACA TTCCACCGGA CCCGCCGAGC CGCGTCGGGA        50

TAGCCGCTGG CCTCCCGCAC CCCGACCTCC CTCAGCCTCC GCACCTTCGG        100

CTTGTCCCCC CGCGGCCTCC AGTGGGACGG CGTGACCCCG CTCGGGCTCT        150

CAGTGCTCCC GGGGCCGCGC GCCATGGGCA GCCCCCGCTC CGCGCTGAGC        200

TGCCTGCTGT TGCACTTGCT GGTTCTCTGC CTCCAAGCCC AGGTAACTGT        250

TCAGTCCTCA CCTAATTTTA CACAGCATGT GAGGGAGCAG AGCCTGGTGA        300

CGGATCAGCT CAGCCGCCGC CTCATCCGGA CCTACCAGCT CTACAGCCGC        350

ACCAGCGGGA AGCACGTGCA GGTCCTGGCC AACAAGCGCA TCAACGCCAT        400

GGCAGAAGAC GGAGACCCCT TCGCGAAGCT CATTGTGGAG ACCGATACTT        450

TTGGAAGCAG AGTCCGAGTT CGCGGCGCAG AGACAGGTCT CTACATCTGC        500

ATGAACAAGA AGGGGAAGCT AATTGCCAAG AGCAACGGCA AAGGCAAGGA        550

CTGCGTATTC ACAGAGATCG TGCTGGAGAA CAACTACACG GCGCTGCAGA        600

ACGCCAAGTA CGAGGGCTGG TACATGGCCT TTACCCGCAA GGGCCGGCCC        650

CGCAAGGGCT CCAAGACGCG CCAGCATCAG CGCGAGGTGC ACTTCATGAA        700

GCGCCTGCCG CGGGGCCACC ACACCACCGA GCAGAGCCTG CGCTTCGAGT        750

TCCTCAACTA CCCGCCCTTC ACGCGCAGCC TGCGCGGCAG CCAGAGGACT        800

TGGGCCCCGG AGCCCCGATA GGCGCTCGCC CAGCTCCTCC CCACCCAGCC        850

GGCCGAGGAA TCCAGCGGGA GCTCGGCGGC ACAGCAAAGG GGAGGGGCTG        900

GGGAGCTGCC TTCTAGTTGT GCATATTGTT TGCTGTTGGG TTTTTTTGTT        950

TTTTGTTTTT TGTTTTTGTT TTTTGTTTTT TAAACAAAAG AGAGGCG          997
```

(2) INFORMATION FOR SEQ ID NO:4:

(i) SEQUENCE CHARACTERISTICS:
        (A) LENGTH: 215 amino acids
        (B) TYPE: Amino Acid
        (D) TOPOLOGY: Linear (xi) SEQUENCE DESCRIPTION: SEQ ID NO:4:

```
Met Gly Ser Pro Arg Ser Ala Leu Ser Cys Leu Leu His Leu
 1               5                  10                  15

Leu Val Leu Cys Leu Gln Ala Gln Val Thr Val Gln Ser Ser Pro
                20                  25                  30

Asn Phe Thr Gln His Val Arg Glu Gln Ser Leu Val Thr Asp Gln
                35                  40                  45

Leu Ser Arg Arg Leu Ile Arg Thr Tyr Gln Leu Tyr Ser Arg Thr
                50                  55                  60

Ser Gly Lys His Val Gln Val Leu Ala Asn Lys Arg Ile Asn Ala
                65                  70                  75

Met Ala Glu Asp Gly Asp Pro Phe Ala Lys Leu Ile Val Glu Thr
                80                  85                  90

Asp Thr Phe Gly Ser Arg Val Arg Val Arg Gly Ala Glu Thr Gly
                95                  100                 105
```

```
Leu Tyr Ile Cys Met Asn Lys Lys Gly Lys Leu Ile Ala Lys Ser
                110                 115                 120

Asn Gly Lys Gly Lys Asp Cys Val Phe Thr Glu Ile Val Leu Glu
                125                 130                 135

Asn Asn Tyr Thr Ala Leu Gln Asn Ala Lys Tyr Glu Gly Trp Tyr
                140                 145                 150

Met Ala Phe Thr Arg Lys Gly Arg Pro Arg Lys Gly Ser Lys Thr
                155                 160                 165

Arg Gln His Gln Arg Glu Val His Phe Met Lys Arg Leu Pro Arg
                170                 175                 180

Gly His His Thr Thr Glu Gln Ser Leu Arg Phe Glu Phe Leu Asn
                185                 190                 195

Tyr Pro Pro Phe Thr Arg Ser Leu Arg Gly Ser Gln Arg Thr Trp
                200                 205                 210

Ala Pro Glu Pro Arg
                215

(2) INFORMATION FOR SEQ ID NO:5:

(i) SEQUENCE CHARACTERISTICS:
        (A) LENGTH: 1314 base pairs
        (B) TYPE: Nucleic Acid
        (C) STRANDEDNESS: Single
        (D) TOPOLOGY: Linear (xi) SEQUENCE DESCRIPTION: SEQ ID NO:5:

ATGCTGCTGC TGCTGGCCAG ATGTTTTCTG GTGATCCTTG CTTCCTCGCT                50

GCTGGTGTGC CCCGGGCTGG CCTGTGGGCC CGGCAGGGGG TTTGGAAAGA               100

GGCGGCACCC CAAAAAGCTG ACCCCTTTAG CCTACAAGCA GTTTATTCCC               150

AACGTAGCCG AGAAGACCCT AGGGGCCAGC GGCAGATATG AAGGGAAGAT               200

CACAAGAAAC TCCGAACGAT TTAAGGAACT CACCCCCAAT TACAACCCCG               250

ACATCATATT TAAGGATGAG GAAAACACGG GAGCAGACCG GCTGATGACT               300

CAGAGGTGCA AAGACAAGTT AAATGCCTTG GCCATCTCTG TGATGAACCA               350

GTGGCCTGGA GTGAAGCTGC GAGTGACCGA GGGCTGGGAT GAGGACGGCC               400

ATCATTCAGA GGAGTCTCTA CACTATGAGG GTCGAGCAGT GGACATCACC               450

ACGTCCGACC GGGACCGCAG CAAGTACGGC ATGCTGGCTC GCCTGGCTGT               500

GGAAGCAGGT TTCGACTGGG TCTACTATGA ATCCAAAGCT CACATCCACT               550

GTTCTGTGAA AGCAGAGAAC TCCGTGGCGG CCAAATCCGG CGGCTGTTTC               600

CCGGGATCCG CCACCGTGCA CCTGGAGCAG GGCGGCACCA AGCTGGTGAA               650

GGACTTACGT CCCGGAGACC GCGTGCTGGC GGCTGACGAC CAGGGCCGGC               700

TGCTGTACAG CGACTTCCTC ACCTTCCTGG ACCGCGACGA AGGCGCCAAG               750

AAGGTCTTCT ACGTGATCGA GACGCTGGAG CCGCGCGAGC GCCTGCTGCT               800

CACCGCCGCG CACCTGCTCT TCGTGGCGCC GCACAACGAC TCGGGGCCCA               850

CGCCCGGGCC AAGCGCGCTC TTTGCCAGCC GCGTGCGCCC CGGGCAGCGC               900

GTGTACGTGG TGGCTGAACG CGGCGGGGAC CGCCGGCTGC TGCCCGCCGC               950

GGTGCACAGC GTGACGCTGC GAGAGGAGGA GGCGGGCGCG TACGCGCCGC              1000

TCACGGCGCA CGGCACCATT CTCATCAACC GGGTGCTCGC CTCGTGCTAC              1050

GCTGTCATCG AGGAGCACAG CTGGGCACAC CGGGCCTTCG CGCCTTTCCG              1100
```

```
CCTGGCGCAC GCGCTGCTGG CCGCGCTGGC ACCCGCCCGC ACGGACGGCG      1150

GGGGCGGGGG CAGCATCCCT GCAGCGCAAT CTGCAACGGA AGCGAGGGGC      1200

GCGGAGCCGA CTGCGGGCAT CCACTGGTAC TCGCAGCTGC TCTACCACAT      1250

TGGCACCTGG CTGTTGGACA GCGAGACCAT GCATCCCTTG GGAATGGCGG      1300

TCAAGTCCAG CTGA                                             1314

(2) INFORMATION FOR SEQ ID NO:6:

(i) SEQUENCE CHARACTERISTICS:
        (A) LENGTH: 437 amino acids
        (B) TYPE: Amino Acid
        (D) TOPOLOGY: Linear (xi) SEQUENCE DESCRIPTION: SEQ ID NO:6:

Met Leu Leu Leu Leu Ala Arg Cys Phe Leu Val Ile Leu Ala Ser
 1               5                  10                  15

Ser Leu Leu Val Cys Pro Gly Leu Ala Cys Gly Pro Gly Arg Gly
                20                  25                  30

Phe Gly Lys Arg Arg His Pro Lys Lys Leu Thr Pro Leu Ala Tyr
                35                  40                  45

Lys Gln Phe Ile Pro Asn Val Ala Glu Lys Thr Leu Gly Ala Ser
                50                  55                  60

Gly Arg Tyr Glu Gly Lys Ile Thr Arg Asn Ser Glu Arg Phe Lys
                65                  70                  75

Glu Leu Thr Pro Asn Tyr Asn Pro Asp Ile Ile Phe Lys Asp Glu
                80                  85                  90

Glu Asn Thr Gly Ala Asp Arg Leu Met Thr Gln Arg Cys Lys Asp
                95                 100                 105

Lys Leu Asn Ala Leu Ala Ile Ser Val Met Asn Gln Trp Pro Gly
               110                 115                 120

Val Lys Leu Arg Val Thr Glu Gly Trp Asp Glu Asp Gly His His
               125                 130                 135

Ser Glu Glu Ser Leu His Tyr Glu Gly Arg Ala Val Asp Ile Thr
               140                 145                 150

Thr Ser Asp Arg Asp Arg Ser Lys Tyr Gly Met Leu Ala Arg Leu
               155                 160                 165

Ala Val Glu Ala Gly Phe Asp Trp Val Tyr Tyr Glu Ser Lys Ala
               170                 175                 180

His Ile His Cys Ser Val Lys Ala Glu Asn Ser Val Ala Ala Lys
               185                 190                 195

Ser Gly Gly Cys Phe Pro Gly Ser Ala Thr Val His Leu Glu Gln
               200                 205                 210

Gly Gly Thr Lys Leu Val Lys Asp Leu Arg Pro Gly Asp Arg Val
               215                 220                 225

Leu Ala Ala Asp Asp Gln Gly Arg Leu Leu Tyr Ser Asp Phe Leu
               230                 235                 240

Thr Phe Leu Asp Arg Asp Glu Gly Ala Lys Lys Val Phe Tyr Val
               245                 250                 255

Ile Glu Thr Leu Glu Pro Arg Glu Arg Leu Leu Leu Thr Ala Ala
               260                 265                 270

His Leu Leu Phe Val Ala Pro His Asn Asp Ser Gly Pro Thr Pro
               275                 280                 285

Gly Pro Ser Ala Leu Phe Ala Ser Arg Val Arg Pro Gly Gln Arg
               290                 295                 300
```

```
Val Tyr Val Val Ala Glu Arg Gly Gly Asp Arg Arg Leu Leu Pro
        305                 310                 315

Ala Ala Val His Ser Val Thr Leu Arg Glu Glu Glu Ala Gly Ala
        320                 325                 330

Tyr Ala Pro Leu Thr Ala His Gly Thr Ile Leu Ile Asn Arg Val
        335                 340                 345

Leu Ala Ser Cys Tyr Ala Val Ile Glu Glu His Ser Trp Ala His
        350                 355                 360

Arg Ala Phe Ala Pro Phe Arg Leu Ala His Ala Leu Leu Ala Ala
        365                 370                 375

Leu Ala Pro Ala Arg Thr Asp Gly Gly Gly Gly Ser Ile Pro
        380                 385                 390

Ala Ala Gln Ser Ala Thr Glu Ala Arg Gly Ala Glu Pro Thr Ala
        395                 400                 405

Gly Ile His Trp Tyr Ser Gln Leu Leu Tyr His Ile Gly Thr Trp
        410                 415                 420

Leu Leu Asp Ser Glu Thr Met His Pro Leu Gly Met Ala Val Lys
        425                 430                 435

Ser Ser
437

(2) INFORMATION FOR SEQ ID NO:7:

(i) SEQUENCE CHARACTERISTICS:
        (A) LENGTH: 1383 base pairs
        (B) TYPE: Nucleic Acid
        (C) STRANDEDNESS: Single
        (D) TOPOLOGY: Circular (xi) SEQUENCE DESCRIPTION: SEQ ID NO:7:

ATGTGCCGAG GCTTCTCTTT CAGGCACTTG CTGCCGCTGC TGCTCCTGCA          50

GCTGTCAAAA CTCCTAGTTG TCACCCAAGG AAAGACCGTG GTGCTGGGGA         100

AGGAAGGGGG TTCAGCAGAA CTGCCCTGTG AAAGTACCTC GAGGAGGAGT         150

GCATCCTTCG CGTGGAAGTC CTCTGACCAA AGACAATTC  TGGGATATAA         200

GAACAAGTTA TTGATTAAAG GTTCACTTGA GCTGTATAGT CGTTTTGATT         250

CCAGAAAAAA TGCATGGGAG AGAGGATCAT TTCCCCTCAT CATCAATAAA         300

CTTAGGATGG AGGACTCTCA GACTTATGTC TGCGAGCTGG AGAACAAGAA         350

AGAGGAGGTG GAGTTGTGGG TCTTCAGAGT GACCTTCAAT CCGGGTACCA         400

GACTGTTGCA GGGGCAGAGC CTGACCCTGA TCTTGGATAG CAACCCTAAG         450

GTCTCTGACC CCCCGATAGA GTGCAAACAC AAAAGCAGTA ACATTGTCAA         500

GGACTCCAAA GCTTTCTCCA CGCACAGCCT AAGGATTCAG ACAGTGGCA          550

TCTGGAACTG CACCGTGACC CTGAACCAGA AGAAGCACTC ATTTGACATG         600

AAACTCTCAG TGCTGGGCTT TGCGGTCGAC AAGAAAATTG TGCCAAGGGA         650

ATGCAATCCT TGTGGATGTA CAGGCTCAGA AGTATCATCT GTCTTCATCT         700

TCCCCCCAAA GACCAAAGAT GTGCTCACCA TCACTCTGAC TCCTAAGGTC         750

ACGTGTGTTG TGGTAGACAT TAGCCAGAAT GATCCCGAGG TCCGGTTCAG         800

CTGGTTTATA GATGACGTGG AAGTCCACAC AGCTCAGACT CATGCCCCGG         850

AGAAGCAGTC CAACAGCACT TTACGCTCAG TCAGTGAACT CCCCATCGTG         900

CACCGGGACT GGCTCAATGG CAAGACGTTC AAATGCAAAG TCAACAGTGG         950
```

| AGCATTCCCT GCCCCCATCG AGAAAAGCAT CTCCAAACCC GAAGGCACAC | 1000 |
| --- | --- |
| CACGAGGTCC ACAGGTATAC ACCATGGCGC CTCCCAAGGA AGAGATGACC | 1050 |
| CAGAGTCAAG TCAGTATCAC CTGCATGGTA AAAGGCTTCT ATCCCCCAGA | 1100 |
| CATTTATACG GAGTGGAAGA TGAACGGGCA GCCACAGGAA AACTACAAGA | 1150 |
| ACACTCCACC TACGATGGAC ACAGATGGGA GTTACTTCCT CTACAGCAAG | 1200 |
| CTCAATGTAA AGAAAGAAAC ATGGCAGCAG GGAAACACTT TCACGTGTTC | 1250 |
| TGTGCTGCAT GAGGGCCTGC ACAACCACCA TACTGAGAAG AGTCTCTCCC | 1300 |
| ACTCTCCTGG TAAATGACCC AGAGAATTCA ATCGATGGCC GCCATGGCCC | 1350 |
| AACTTGTTTA TTGCAGCTTA TAATGGTTAC AAA | 1383 |

(2) INFORMATION FOR SEQ ID NO:8:

(i) SEQUENCE CHARACTERISTICS:
        (A) LENGTH: 1983 base pairs
        (B) TYPE: Nucleic Acid
        (C) STRANDEDNESS: Single
        (D) TOPOLOGY: Circular (xi) SEQUENCE DESCRIPTION: SEQ ID NO:8:

| ATGTGGGGCT GGAAGTGCCT CCTCTTCTGG GCTGTGCTGG TCACAGCCAC | 50 |
| --- | --- |
| TCTCTGCACT GCCAGGCCAG CCCCAACCTT GCCCGAACAA GCTCAGCCCT | 100 |
| GGGGAGTCCC TGTGGAAGTG GAGTCCCTCC TGGTCCACCC TGGCGACCTG | 150 |
| CTACAGCTTC GCTGTCGGCT TCGCGATGAT GTGCAGAGCA TCAACTGGCT | 200 |
| GCGGGATGGG GTGCAGCTGG TGGAGAGCAA CCGTACCCGC ATCACAGGGG | 250 |
| AGGAGGTGGA GGTGCGGGAC TCCATCCCCG CTGACTCTGG CCTCTACGCT | 300 |
| TGCGTGACCA GCAGCCCCTC TGGCAGCGAT ACCACCTACT TCTCCGTCAA | 350 |
| TGTCTCAGAT GCACTCCCAT CCTCGGAAGA TGATGACGAC GACGATGACT | 400 |
| CCTCCTCGGA GGAGAAAGAG ACGGACAACA CCAAACCAAA CCCTGTAGCT | 450 |
| CCCTACTGGA CATCCCCAGA GAAAATGGAG AAGAAACTGC ATGCGGTGCC | 500 |
| CGCTGCCAAG ACGGTGAAGT TCAAGTGCCC GTCGAGTGGG ACACCCAACC | 550 |
| CCACTCTGCG CTGGTTGAAA ATGGCAAAG AGTTTAAGCC TGACCACCGA | 600 |
| ATTGGAGGCT ACAAGGTTCG CTATGCCACC TGGAGCATCA TAATGGATTC | 650 |
| TGTGGTGCCT TCTGACAAGG GCAACTACAC CTGCATCGTG GAGAATGAGT | 700 |
| ATGGGAGCAT CAACCACACC TACCAGCTTG ACGTCGTGGA ACGATCTCCG | 750 |
| CACCGACCCA TCCTTCAGGC AGGGCTGCCT GCCAACAAGA CAGTGGCCCT | 800 |
| GGGCAGCAAT GTGGAGTTCA TGTGTAAGGT GTACAGCGAT CCGCAGCCTC | 850 |
| ACATTCAGTG GCTGAAGCAC ATCGAGGTGA ACGGGAGTAA GATCGGGCCA | 900 |
| GACAACTTGC CGTATGTCCA GATCCTGAAG ACTGCTGGAG TTAATACCAC | 950 |
| CGACAAGGAA ATGGAGGTGC TTCATCTACG GAATGTCTCC TTTGAGGATG | 1000 |
| CGGGGGAGTA TACGTGCTTG GCGGGTAACT CTATCGGACT CTCCCATCAC | 1050 |
| TCTGCATGGT TGACCGTTCT GGAAGCCCTG GAAGAGAGAC CAGCTGTGAT | 1100 |
| GACCTCACCG CTCTACGTCG ACAAGAAAAT TGTGCCAAGG GAATGCAATC | 1150 |
| CTTGTGGATG TACAGGCTCA GAAGTATCAT CTGTCTTCAT CTTCCCCCCA | 1200 |
| AAGACCAAAG ATGTGCTCAC CATCACTCTG ACTCCTAAGG TCACGTGTGT | 1250 |

-continued

```
TGTGGTAGAC ATTAGCCAGA ATGATCCCGA GGTCCGGTTC AGCTGGTTTA        1300

TAGATGACGT GGAAGTCCAC ACAGCTCAGA CTCATGCCCC GGAGAAGCAG        1350

TCCAACAGCA CTTTACGCTC AGTCAGTGAA CTCCCCATCG TGCACCGGGA        1400

CTGGCTCAAT GGCAAGACGT TCAAATGCAA AGTCAACAGT GGAGCATTCC        1450

CTGCCCCCAT CGAGAAAAGC ATCTCCAAAC CCGAAGGCAC ACCACGAGGT        1500

CCACAGGTAT ACACCATGGC GCCTCCCAAG GAAGAGATGA CCCAGAGTCA        1550

AGTCAGTATC ACCTGCATGG TAAAAGGCTT CTATCCCCCA GACATTTATA        1600

CGGAGTGGAA GATGAACGGG CAGCCACAGG AAAACTACAA GAACACTCCA        1650

CCTACGATGG ACACAGATGG GAGTTACTTC CTCTACAGCA AGCTCAATGT        1700

AAAGAAAGAA ACATGGCAGC AGGGAAACAC TTTCACGTGT TCTGTGCTGC        1750

ATGAGGGCCT GCACAACCAC CATACTGAGA AGAGTCTCTC CCACTCTCCT        1800

GGTAAATGAC CCAGAGAATT CAATCGATGG CCGCCATGGC CCAACTTGTT        1850

TATTGCAGCT TATAATGGTT ACAAATAAAG CAATAGCATC ACAAATTTCA        1900

CAAATAAAGC ATTTTTTTCA CTGCATTCTA GTTGTGGTTT GTCCAAACTC        1950

ATCAATGTAT CTTATCATGT CTGGATCGAT CGG                          1983
```

METHOD OF DOPAMINERGIC AND SEROTONERGIC NEURON FORMATION FROM NEUROPROGENITOR CELLS

BACKGROUND

The present invention relates to neuronal formation and methods of treating diseases characterized by abnormalities in and the activity of dopaminergic (DA) and serotonergic (5HT) neurons.

The vertebrate nervous system is composed of multiple neuronal and non-neuronal cell types which develop in stereotypic positions along the dorso-ventral (D-V) and anterior-posterior (A-P) axes of the early neural tube. The mechanisms controlling this process, which is essential for subsequent formation of functional neural networks, are not fully understood (reviewed in Lumsden and Krumlauf, (1996) Science 274: 1109–1114; Tanabe and Jessell, (1996) Science 274: 1115–1123. However, it has been proposed that signaling centers which operate along the two main axes of this system establish an epigenetic grid of Cartesian coordinates, and that neural progenitors assess their location on this grid, assuming distinct cell fates accordingly (e.g. Wolpert, (1969) J. Theor. Biol. 25: 1–47; Rubenstein et al., (1994) Science 266: 578–80.

Consistent with the epigenetic grid hypothesis, grafting experiments have epeatedly demonstrated that vertebrate neural progenitors are not genetically pre-determined, but instead can acquire new stereotypic identities if moved to ectopic locations in the neural plate (Alvarado-Mallartet al., (1990) Develop. Biol. 139: 75–88; Gardner and Barald, (1991) Develop. 113: 1037–1048; Grapin-Botton et al., Develop. 124: 849–859 (1997); Itasaki et al. (1996) Neuron 16: 487–500; Simon et al. (1995) Current Biol. 5: 205–214. In addition, transplantation, as well as explant culture studies have confirmed the existence of signaling centers which can change the fate of juxtaposed neural progenitors. Thus, signaling centers such as the dorsal ectodermal epidermis, roof plate, floor plate and notochord have been shown to instruct cell fates along the D-V axis [reviewed in Tanabe and Jessell (1996) Science 274: 1115–1123; Liem et al. (1997) Cell 91: 127–138] whereas signaling centers located in the prechordal plate, paraxial mesoderm, somitic mesoderm, mid-hindbrain boundary (isthmus) and the anterior neural plate [reviewed in Lumsden and Krumlauf (1996) Science 274: 1109–1114; Dale et al. (1997) Cell 90: 257–269; Foley et al. (1997) Develop. 124: 2983–2996; Grapil-Botton et al. (1997 supra; Muhr et al. (1997) Neuron 19: 487–502; Itasaki et al. (1996) Neuron 16: 487–500; Shimamura and Rubenstein, (1997) Develop. 124: 2709–2718; Houart et al., (1998) Nature 391: 788–792] can change cell fate along the A-P axis of the neural tube. Finally, in agreement with the notion that the information grids are established by extra-cellular molecules, a number of secreted proteins and chemicals were shown to modify the fate of neural plate cells in a characteristic fashion. Thus, Sonic hedgehog and BMP proteins were shown to influence cell fate along the D-V axis (reviewed in Tanabe and Jessell (1996), supra; Liem et al. (1997) Cell 91: 127–138, whereas FGF2, FGF8, retinoic acid and Wnt1 can change cell fate along the A-P axis [reviewed in Lumsden and Krumlauf (1996), supra; Crossley et al. (1996) Nature 380: 66–68; Shimamura and Rubenstein (1997), supra.].

Serotonergic neurons are concentrated in the ventral and ventro-lateral aspects of the hindbrain and innervate most parts of the central nervous system including the cerebral cortex, limbic system and spinal cord. These neurons control levels of awareness, arousal, behavioral traits and food intake, and their abnormal function has been linked to aggression, depression and schizophrenia (Jacobs and Gelperin (1981) Serotonin Neurotransmission and Behavior. The MIT Press, Cambridge, Mass.). Serotonergic neurons important in regulation of food intake, hormone secretion, responses to stress, pain and immune function. Serotonergic neurons innervate nearly every area of the central nervous system, including the cerebral cortex, limbic system and spinal cord, and can influence multiple functions of the brain, such as behavior, appetite, pain, sexual activity, cardiovascular function, hormone secretion, and temperature regulation. Serotonergic dysfunction likely to play roles in the pathophysiology of various psychiatric, neurologic, and other diseases. For example, mental depression, Asberg et al., J. Clin. Psychiatry 47(4): 23–35 (1986), suicide, Asberg et al., supra, Lester, D., Pharmocopsychiatry 28(2): 45–50 (1995), and violent aggressive behavior, Brown et al., J. Clin. Psychiatry 54(4): 31–41 (1990), Eichelman, B. S., Annu. Rev. Med. 41: 149–158 (1990). Serotonin uptake inhibitors have been used in the treatment of mental depression, obsessive-compulsive disorder and bulimia. Fuller, R. W., "Serotonin uptake inhibitors: Uses in clinical therapy and in laboratory research," Progress in Drug Research 45: 167–204, Birkhäuser-Varlag, Basel (1995). As serotonergic neurons innervate cerebral blood flow, serotonin receptor agonists, such Sumatriptan, have been employed to abort migraine attacks. Plosker, G. L. et al. Drugs 94(4): 622–651 (1994). Most of the known and cloned serotonin receptors belong to a G-protein-coupled superfamily of receptors having seven membrane-spanning domains. Hoyer et al., Pharmacol. Rev. 46(2): 157–203 (1994). Some seratonin receptor subtypes couple negatively to adenylate cyclase, while others couple positively, while others are coupled to activation of phospholipase C, or ligand-gated ion channels. Fuller, R. W., Ann. N.Y. Acad. Sci. 780: 176–184 (1996).

Dopaminergic (DA) neurons, which reside in the ventral and ventro-lateral aspects of the midbrain, control postural reflexes, movement and reward-associated behaviors. DA neurons develop in the vicinity of the floor plate and are induced by contact-mediation. These neurons innervate multiple structures in the forebrain, and their degeneration or abnormal function is associated with Parkinson's disease, schizophrenia and drug addiction. Hynes et al., Cell 80: 95–101 (1995).

DA neurons located in the substantia nigra have a great impact upon striatal activity as bilateral lesions of the nigrostriatal pathway produce a syndrome in experimental animals that is quite similar to the observed motor dysfunctions observed in Parkinson's disease: resting tremor, rigidity, akinesia and postural abnormalities. Bilateral lesions of the nigrostriatal pathway caused by 6-hydroxydopamine (OHDA) caused profound akinesia, adipsia, aphagia and sensory neglect in rodents, Ungerstedt, U. Acta Physiol. Scand. 1971 (Suppl. 367): 95–121; Yirek and Sladek, 1990, Annu. Rev. Neurosci. 13: 415–440.

Loss of striatal DA is associated with an alternation in the number of target receptors located on striatal cells. In parkinsonism, changes in the status of DA receptors may be dependent on the stage of progression of the disease. The hallmark of parkinsonism is a severe reduction of dopamine in all components of the basal ganglia, Hornykiewicz, O., 1988, Mt. Sinai J. Med. 55: 11–20. Dopamine and its metabolites are depleted in the caudate nucleus, putamen, globus pallidus and pars compacta of the substantia nigra. Moderate losses of DA are found in the nucleus accumbens, lateral hypothalamus, medial olfactory region, and amygdaloid accumbens. Changes in non dopaminergic neuronal systems include decreases in tissue concentrations of norepinephrine, serotonin, substance P, neurotension and several neuropeptides in most basal gangliar structure, cerebellar cortex, and spinal cord.

Considerable attention has been placed on neural transplantation in patients afflicted with Parkinson's disease. These clinical experiments essentially evolved from basic scientific research using various animal models of parkinsonism as recipients of either fetal embryonic nerve cell or paraneuronal tissue grafts to brain-damaged areas. While the concept for neural transplantation is quite old, major advances have occurred only within the last two decades, and many issues remain such as the potential long-term effectiveness of neural grafts to restore and maintain normalized function in animal models of a variety of disorders. Animal experimentation with fetal DA nerve cell grafts have provided encouragement that such grafts could reverse DA deficits and restore motor function in animals with experimental lesions of the nigrostriatal DA system. However numerous ethical, legal and safety issues are coincident with the use of fetal tissue in clinical research, factors which have only exacerbated an already limited supply, all of which establishes an urgent need for alternative sources of dopaminergic neurons.

Schizophrenia is often characterized by peculiar thought disorders, a disturbance of emotional or affective responses to the environment and autism—a withdrawal from interactions with other people. Hallucinations have also been associated as symptomatic of schizophrenia. Phenothiazine drugs are generally acknowledged to be effective in alleviating the symptoms of schizophrenia. Other medications have involved neurotransmitters. Snyder et al., *Science* 184:1243–1253 (1974). Extended use of and toxic doses of amphetamines also elicit schizophrenic-like symptoms.

Despite the evidence for the existence of positional cues [e.g., Shh, FGF4 and FGF8 are known to be expressed in combination during node and limb bud development. Bueno et al., *Develop. Dynam.* 207: 291–299 (1996)], there has still been no direct demonstration that two molecularly defined, secreted, physiological signals operate along the A-P and D-V axes respectively, which determine the location and phenotype of a particular neuronal cell type in the neural tube.

Applicants demonstrate herein, that DA neurons in fact, develop at sites where the signals of two distinct molecules, Shh and FGF8, intersect, and that these two extracellular inducers are necessary and sufficient to define the location of DA neurons along the D-V and A-P axes of the anterior neural tube. Progenitors for rostral hindbrain serotonergic neurons appear to use the same intersection as a landmark for specification, but assume a distinct identity because their response to Shh and FGF8 is modified by FGF4.

SUMMARY

In one embodiment, the invention relates to method of forming dopaminergic neurons in vitro by contacting neuroprogenitor cells to an effective amount of FGF-8 and sonic hedgehog (Shh). In one aspect, the invention relates to a method of forming serotonergic neurons in vitro by contacting neuroprogenitor cells to an effective amount of FGF-4, FGF-8 and Shh. In yet another aspect, the method of forming serotonergic neurons comprises an exposure of neuroprogenitor cells to FGF-4 prior to exposure to FGF-8 and Shh. In yet another aspect, the invention relates to a method of using a functional fragment of Shh, (e.g., N-terminal amino acid residues 1–195 of FIG. 11). In yet another aspect, the invention relates to a method of using the FGF-4, FGF-8 and Shh proteins encoded by SEQ ID NO: 2 (FIG. 9), SEQ ID NO: 4 (FIG. 10) and SEQ ID NO: 6 (FIG. 11), respectively.

In another embodiment, the invention relates to a method of treating a disorder characterized by degeneration of dopaminergic neurons by transplantation of a therapeutically effective amount of neuroprogenitor cells which have been pretreated with effective amounts of FGF-8 and Shh. In another embodiment, the invention relates to method of treating a disorder characterized by degeneration of serotonergic neurons by transplantation of neuroprogenitor cells which have been pretreated with effective amounts of FGF-4, FGF-8 and Shh.

In another embodiment, the invention also relates to a method of using scrotonergic neurons for the treatment of disorders which are characterized by abnormalities in the regulation of food intake, hormone secretion, stress response, pain and immune function, sexual activity, cardiovascular function and temperature regulation. In particular, the method includes various psychiatric, neurologic and other diseases, e.g., mental depression, proclivity to suicide, violent aggressive behavior, obsessive-compulsive behavior and anorexia/bulimia and schizophrenia.

In another embodiment, the invention also relates to a method of using dopaminergic neurons for the treatment of disorders which are characterized by abnormalities in the regulation of postural reflexes, movement and reward-associated behaviors. In particular, the method includes Parkinson's disease, schizophrenia and drug addiction. Additionally, lesions to due trauma or other illness which result in Parkinson-like conditions such as resting tremor, rigidity, akinesia and postural abnormality, including akinesia, adipsia, aphagia and sensory neglect.

In another embodiment, the method of the present invention also relates to the coadministration of one or more neuronal survival factors in conjunction with Shh, FGF4, FGF8. In one aspect, the neuronal survival factor may be administered before exposure to Shh, FGF-4 or FGF-8 of the neuroprogenitor cells in culture or concurrent therewith. In another aspect, the neuronal survival factors may also be administered with the transplant of the neuroprogenitor cells themselves. For example, nerve growth factor (NGF), ciliary neurotrophic factor (CNTF), brain derived neurotrophic factor (BDNF), neurotrophin-3 (NT-3), neurotrophin-4 (NT-4), aFGF, IL-1β, TNFα, insulin-like growth factor (IGF-1, IGF-2), transforming growth factor beta (TGF-β, TGF-β1) or skeletal muscle extract.

In yet another embodiment, the invention relates to a cell culture composition comprising neuroprogenitor cells and an effective amount of FGF-8 and Shh to stimulate differentiation into dopaminergic neurons. In another embodiment, the cell culture composition comprises neuroprogenitor cells and an effective amount of FGF-4, FGF-8 and Shh to stimulate differentiation into serotonergic neurons.

In yet another embodiment, the invention relates to a medical device comprising neuroprogenitor cells and a means for releasing effective amounts of FGF-8 and Shh to stimulate differentiation into dopaminergic neurons. In another embodiment, the medical device comprises neuroprogenitor cells and effective amounts of FGF-4, FGF-8 and Shh to stimulate differentiation of neuroprogenitor cells into dopaminergic neurons.

In yet another embodiment, the invention relates to composition comprising a pharmaceutically-acceptable carrier and an effective amount of FGF-8 and Shh to stimulate differentiation of neuroprogenitor cells into dopaminergic neurons. In another embodiment, the composition comprises a pharmaceutically-acceptable carrier and an effective amount of FGF-4, FGF-8 and Shh to stimulate differentiation of neuroprogen itor cells into serotonergic neurons.

Other aspects of the invention will become apparent from the following detailed description and the claims.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIGS. 1A–G depict photomicrographs showing the location of early gene Markers and mature neurons in the early embryo. Slides (A–C) are parasaggital sections of the E14 rat ventral mid/hindbrain. Slide (A) is an in situ hybridization with Fgf8 (purple) and Shh (red). Slide (B) is an in situ hybridization with Fgf8 (light purple) and immunohistochemical stained for TH (tyrosine hydroxylase, the rate limiting enzyme in dopamine synthesis) (red). Slide (C) is an immunohistochemical stain for TH (dopaminergic neurons) (red) and 5HT (serotonergic neurons) (green). The arrows mark the mid/hindbrain boundary and the site of Fgf8 expression. $TH^+$ neurons are confined to the rostral side of the isthmus and 5HT neurons to the caudal side (in C, 5HT axons are seen crossing the $TH^+$ neuronal domain).

Figures 3A, 3B, 3C, 3D:
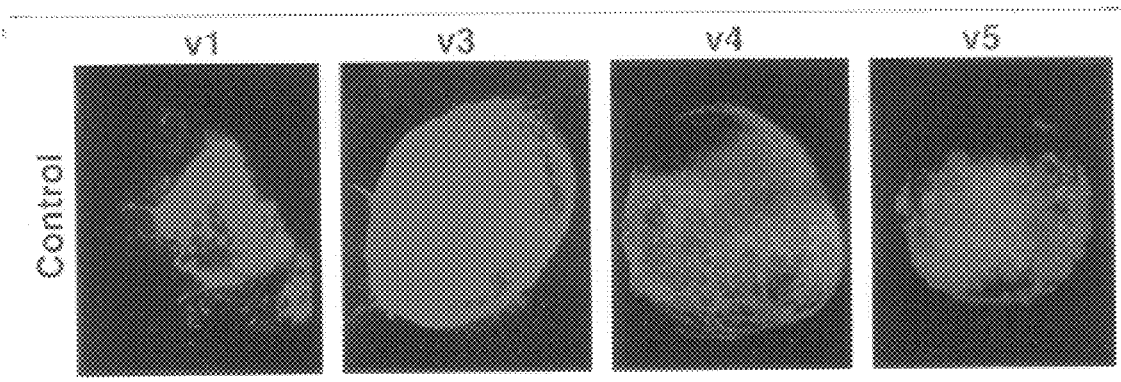

Slides (D, E) are 6 somite stage rat embryos in situ hybridized for Fgf8 (purple) (D, side view), or Shh (purple) (E, ventral view). The red lines represent transection sites. The numbers represent the presumptive rostral forebrain (1), caudal forebrain (2), midbrain (3), and hindbrain (4–6). The boundary between 3 and 4 is the rhombic isthmus. (d=presumptive dorsal, v=presumptive ventral). Slide (F) is an in situ hybridization of Fgf8 (purple) and Shh (red) to an E13 rat ventral mid/hindbrain explant. Slide (G) depicts E9 explants dissected as outlined in (D, E) that were in siti hybridized to Fgf8 (purple) (top row). Ventral explants v1–v6 were cultured in collagen gel for 36 hours and then stained for Shh (green) (middle row), or for 6 days and then double immunostained for both TH (red) and 5HT (green) (bottom row).

In FIG. 1, 25 explants were examined for each region. PS: primitive streak. ANR: anterior neural ridge. IC: intraembryonic coelom. Broken white lines in G outline the explants. Anterior is to the left, posterior to the right. Scale bar represents 500 µm in A, 250 µm in B and C, 80 µm in D, 60 µm in E and G middle row, 200 µm in F, 40 µm in G top row, 120 µm in G bottom row.

FIGS. 2A–F are photomicrograph showing ectopic induction of $TH^+$ neurons by the floorplate and isthmus. Slide (A) is a 6 somite E9 rat dorsal explant encompassing the forebrain, metencephalon and metencephalon (d1–4) was cultured in collagen gel for 6 days and stained for TH (red) and FP4 (green). Neither $TH^+$ DA neurons nor $FP4^+$ floorplate cells were detected (n>0/10). Slide (B) depicts E9 rat dorso-rostral forebrain explant (d1) that was co-cultured with a floorplate explant (fp, green FP4 staining) taken from E13 rat spinal cord. $TH^+$ neurons (red) were induced in d1 by the floorplate. (n=11/12 $TH^+$). Slide(C) isan E9 ratdorsal mes/metencephalicexplant(d3/4)that was co-cultured with a floorplate explant. $TH^+$ neurons (red) were induced by the floorplate (n=9/11 $TH^+$). Slides (D–F) show ectopic induction of DA neurons by isthmus. Depicted are a 6 somite E9 rat ventro-caudal forebrain explant v2 (D, n=0/14<10 $TH^+$ neurons/explant), or rhombic isthmus explant taken from 10 somite E2 chick embryos (E, n=0/13), were cultured alone, or in combination (F, n=17/18 $TH^+$), for 6 days, and stained for TH (red), and chick-specific neuronal marker L1 (green). $TH^+$ DA neurons were ectopically induced (>100 $TH^+$ neurons/explant) in v2 by the chick isthmus. Broken white lines in A and D outline the explants. Scale bar=200 µm.

FIGS. 3A–L are photomicrographs showing the dependency of the differentiation of DA and 5HT on the presence of Shh. Ventral, 6 somite rostral forebrain explants v1 (A, E, I), midbrain explants v3 (B, F, J), rostral hindbrain explants v4 (C, G, K), or caudal hindbrain explants v5 (D, H, L) were cultured in collagen gel for 6 days either: in control medium (top row, A, B, C, D); with Shh function blocking antibody added at day 0 (middle row, E, F, G, H); or with Shh function blocking antibody added at day 2 (bottom row, I, J, K, L). All explants in columns 1 and 2 (A, E, I, B, F, J) were stained for TH (red). Explants in columns 3 and 4 (C, G, K, D, H, L) were stained for 5HT (green). (A: n=8/8, B:n=14/15, C:n=14/14, D:n=17/17, E:n=0/6, F:n=1/12, G:n=0/16, H:n=1/24, I:n=0/7, J:n=10/11, K:n=0/13, L:n=9/25 less than 50 $5HT^+$ positive neurons/explant). Broken white lines mark the negative explants. Scale bar=120 µm.

FIGS. 4A–H are photomicrographs depicting the inhibition of midbrain DA and rostral hindbrain 5HT neurons by recombinant soluble high affinity FGF-8 blocking antibodies (FGFR3-IgG). $TH^+$ (red) and $5HT^+$ (green) neurons develop normally in 6 somite stage explants v3/4 that were crown for 6 days in the presence of FGFR1-IgG (recombinant soluble low affinity blocking antibody which binds to FGF-1,2,4,5 and 6 but not 8). Both neuron types appeared to develop normally when FGFR1-IgG was applied at day 0 (A, n=21/23), but fail to develop in the presence of FGFR3-IgG applied at day 0 (B, n=2/22), or decrease in number when exposed to FGFR3-IgG applied after 1 day in culture (C, n=12/14). FGFR3-IgG failed to block the development of $TH^+$ and $5HT^+$ neurons when applied after 2 days in culture (D, n=7/7). β-tubulin$^+$ neurons (green) readily appear in explants v3/4 that were grown for 6 days in the presence of FGFR3-IgG (E, n=16/16). FGFR3-IgG failed to block the development of $5HT^+$ neurons in caudal hindbrain explants (explant v5) when applied at day 0 in culture (F, n=11/13). HNF3β$^+$ (red) and FP4$^+$ (green) cells develop in explants v3/4 in the presence of CD4-IgG applied at day 0 (G, n=6/6), or FGFR3-IgG added at day 0 (H, n=6/6). Broken white lines in B, G and H mark the explants. Scale bar represents 180 µm.

Figure 5A:
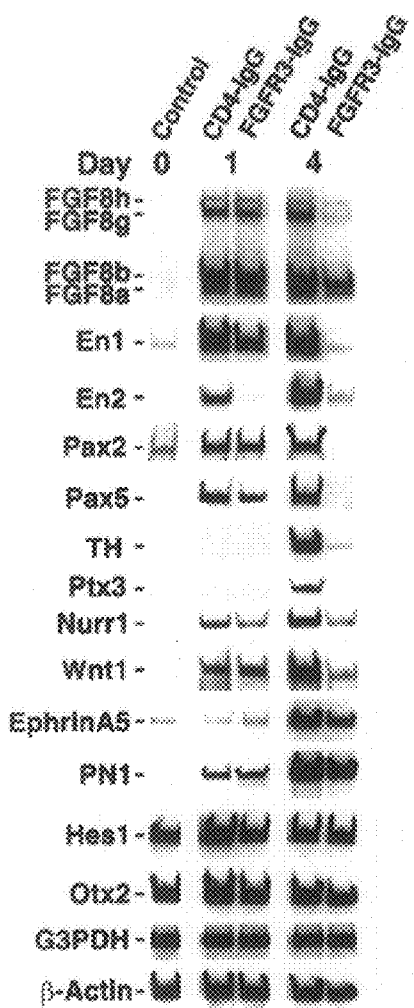
Figure 5B:
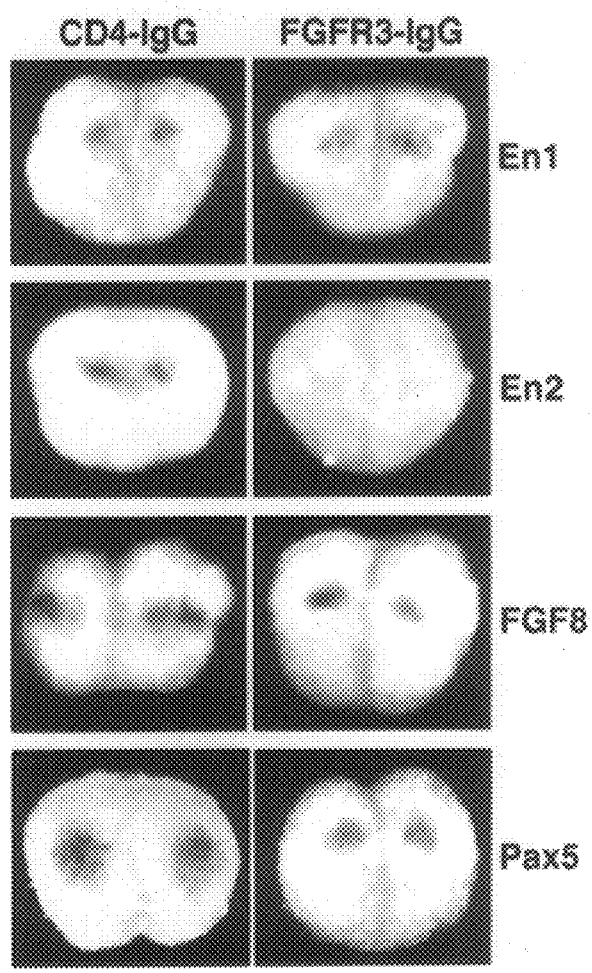

FIGS. 5A–B depicts gel images and photomicrographs which indicate that the soluble FGF-8 blocking antibody FGFR3 blocks the sustained expression of early isthmus region genes. FIG. 5(A) is an RT-PCR analysis of mid/hindbrain markers in 0 somite mid/hindbrain explants (explants #3/4, including both dorsal and ventral aspects) that were exposed to CD4-IgG or FGFR3-IgG and collected at day 0, day 1 or day 4 (for Ptx3, samples were collected at day 5 instead of day 4). Expression of ephrinA5, Otx2, Hes1, PN1, G3PDH and β-actin was not affected by the various treatments (lanes 1–5). In contrast, in the presence of FGFR3-IgG (lanes 3 and 5), but not in the presence of CD4-IgG (lanes 2 and 4) or FGFR1-IgG (data not shown), transcripts for En2, TH and Ptx3 were never detected, whereas transcripts for En1, Pax2, Pax5, Wnt1 and Fgf8 (2 of the 4 alternatively spliced transcripts designated FGF8a, b,g or h) were expressed and persisted for the first day and then declined.

FIG. 5(B) is an in situ hybridization analysis of early mid/hindbrain markers in 0-somite explants #3/4 that were grown for 24 hours in the presence of CD4-IgG (left panels, En1: n=11/11; En2: n=25/27; Fgf8: n=14/14; Pax5: n=8/8), or FGFR3-IgG (right panels, En1: n=9/9; En2: n=11/12; Pax5: n=9/9). Only the expression of En2 is blocked, whereas expression of the other markers does not appear to require FGF8 for the first 24 hours. As judged by vital dye staining, no increase in cell death in the explants was detected under any of the experimental conditions (data not shown). Scale bar represents 160 µm.

FIGS. 6A–6H shows photomicrographs of soluble high affinity FGF-8 blocking antibody (FGFR3) blocking tissue patterning in the rostral forebrain. FIG. 6A shows DA neurons developing in 6 somite stage cephalic explants that were grown in the presence of control antibody [CD4-IgG (n=8/8)]. FIG. 6B shows DA neurons failing to develop in cephalic explants when grown in the presence of FGFR3-IgG (n=0/7). FIG. 6C shows expression of FGF8 in the anterior neural ridge of a 7 somite mouse embryo. FIG. 6D shows expression of Bf1 in the anterior lateral neural plate of a 7 somite stage mouse embryo. FIG. 6E shows that expression of Bf1 is eliminated following unilateral removal of the ANR from cephalic explants (left side) and is not restored in the presence of beads that were soaked with PBS. FIG. 6F shows that expression of Bf1 is restored following exposure to beads that were soaked with FGF8. FIG. 6G shows that Bf1 is expressed in ANR-containing cephalic explants that were exposed to CD4-IgG (n=10/10)or FGFR1-IgG (data not shown). FIG. 6H indicates that the expression of Bf1 (blue) but not of Otx2 (brown) is eliminated in ANR-containing cephalic explants (3 somite stage) that were exposed to FGFR3-IgG (n=0/15). Pro: prosencephal on (forebrain), Mes: mesencephalon (midbrain), Rho: rhombencephalon (hindbrain). Broken white lines in A and B outline the explants. Scale bar represents 200 µm in D; 120 µm in H; 150 µm in all other panels.

Figure 7A:
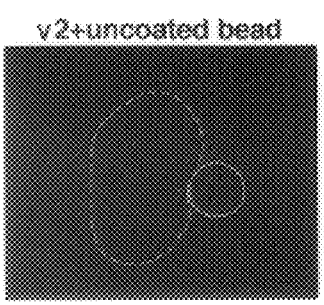
Figure 7D:
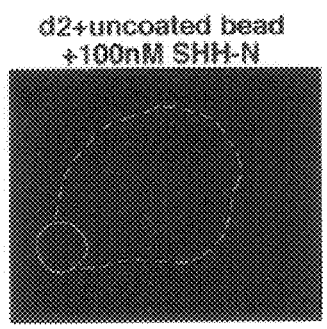
Figure 7B:
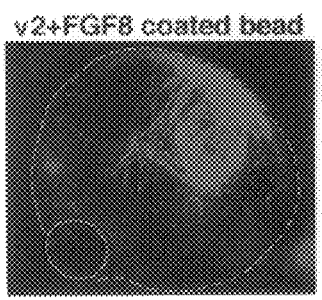
Figure 7E:
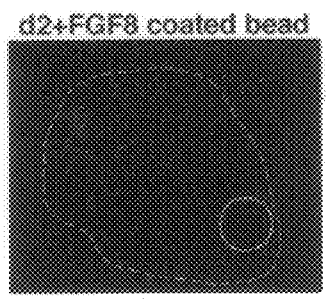
Figure 7C:
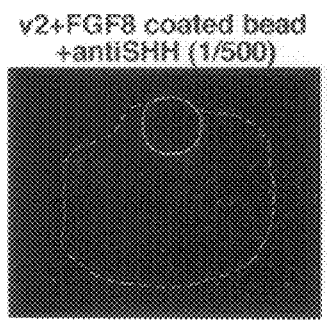
Figure 7F:
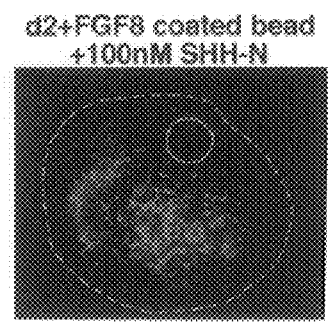
Figure 7G:
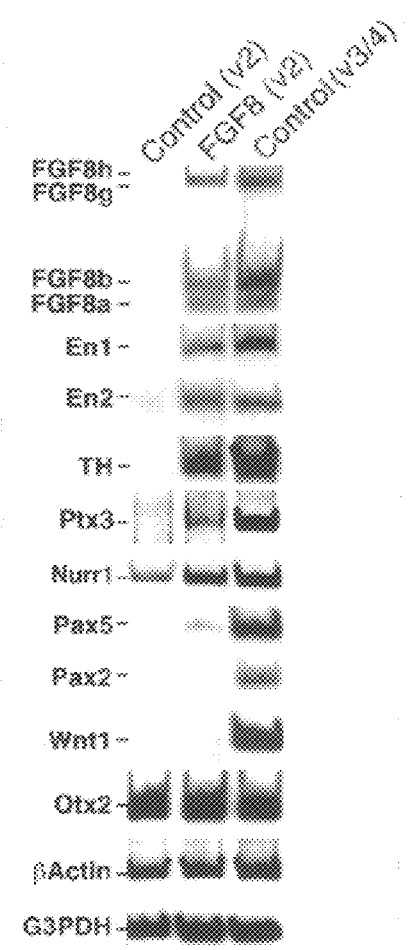

FIGS. 7A–G are photomicrographs and gel images of indicating ectopic induction of mid/hindbrain markers and TH+ neurons by FGF8 and Shh. FIGS. 7A–C TH+ DA neurons (red) are induced in 6 somite rat ventral, caudal forebrain explants (v2) by FGF8 beads in the absence (B, n=14/19), but not in the presence (C, n=0/7) of Shh function blocking antibodies. Control beads do not induce DA neurons (A, n=0/12). In FIGS. 7D–F, DA neurons (red) are induced in 6 somite rat dorsal, caudal forebrain rat explants (d2) in the presence of a combination of Shh and FGF8 proteins (F, n=5/7), but not in the presence of Shh (D, n=0/7), or FGF8 coated beads (E, n=0/8) alone. In FIG. 7G DA neuron markers TH, Nurr1 and Ptx3 as well as the early mid/hindbrain markers En1, En2, Fgf8 and to a lesser extent Pax5 are induced by FGF8 in ventral caudal forebrain explants (v2). Shown are control (v2): v2 explants treated with uncoated beads; FGF8 (v2): v2 explants treated with FGF8 coated beads; and a positive control (v3/4): ventral mid-hindbrain explants v3/4. All explants were taken from 6 somite stage rats, and cultured for 6 days. Dashed white lines mark the boundary of the explants, Solid white lines outline the boundary of the beads. Scale bar=200 µm.

FIGS. 8A–F are photomicrographs and an illustration which indicate that FGF4 induces 5HT neurons in ventral mesencephalic explants. FIGS. 8A–D depict 6 somite rat ventral mesencephalic explants (v3) with (A, B, C) or without (D) paraxial mesoderm which were cultured in collagen gel for 6 days either in control medium (A), or in the presence of 10 ng/ml FGF4 (B and D) or 30 ng/ml FGF4 (C). All the explants were double stained for TH (red) and 5HT (green). (A: n=18/21 TH+, n=0/21 5HT+; B: n=1/7 TH+, n=7/7 5HT+; C: n=0/5 TH+, n=0/5 5HT+; D: n=0/7 TH+, n=7/7 5HT+). (E) Ventral view of a flat-mount presomitic embryo in situ hybridized with Fgf4. Extraembryonic tissues were removed. Anterior is to the left. Scale bar=200 µm in A–D, 120 µm in E.

Figure 8A:
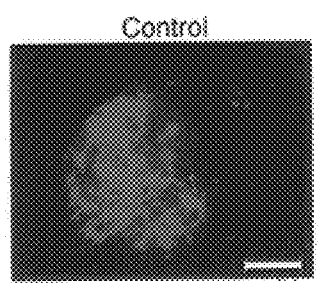
Figure 8B:
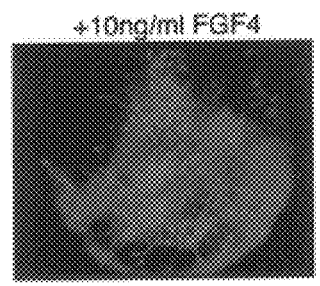
Figure 8C:
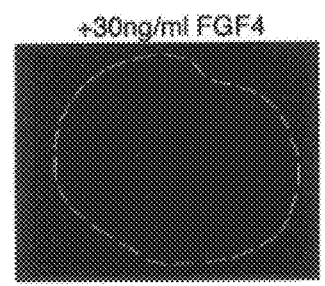
Figure 8D:
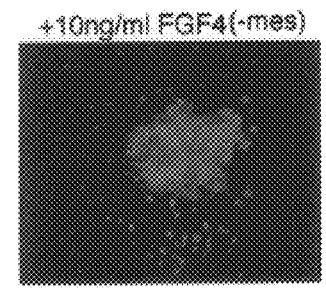
Figure 8E:
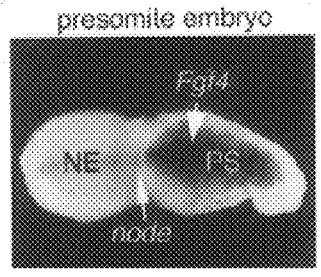
Figure 8F:
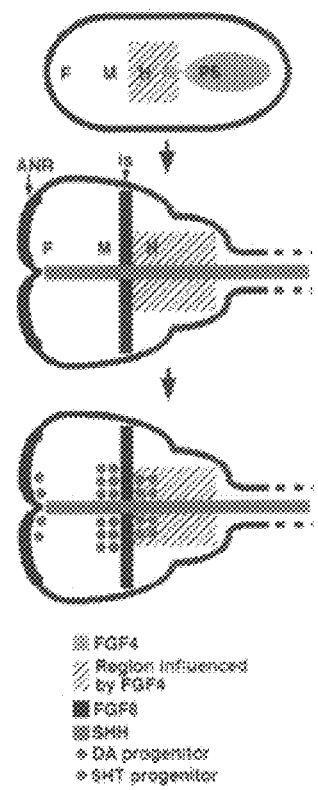

FIG. 8F is a model illustrating the mechanism by which the positions and fates of DA and 5HT neurons are controlled. Anterior is to the left, F: forebrain, M: midbrain, H: hindbrain, NE: neural epithelium; PS: primitive streak. Top panel: presomitic embryo. Middle and bottom panel: late somatogenic embryo. DA neurons (orange dots) are illustrated at the intersections of FGF-8 (purple) and sonic hedgehog (Shh) expression, while 5HT neurons (green dots) are illustrated at the overlapping zones of FGF-8, Shh and FGF-4 expression.

FIG. 9 represents the nucleotide sequence (SEQ ID NO: 1) and amino acid sequence translated therefrom (SEQ ID NO: 2) for FGF-4 used in the Examples.

FIG. 10 represents the nucleotide sequence (SEQ ID NO: 3) and amino acid sequence translated therefrom (SEQ ID NO: 4) for FGF-8 used in the Examples.

FIGS. 11A–B represents the nucleotide sequence (SEQ ID NO: 5) and amino acid sequence translated therefrom (SEQ ID NO: 6) for sonic hedgehog (Shh) used in the Examples.

FIGS. 12A–B represents the nucleotide sequence for CD4-IgG (SEQ ID NO: 7), a control soluble receptor IgG fusion used in the Examples.

FIGS. 13A–B represents the nucleotide sequence for IgG-FGFR1 (SEQ ID NO: 8), a soluble high affinity receptor used in the Examples.

FIGS. 14A–B represents the nucleotide sequence for IgG-FGFR3 (SEQ ID NO: 9), a soluble low affinity receptor used in the Examples.

DETAILED DESCRIPTION OF THE PREFERRED EMBODIMENTS

I. Definitions

The terms employed throughout this application are to be construed with the normal meaning to those of ordinary skill in the art. However, applicants desire that the following terms be construed with the particular definitions as described. All references mentioned in this application should be interpreted and read as being incorporated by reference.

The terms "protein" or "polypeptide" are intended to be used interchangeably. They refer to a chain of two (2) or more amino acids which are linked together with peptide or amide bonds, regardless of post-translational modification (e.g., glycosylation or phosphorylation). The polypeptides of this invention may comprise more than one subunit, where each subunit is encoded by a separate DNA sequence.

The terms "FGF-4 polypeptide" or "FGF-4", "FGF-8 polypeptide"or "FGF-8", and "Shh polypeptide" or "Shh" are used herein to encompass native-sequence FGF-4, FGF-8 and Shh protein and variants (which are hereafter defined).

The FGF-4, FGF-8 and Shh polypeptide may be isolated from a variety of sources, such as from human tissue types or from another source, or prepared by recombinant or synthetic methods, or by any combination of these and similar techniques.

A "native-sequence FGF-4 polypeptide," "native-sequence FGF-8 polypeptide" and "native-sequence sonic hedgehog polypeptide" comprise polypeptides having the same amino acid sequence as an FGF-4, FGF-8 or Shh polypeptide derived from nature, with or without the native signal sequence and with or without the N-terminal methionine. Such native-sequence polypeptides can be isolated from nature or they can be produced by recombinant or synthetic means. The term "native-sequence FGF-4, FGF-8 or Shh polypeptide", "native-sequence FGF-8 polypeptide" and "native-sequence sonic hedgehog" specifically encompass naturally occurring truncated forms of a polypeptide disclosed herein, naturally occurring variant forms (e.g., alternatively spliced forms), and naturally occurring allelic variants of the respective polypeptides.

The FGF gene family constitutes a family of structurally related ligands that act to promote the growth and differentiation of many mesoderm and ectoderm cells by binding to specific receptors. Fibroblast growth factor-8 (FGF-8), alternatively known as androgen-induced growth factor (AIGF) is a member of the FGF family known to influence embryogenesis and morphogenesis. The in situ embryonic expression pattern suggests a unique role of FGF-8 in mouse development, especially in gastrulation, brain development, and limb and facial morphogenesis. Ohuchi, H, et al., *Biochem. Biophys. Res. Commun.* (1994) 204(2): 882–888. Northern blot expression reveals a unique temporal and spatial pattern of FGF-8 expression in the developing mouse and suggests a role for this FGF in multiple regions of ectodermal differentiation in the post-gastrulation mouse embryo. Heikinheimo, M. et al., *Mech. Dev.* (1994) 48(2): 129–138. A sequence of FGF-8 for use in the present invention appears in FIG. 10.

Fibroblast growth factor-4 (FGF-4), also known as hst or K-FGF was first isolated as a transforming gene identified from transformed NIH 3T3 cells that were transfected with the DNA of a human stomach cancer. Yoshida, T. et al., *Proc. Natl. Acad, Sci. USA* (1987) 84(20): 7305–7309. It has been further shown to cause autocrine growth stimulation when transfected into human adrenal cortex carcinoma cells (SW-13), Wellstein, A., et al., *Cell Growth Differ.* (1990) 1(2): 63–71. FGF-4 has further been shown to be significant in early embryonic development. Wilder, P. J., et al., *Dev. Biol.* (1997) 192(2): 614–629. A sequence of FGF-4 for use in the present invention appears in FIG. 9.

Sonic hedgehog (Shh) is one of three mammalian homologs of the Drosophila hedgehog signaling molecule and is expressed at high levels in the notochord and floor plate of developing embryos. Shh is known to play a key role in neuronal tube patterning, Echerlard et al., *Cell* 75: 1417–30 (1993), the development of limbs, somites, lungs and skin. Moreover, overexpression of Shh has been found in basal cell carcinoma. A sequence of Shh for use in the present invention appears in FIG. 11.

The terms "FGF-4 variant", "FGF-8 variant" and "Shh variant" mean an active FGF-4, FGF-8 or Shh polypeptide as defined below having at least at least 85% amino acid sequence identity with the amino acid sequence of the respective native molecule, more preferably at least 90%, and most preferably at least 95% amino acid sequence identity with the respective human sequences shown in FIGS. 9–11. Such variants include, for instance, FGF-4, FGF-8 or sonic hedgehog polypeptides wherein one or more amino acid residues are added, or deleted, at the N- or C-terminus of the full-length amino acid sequence of the respective molecules depicted in FIGS. 9–11, functional fragments or analogs of the respective native-sequence FGF-4, FGF-8 or Shh having qualitative biological activity in common with the respective full-length polypeptides, including variants from other species, but excludes a native-sequence polypeptide. For example, a functional fragment of Shh might include the N-terminal residues 1–195. Alternatively, a variant can be a biologically active FGF-4, FGF-8 or sonic hedgehog encoding nucleic acid which can hybridize under stringent conditions to a nucleic acid encoding a variant enumerated above.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends upon the ability of denatured DNA to reanneal when complementary strands are present in an environment near but below their $T^m$ (melting temperature). The higher the degree of desired homology between the probe and hybridizable sequence, the higher the relative temperature which can be used. As a result, it follows that higher relative temperatures would tend to make the reaction conditions more stringent, while lower temperatures less so. Moreover, stringency is also inversely proportional to salt concentrations. For additional details and explanation of stringency of hybridization reactions, see Ausubel et al., *Current Protocols in Molecular Biology* (1995).

"Stringent conditions," as defined herein may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (vol/vol) fonnamide with 0.1% bovine serum albumin/0.1% Ficoll/0.1% polyvinylpurrolidone/50 mM sodium phosphate buffer at pH 6.5 with 750 mM sodium chloride, 75 mM sodium citrate at 42° C.; (3) employ 50% formamide, 5×SSC (0.75 M NaCl, 0.075 sodium citrate), 50 mM sodium phosphate (pH 6.8), 0.1% sodium pyrophosphate, 5×Denhardt's solution, sonicated salmon sperm DNA (50 g/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

Polypeptide variants may come in different forms. "Substitutional" variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule. "Insertional" variants are those with one or more amino acids inserted immediately adjacent to an amino acid at a particular position in a native sequence. Immediately adjacent to an amino acid means connected to either the α-carboxyl or α-amino functional group of the amino acid. "Deletional" variants are those with one or more amino acids in the native amino acid sequence removed. Ordinarily, deletional variants will have one or two amino acids deleted in a particular region of the molecule. Polypeptide variants also include covalent modifications to residues in addition to epitope-tagged heterogeneous FGF-4, FGF-8 and sonic hedgehog polypeptides.

"Active" FGF-4, FGF-8 or Shh or "biological activity" of FGF-4, FGF-8 or Shh or FGF-4, FGF-8 or Shh "biological activity", for purposes herein, describes form(s) of an FGF-4, FGF-8 or Shh polypeptide which retain the biological activity of causing neuroprogenitor cells to differentiate into dopaminergic or serotonergic neurons. For example, a biologically active FGF-8 and sonic hedgehog variants are polypeptides which can cause neuroprogenitor cells to differentiate into dopaminergic neurons, and in combination with pre-treatment with biologically active FGF-4 can cause neuroprogenitor cells to differentiate into serotonergic neurons.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and from animals, and zoo, sports, or pet animals, such as dogs, horses, cats, sheep, pigs, cattle, etc. Preferably, the mammal is human.

A "disorder" is any condition that would benefit from treatment with dopaminergic or serotonergic neurons. Examples of disorders that would benefit from implantation of dopaminergic neurons are those associated with improper postural reflexes, movement and reward-associated behaviors, including, Parkinson's disease, schizophrenia and drug addiction. Examples of disorders that would benefit from implantation of serotonergic neurons are those characterized by abnormalities in awareness, arousal, behavior, and food intake, including aggression, depression (including suicidal behavior), schizophrenia and anorexia/bulimia.

An "effective amount" of sonic hedgehog (Shh), fibroblast growth factor-8 (FGF-8) is such amount that is sufficient to cause differentiation of neuroprogenitor cells into dopaminergic neurons. Similarly, an "effective amount" of the combination of FGF-4 and Shh and FGF-8 is such amount that is sufficient to cause differentiation of neuroprogenitor cells into serotonergic neurons. An "effective amount" of neuronal survival factor is such amount so as to promote the survival of a greater population of neuronal cells than would otherwise exist without the survival factor.

A "neuronal survival factor" is any substance which causes neurons (either in cell culture disassociation or as a transplanted mass) to which the factor is placed into contact with to survive for a period of time greater than would occur than would otherwise occur. For example, use of neuronal survival factors in conjunction with Shh, FGF4, FGF8 may also be employed. For example, U.S. Pat. No. 5,733,875 describes a method of using Glial-derived neurotrophic factor (GDNF) to protect or prevent epileptic seizures. GDNF is a known agent having trophic activity for embryonic midbrain ventral mesencephalic dopaminergic neurons in vitro. Lin et al., *Science* 260: 1130–1132 (1993; Lin et al., *J. Neurochem.* 63: 758–768 (1994). Recombinant human GDNF has also been demonstrated to induce sprouting of dopaminergic fibers in vivo (Hudson et al., *Soc. Neurosci. Absir.* 19: 652 (1993)), increase dopainine turnover in the substantia nigra or rats (Hudson et al., supra., Miller et al., *Soc. Neitrosci. Abstr.* 20: 535–7 (1994)), protect neurons against 6-OHDA lesions, and augment growth and fiber formation of rat fetal transplants of nigral tissue in oculo, Stromberg et al., *Exp. Neurol.* 124: 401–412 (1993).

Brain-derived Neurotrophic factor (BDNF) is a trophic factor for peripheral sensory neurons, dopaminergic neurons and retinal ganglia (Henderson et al., 1993, *Restor. Neurol. Neurosci.* 5: 15–28). BDNF has also been shown to prevent normally-occurring cell death both in vitro and in vivo (Hofer and Barde, 1988, *Nature* 331: 161–262. Neurotrophin 3 is found both in the central and peripheral nervous systems and is capable of promoting the survival of sensory and sympathetic neurons, including dorsal root ganglia (DRG) explants. Ciliary NeuroTrophic Factor (CTNF) promotes the survival of chicken embryo ciliary ganglia in vitro and was also found to support survival of cultured sympathetic, sensory and spinal motor neurons (Ip et al., 1991, *J. Physiol.* 85: 123–130. Local administration of this protein to the lesion site of newborn rats has been shown to prevent the degeneration of the corresponding motor neurons. CNTF also rescued motor neurons from developmental cell death (Henderson et al., 1993, *Restor. Neurol. Neurosci.* 5: 15–28.

Additional neuronal survival factors include nerve growth factors (NGF), aGF, neurotrophin-3 (NT-3), neurotrophin-4 (NT-4), aFGF, IL-1$\beta$, TNF$\alpha$, insulin-like growth factor (IGF-1, IGF-2), transforming growth factor beta (TGF-$\beta$, TGF-$\beta$1).

A "therapeutically effective amount" of progenitor cells is such amount which arrests or ameliorates the physiological effects caused by the loss or damage to dopaminergic or serotonergic neurons. A suitable range of cells can range from about 100 to about 500,000 active neurons can be employed. Preferably, the range is about 500 to about 500,000, most preferably about 1,000 to about 500,000.

"Dopaminergic (DA) neurons" refers to neurons which secrete the neurotransmitter dopamine. They innervate the striatum, limbic system, and neocortex and reside in the ventral midbrain together with several other classes of neurons including motoneurons. DA neurons control postural reflexes, movement and reward-associated behaviors. The loss of DA neurons results in Parkinson's disease and their abnormal function have been associated with schizophrenia and drug addiction.

"Serotonergic (SHT) neurons" refers to neurons which secrete the neurotransmitter serotonin (5-hydroxytryptamine). SHT neurons typically have a slow, rhythmic pattern of firing and are concentrated in the ventral and ventrolateral aspects of the hindbrain and innervate most parts of the central nervous system including the cerebral cortex, limbic system and spinal cord. 5HT neurons control levels of awareness, arousal, behavior and food intake. The abnormal function of serotonergic neurons has been linked to aggression, depression (including suicidal behavior) and schizophrenia.

"Neuroprogenitor cells" are cells which give rise to or differentiate into neurons. They have been observed to differentiate into various neuronal classes dependent on their relative placement along the anterior-posterior and dorsal-ventral axis.

II. Identification of FGF-4, FGF-8 or Shh

The description below relates primarily to production of FGF-4, FGF-8 or sonic hedgehog polypeptide by culturing cells transformed or transfected with a vector comprising FGF-4, FGF-8 or Shh nucleic acid. It is of course contemplated that alternative methods, which are well known in the art, may be employed to preparing these polypeptides. For example, the FGF-4, FGF-8 or Shh amino acid sequence, or active portions thereof, may be produced by direct peptide synthesis using solid-phase technique. Stewart et al., *Solid-Phase Peptide Synthesis* (W.H. Freeman Co., San Francisco, Calif. 1969); Merrifield, *J. Am. Chem. Soc.* 85: 2149–2154 (1963). In vitro protein synthesis may be performed using manual techniques or by automation. Automated synthesis may be accomplished, for example, using an Applied Biosystems peptide synthesizer (Foster City, Calif.) in accordance with the manufacturer's instructions. Various portions of FGF-4, FGF-8 or Shh polypeptide may be chemically synthesized separately and combined using chemical or enzymatic methods to produce the respective full-length polypeptide.

III. Recombinant Production of FGF-4, FGF-8 or Shh

FGF-4 may be purchased from any high quality laboratory reagent supply company. For example, R & D systems, 614 McKinley Place, N.E., Minneapolis, Minn. 55413. Alternatively, FGF4, FGF-8 and Shh can be prepared using techniques described herein as well as standard and known techniques such as those described in Sam brook et al., infra and/or Ausubel et al., infra. A preparation for FGF-8 is described in MacArthur, C. et al., *Development* 121: 3603–3613. A preparation for Shh is described in Hynes et al., *Neuron* 15: 35–44.

The FGF-4, FGF-8 and Shh polypeptides of the present invention may be prepared by standard recombinant methods by culturing cells transfected to express FGF-4, FGF-8 or Shh nucleic acid. A typical standard method is by transforming the cells with an expression vector and recovering the polypeptide from the cells. However, it is envisioned that the FGF-4, FGF-8 or Shh polypeptides may be produced by homologous recombination, or by recombinant production methods utilizing control elements introduced into cells already containing DNA encoding the respective polypeptides. For example, a promoter, enhancer element, a suppresser, or an exogenous transcription modulatory element may be inserted in the genome of the intended host cell in proximity of and in an orientation sufficient to influence the transcription of DNA encoding the desired FGF-4, FGF-8 or Shh polypeptide. The control element does not encode FGF-4, FGF-8 and Shh, rather the DNA can be indigenous to the host cell genome. Next, cells can be screened for making the polypeptides of this invention, or for increased or decreased levels of expression, as desired. General techniques of recombinant DNA technology are, for example, disclosed in Sambrook et al., *Molecular Cloning: A Laboratory Manual*, 2d Edition (Cold Spring Harbor Press, Cold Spring Harbor, N.Y. (1989) and in Ausuble et al., *Current Protocols in Molecular Biology*, John Wiley and Sons, Inc. USA (1995).

Thus, the invention contemplates a method for producing FGF-4, FGF-8 or Shh comprising inserting into the genome of a cell containing nucleic acid encoding a FGF-4, FGF-8 or Shh polypeptide, a transcription modulatory element and the nucleic acid molecule. The invention also contemplates a host cell containing the indigenous FGF-4, FGF-8 or Shh polypeptide nucleotide operably linked to endogenous control sequences recognized by the host cell.

B. Amino Acid Variants of Native FGF-4, FGF-8 or Shh Proteins or Fragments

Amino acid sequence variants of native FGF-4, FGF-8 or Shh proteins and functional fragments thereof may be prepared by methods known in the art by introducing appropriate nucleotide changes into a native or variant FGF-4, FGF-8 or Shh, or by in vitro synthesis of the desired polypeptide. There are two principal variables in the construction of amino acid sequence variants: (1) the location of the mutation site and; (2) the nature of the mutation. With the exception of naturally-occurring alleles, which do not require the manipulation of the DNA sequence encoding FGF-4, FGF-8 or Shh, the amino acid sequence variants of the respective polypeptides are preferably constructed by mutating the respective native sequences, either to arrive at an allele or an amino acid sequence variant that does not occur in nature.

Amino acid alterations can be made at sites that differ in FGF-4, FGF-8 or Shh from various species, or in highly conserved regions, depending on the goal to be achieved. For example, mutations which result in an enzyme with greater affinity for the FGF-4, FGF-8 or Shh receptors in neuroprogenitor cells.

Sites of mutations will typically be modified in series, e.g., by (1) substituting first with conservative choices, and then with more radical selections depending upon the results achieved, (2) deleting the target residue of residues, or (3) inserting residues of the same or different class adjacent to the located site, or combinations of options (1)–(3).

Additionally, if the method of the invention involves the transplant of neuroprogenitor cells in combination with continuing exposure to the polypeptides FGF-4, FGF-8 and/or Shh, such variants which confer longer half-life upon such polypeptides (e.g., PEG modifications) is also within the realm of those of ordinary skill.

C. Selection and Use of a Replicable Vector

The nucleic acid (e.g. cDNA or genomic DNA) encoding native or variant FGF-4, FGF-8 or Shh polypeptide or functional fragment thereof is inserted into a replicable vector for further cloning (amplification of the DNA or for expression). Many vectors are available, and selection of the appropriate vector will depend on (1) whether it is to be used for DNA amplification or for DNA expression, (2) the size of the nucleic acid to be inserted into the vector, and (3) the host cell to be transformed with the vector. Each vector contains various components depending on its function (amplification of DNA or expression of DNA) and the host cell with which it is compatible. That said, the vector may take the form of a plasmid, cosmid, viral particle or phage. The appropriate nucleic acid may be inserted into the vector by a variety of procedures. In general, DNA is inserted into an appropriate restriction endonuclease site(s) using techniques known in the art. The vector components generally include, but are not limited to, one or more of the following: a signal sequence, an origin of replication, one or more marker genes, an enhancer element, a promoter, and a transcription termination sequence, each of which is described below.

The preferred method of FGF-4, FGF-8 or Shh production is direct expression. Additional techniques exist to enhance the expression of heterologous genes in *E. coli*, such as is found in Yansura, D. & Simmons, L., *Enzymology* 4: 151–158 (1992). Preferably, the expression vector can be constructed from pBR322 [Sutcliffe, *Cold Spring Harbor Symp. Quant. Biol.* 43: 77–90 (1978)]. A Trp promoter is used to provide the transcriptional sequence required for efficient preferred expression of the FGF-4, FGF-8 or Shh gene in *E. coli*. Yanofsky et al., *Nucleic Acids Res.* 9: 6647–6668 (1981). Two Shine-Daloarno sequences, the Trp Shine-Dalgarno and a second Shine-Dalgarno, are used to facilitate the translation of FGF-4, FGF-8 or Shh. Yanofsky et al., supra; Ringquist et al., *Mol. Microbiol.* 6: 1219–1229 (1992). The FGF-4, FGF-8 or Shh coding sequence is located downstream of the promoter and Shine-Dalgarno sequences.

D. Selection and Transformation of Host Cells (1) Host cells

Suitable host cells for cloning or expressing the DNA in the vectors herein are the prokaryote, yeast, or higher eukaryote cells described above. Suitable prokaryotes for this purpose include eubacteria, such as Escherichia, e.g., *E. coli*, Enterobacter, Erwinia, Klebsiella, Proteus, Salmonella, e.g., *Salmonella typhimurium*, Serratia, e.g., *Serratia marcescans*, and Shigella, as well as Bacilli such as *B. Subtilis* and *B. Licheniformis* (e.g., *B. Licheniformis* 41P disclosed in DD 266,710 published Apr. 12, 1989), Pseudomonas such as *P. aeruginosa, Salmonella typhimurium*, or *Serratia marcescans* and Streptomyces. The preferred strains have and impaired heat shock response and contain protease deletions and mutations. For example, the strain 44C6, which is a derivative of W3110 (ATCC 27,325) having the genotype fhuA (tonA) Ion galE rpoHts (htpRts) clpP. Another secretion strain which may be used is 27C7 (ATCC 55,244). Other *E. coli* cloning hosts include, for example, *E. coli* 294 (ATCC 31,446), *E. coli* B and *E. coli* X1776 (ATCC 31,537).

(2) Culturing the host cells

Prokaryotic cells used to produce the FGF-4, FGF-8 or Shh variants of this invention may be cultured in suitable media as described generally in Sambrook et al., supra and Ausubel et al., supra. Briefly, the transformed cells are grown at 30° C. or 37° C. until the optical density (measured at 550 nm) reaches about 2–3. The culture is diluted into a production medium, regrown with aeration, and 3-Indole acrylic acid (IAA) is added. Growth is continued with aeration for about another 15 hours after which time the cells are harvested by centrifugation. When refolding is necessary, the procedure outlines under F. Isolation, Purification and Refolding of Mutant FGF-4, FGF-8 or Shh, below, may be employed.

More specifically, a 10 liter fermentation may be carried out as follows. The fermentor is first sterilized with a sterilization solution of about 5–6.5 liters of deionized water to which is added: ammonium sulfate (50.0 g); potassium phosphate, dibasic (60.0 g); sodium phosphate, monobasic dihydrate (30.0 g); sodium citrate, dihydrate (10.0 g); 1-isoleucine (5 g); 25% aq. soln. of pluronic polyol L-61 (BASF, antifoam). After the fermentor vessel cools down, the growth media is added. The growth media after inoculation has a volume typically of about 8.5 liters. The media components are comprised of: 50% glucose solution (15 mL); 1M magnesium sulfate (70 mL); 20% Hycase solution (250 mL); 20% yeast extract solution (250 ml,); 2 mg/mL ampicillin (250 mL) and trace metals (5 mL). A typical 1 L trace metal solution is composed of the following: HCl (100 mL); Ferric chloride hexahydrate (27 g); Zinc sulphate heptahydrate (8 g); Cobalt Chloride hexahydrate (7 g); Sodium molybdate (7 g); Cupric sulphate pentahydrate (8 g); boric acid (2 g); Manganese sulphate monohydrate (5 g); distilled water (total volume to 1 L). Inoculation is made with 500 mL of an 18–20 hour LB culture grown in the presence of ampicillin, and the fermentor is agitated at 750 rpm and aerated at 10 slpm. The culture pH is maintained at 7.0 by automatic addition of ammonium hydroxide and the temperature is maintained at 30° C. When the initial glucose in the culture is exhausted, a glucose feed is started and maintained at a rate sufficient to sustain growth but not accumulate in the medium. Culture growth is monitored by measuring the optical density (O.D.) at 550 nm. When the culture O.D. reaches 25–35, 25 mL of a 25 mg/mL solution of IAA is added and the cell paste harvested after 14–18 hours of centrifugation.

(3) Detecting Gene Amplification/Expression

Gene amplification and/or expression may be measured in a sample directly, for example, by conventional Southern blotting, northern blotting to quantitate the transcription of mRNA (Thomas, *Proc. Natl. Acad. Sci. USA* 77: 5201–5205 (1980), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wise variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path*. 75: 734–738 (1980).

Antibodies useful for immunohistochemical staining and/ or assay of sample fluids may be either monoclonal or polyclonal, and may be prepared in any mammal. Conveniently, the antibodies may be prepared against an FGF-4, FGF-8 or Shh mutant polypeptide or against a synthetic peptide based on the DNA sequences provided herein as described further below.

E. FGF-4, FGF-8 or Shh Polypeptide Purification

FGF-4, FGF-8 or Shh mutant preferably is recovered from host cell lysates when directly expressed without a secretory signal, although it may also be recoverable from the culture media as a secreted polypeptide. If membrane-bound, it can be released from the membrane using a suitable detergent solution (e.g., Triton-X 100) or by enzymatic cleavage. Cells employed in expression of FGF-4, FGF-8 or Shh polypeptides can be disrupted by various physical or chemical means, such as freeze-thaw cycling, sonication, mechanical disruption, or cell lysing agents.

When using recombinant techniques, the FGF-4, FGF-8 or Shh polypeptide mutant can be produced intracellularly, in the periplasmic space, or directly secreted into the medium. If the FGF-4, FGF-8 or Shh mutant is produced intracellularly, it will usually be necessary to purify the mutant from other recombinant cell proteins or polypeptides to obtain preparations that are substantially homogenous to the FGF-4, FGF-8 or Shh mutant. As a first step, the culture medium or lysate is centrifuged to remove the particulate debris, e.g. host cells or lysed fragments. A procedure is described in Carter et al., *Bio/Technology* 10: 163–167 (1992) for isolating proteins which are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation.

Many heterogeneous proteins expressed in *E. coli* require refolding in order to impart activity. When this is necessary, the following procedure can be used. For a general discussion of procedures suitable for refolding of recombinant or synthetic FGF-4, FGF-8 or Shh, include any N- or C-terminal extended forms, the reader is referred to the following patents: Builder et al., U.S. Pat. No. 4,511,502; Jones et al., U.S. Pat. No. 4,512,922; Olson, U.S. Pat. No. 4,518,526; Builder et al., U.S. Pat. No. 4,620,948.

(i) Recovery of non-soluble mutant FGF-4, FGF-8 or Shh

A microorganism such as E. coli which is expressing mutant FGF-4, FGF-8 or Shh encoded by any suitable plasmid is fermented under conditions in which mutant FGF-4, FGF-8 or Shh is deposited in insoluble "refractile bodies". Optionally, cells are first washed in a cell disruption buffer. Typically, about 100 g of cells are resuspended in about 10 volumes of a cell disruption buffer (e.g. 10 mM Tris, 5 mM EDTA, pH 8) with, for example, a Polytron homogenizer, followed by centrifug,ation at 5000×g for 30 minutes. Cells are then lysed using any conventional technique such as tonic shock, sonication, pressure cycling, chemical or enzymatic methods. For example, the washed cell pellet above may be resuspended in another 10 volumes of a cell disruption buffer with a homogenizer and the cell suspension is passed through an LH Cell Disrupter (LH Inceltech, Inc.) or through a Microfluidizer® (Microfluidics Int'l) according to the manufacturer's instructions. The particulate matter containing mutant FGF-4, FGF-8 or Shh is then separated form the liquid phase and optionally washed with any suitable liquid. For example, a suspension of cell lysate may be centrifuged at 5,000×g for 30 minutes, resuspended and optionally centrifuged a second time to make a washed refractile body pellet. The washed pellet may be used immediately or optionally stored frozen (at e.g. −70° C.).

(ii) Solubilization and Purification of Monomeric mutant FGF-4, FGF-8 or Shh Insoluble FGF-4, FGF-8 or Shh polypeptide in the refractile body is then solubilized with a solubilizing buffer. The solubilizing buffer contains a chaotropic agent and is usually buffered at a basic pH and contains a reducing agent to improve the yield of monomeric FGF-4, FGF-8 OR SHH. Representative chaotropic agents include urea, guanidine-HCl, and sodium thiocyanate. A preferred chaotropic agent is guanidine-HCl. The concentration of chaotropic agent is usually 4–9 M, preferably 6–8 M. The pH of the solubilizing buffer is maintained by any suitable buffer in a pH range of from about 7.5–9.5, preferably 8.0–9.0, and most preferably 8.0. Preferably, the solubilizing buffer also contains a reducing agent to aid formation of the monomeric form of FGF-4, FGF-8 or Shh. Suitable reducing agents include organic compounds containing a free thiol (RDH). Representative red ucing agents include dithiothreitol (DTT), dithioerythritol (DTE), mercaptoethanol, glutathione (GSH), cysteamine and cysteine. A preferred reducing agent is dithiothreitol (DTT). Optionally, the solubilizing buffer may contain a mild oxidizing agent (e.g. molecular oxygen) and a sulfite salt to form monomeric mutant FGF-4, FGF-8 OR Shh via sulfitolysis. In this embodiment, the resulting [FGF-4, FGF-8 or Shh]-S-sulfonate is later refolded in the presence of redox buffer (e.g., GSH/GSSG) to form the properly folded FGF-4, FGF-8 or Shh.

The FGF-4, FGF-8 or Shh protein is usually further purified using, for example, centrifugation, gel filtration chromatography and reversed phase column chromatography.

By way of illustration, the following procedure has produced suitable yields of monomeric FGF-4, FGF-8 or Shh. The refractile body pellet is resuspended in about 5 volumes by weight of the solubilizing buffer (20 mM Tris, pH 8, with 6–8 M guanidine and 25 mM DTT) and stirred for 1–3 hr., or overnight at 4° C. to effect solubilization of the mutant FGF-4, FGF-8 or Shh protein. High concentrations of urea (6–8M) are also useful but generally result in somewhat lower yields compared to guanidine. After solubilization, the solution is centrifuged at 30,000×g for 30 min. to produce a clear supernatant containing denatured, monomeric FGF-4, FGF-8 or Shh. The supernatant is then chromatographed on a Superdex® 200 gel filtration column (Pharmacia, 2.6×60 cm) at a flow rate of 2 ml/min. and the protein eluted with 20 mM Na phosphate, pH 6.0, with 10 mM DTT. Fractions containing monomeric, denatured FGF-4, FGF-8 or Shh eluting between 160 and 200 ml are pooled. The FGF-4, FGF-8 or Shh protein is further purified on a semi-preparative C4 reversed phase column (2×20 cm VYDAC). The sample is applied at 5 m/min. to a column equilibrated in 0.1% TFA (trifluoroacetic acid) with 30% acetonitrile. The protein is eluted with a linear gradient of acetonitrile (30–60% in 60 min.). The purified reduced protein elutes at approximately 50% acetonitrile. This material is used for refolding to obtain biologically active FGF-4, FGF-8 or Shh.

(iii) Refolding of Mutant FGF-4, FGF-8 or Shh to Generate the Biologically Active Form Following solubilization and further purification of mutant FGF-4, FGF-8 or Shh, in order to obtain the biologically active form, it may be necessary to refold the denatured monomeric mutant FGF-4, FGF-8 or Shh in a redox buffer. Depending upon the potency of the mutant FGF-4, FGF-8 or Shh, it may be possible to obtain biologically active material utilizing many different buffer, detergent and redox conditions. However, under most conditions, only a small amount of properly folded material (<10%) is obtained. For commercial manufacturing processes, it is desirable to have refolding yields at least 10%, more preferably 30–50% and most preferably >50%. Many different detergent including Triton X-100, dodecyl-beta-maltoside, CHAPS, CHAPSO, SDS, sarkosyl, Tween 20 and Tween 80, Zwittergent 3–14 and others may be used to produce at least minimal folding. However, the most preferred detergents are of the CHAPS family (CHAPS and CHAPSO) which appear to work best in refolding and limit protein aggregation and improper disulfide formation. Levels of CHAPS greater than about 1% are most preferred. To optimize yields, it is preferred to have sodium chloride present (0.1M–0.5M). It is further preferred to have EDTA (1–5 mM) in the redox buffer in order to limit the amount of metal-catalyzed oxidation (and aggregation). At least 15% glycerol is further preferred in order to reach optimal refolding conditions. For maximum yields, it is further preferred that the redox buffer have both an oxidized and reduced organic thiol (RSH). Suitable redox pairs include mercaptoethanol, glutathione (GSH), cysteamine, cysteine and their corresponding oxidized forms. Preferred redox are glutathione (GSH) :oxidized glutathilone (GSSG) or cysteine:cystine. The most preferred redox pair is glutathione (GSH):oxidized glutathione (GSSG). Generally higher yields are observed when the mole ratio of oxidized member of the redox pair is equal to or in excess over the reduced member of the redox pair. pH values between 7.5 and about 9 are optimal for refolding of FGF-4, FGF-8 or Shh polypeptides. Organic solvents (e.g. ethanol, acetonitrile, methanol) were tolerated at concentrations of 10–15% or lower. Higher levels of organic solvents increased the amount of improperly folded forms. Tris and phosphate buffers were generally useful. Incubation at 4° C. also produced higher levels of properly folded FGF-4, FGF-8 or Shh.

Refolding yields of 40–60% (based on the amount of reduced and denatured FGF-4, FGF-8 or Shh used in the refolding reaction) are typical for preparations of FGF-4, FGF-8 or Shh that have been purified through the first C4 step. Active material can be obtained when less pure preparations (e.g. directly after the Superdex® 200 column or after the initial refractile body extraction) although the yields can be less due to precipitation and interference of non-FGF-4, FGF-8 or Shh proteins during the FGF-4, FGF-8 or Shh refolding process.

In the event that FGF-4, FGF-8 or Shh have three or more cysteine residues, to assist in achieving optimal results during refolding, it may become necessary to mutate the third cysteine so as to ensure formation of the disulfide bond between the first and second cysteines.

During the initial exploration in determining refolding conditions, different peaks containing the mutant FGF-4, FGF-8 or Shh protein can be separated by C4 reverse phase chromatography. Upon testing for the peak with the most significant biological activity, conditions may be optimized to yield preferentially for that version.

IV. Therapeutic Indications

Various conditions can be treated by the administration of dopaminergic and serotonergic neurons.

Serotonergic neurons control levels of awareness, arousal, behavioral traits and food intake, and their abnormal function has been linked to aggression, depression and schizophrenia (Jacobs and Gelperin (1981) *Serotonin Neurotransmission and Behavior*. The MIT Press, Cambridge, Mass.). Serotonergic neurons innervate nearly every area of the central nervous system, including the cerebral cortex, limbic system and spinal cord, and can influence multiple functions of the brain, such as behavior, appetite, pain, sexual activity, responses to stress, pain and immune function, cardiovascular function, hormone secretion, and temperature regulation. Serotonergic dysfunction is likely to play roles in the pathophysiology of various psychiatric, neurologic, and other diseases. For example, mental depression, Asberg el al., *J. Clin. Psychiatry* 47(4): 23–35 (1986), suicide, Asberg et al., supra, Lester, D., *Pharmocopsychiatry* 28(2): 45–50 (1995), and violent aggressive behavior, Brown et al., *J. Clin. Psychiatry* 54(4): 31–41 (1990), Eichelman, B. S., *Annu. Rev. Med.* 41: 149–158(1990). Serotonin uptake inhibitors have been used in the treatment of mental depression, obsessive-compulsive disorder and bulimia. Fuller, R. W., "Serotonin uptake inhibitors: Uses in clinical therapy and in laboratory research," *Progress in Drug Research* 45: 167–204, Birkhäuser-Varlag, Basel (1995). As a result, transplants of serotonergic neurons or neuroprogenitor cells which have been previously exposed to an effective amount of FGF-4, FGF-8 and Shh so as to develop into serotonergic neurons may be advantageously employed to treat the above enumerated disorders and conditions.

Dopaminergic (DA) neurons, which reside in the ventral and ventro-lateral aspects of the midbrain, control postural reflexes, movement and reward-associated behaviors. DA neurons develop in the vicinity of the floor plate and are induced by contact-mediation. These neurons innervate multiple structures in the forebrain, and their degeneration or abnormal function is associated with Parkinson's disease, schizophrenia and drug addiction. lynes et al., *Cell* 80: 95–101 (1995).

DA neurons located in the substantia nigra have a great impact upon striatal activity as bilateral lesions of the nigrostriatal pathway produce a syndrome in experimental animals that is quite similar to the observed motor dysfunctions observed in Parkinson's disease: resting tremor, rigidity, akinesia and postural abnormalities. Bilateral lesions of the nigrostriatal pathway caused by 6-hydroxydopamine (OHDA) caused profound akinesia, adipsia, aphagia and sensory neglect in rodents, Ungerstedt, U. *Acta Physiol. Scand.* 1971 (Suppl. 367): 95–121; Yirek and Sladek, 1990, *Annu. Rev. Neurosci.* 13: 415–440.

As a result, transplants of dopaminergic neurons or neuroprogenitor cells which have been exposed to an effective amount of FGF-8 and Shh may be advantageously employed to treat the above enumerated disorders and conditions.

V. Modes for Carrying Out the Invention
A. Administration Methods:

The method of present invention may be advantageously carried out by direct transplant of dopaminergic or serotonergic neurons either before of after exposure to FGF-8 and Shh or FGF-4, FGF-8 and Shh, as the case may be, to the lesioned area. Method of neuronal transplant and cell culture are well known, e.g., U.S. Pat. No. 5,514,552; Yurek and Sladek, *Annu. Rev. Neurosci.* 13: 415–440 (1990) [see Rosenthal, A. *Neuron* 20: 169–172 (1998).

The factors may be delivered alone or in combination, and may be delivered along with a pharmaceutically acceptable vehicle. Ideally, such a vehicle would enhance the stability and/or delivery properties. The invention also provides for pharmaceutical compositions containing the active factor or fragment or derivative thereof, which can be administered using a suitable vehicle such as liposomes, microparticles or microcapsules. In various embodiments of the invention, it may be useful to use such compositions to achieve sustained release of the active component.

Furthermore, it may be desirable to administer a pharmaceutical composition of the invention containing a neuronal survival factor locally to the area in need of treatment, this may be achieved by, for example, local infusion during surgery, by injection, by means of a catheter, or by means of an implant, wherein such implant can be of a porous, non-porous, or gelatinous material, including membranes, such as silastic membranes or fibers.

Considerable attention has been placed on neural transplantation in patients afflicted with Parkinson's disease. These clinical experiments essentially evolved from basic scientific research using various animal models of parkinsonism as recipients of either fetal embryonic nerve cell or paraneuronal tissue grafts to brain-damaged areas. Animal experimentation with fetal DA nerve cell grafts have provided encouragement that such grafts could reverse DA deficits and restore motor function in animals with experimental lesions of the nigrostriatal DA system.

Murine mesencephalic cells taken from 14–16 day old embryos have been advantageously employed over those taken from later gestating donors in transplants as homografts or heterografts without immunosuppressive treatment. Yurek and Sladek, supra. Interestingly, this ages corresponds to the gestational age at which dopaminergic neurons undergo their final cell division. Lauder and Bloom, 1974, *J. Comp. Neurol.* 155: 469–82.

Solid grafts of embryonic mesencephalic tissue can also be dissociated into cell suspensions for transplantation. However, typical survival rates of such suspensions has been limited to about 10% of the grafted DA cells. Brudin et al., 1987, *Ann. N.Y. Acad. Sci.* 495: 473–96. However, embryonic mesencephalic tissue is not a pure source of DA cells—only about 0.1 1.0% of the total viable cells are surviving DA cells. As such, any graft of dissociated mesencephalic cells should contain a minimum of 100,000 to 150,000 viable cells in order to effectively compensate for DA loss.

Preferably, the transplant therapy of the present invention also incorporates some means of storing and preserving nerve cells for use in transplant surgery. Cryopreserved embryonic mesencephalic tissue has been successfully stored for up to 70 days and transplanted as either homografts in rodent [Collier et al., *Progress in Brain Research*, Vol. 78, New York, Elsevier (1988), pp. 631–36] and primate (Collier et al., 1987, *Brain Res.* 436: 363–66. It has also been demonstrated that embryonic mesencephalic cells can be successfully cultured after crysopreservation, Collier et al, supra. Alternatively, mesencephalic tissue can be stored short-term (2–5 days) in preservation medium at 4° C. and subsequently transplanted with surviving graft volumes similar to those for fresh tissue, Sauer et al., *Restor. Neurol Neurosci (Suppl.: $3^{rd}$ Int. Symp. Neural Tranplan.)*: 56 (1989).

Another approach to restoring function in trauma-associated or neurodegenerative disorders is to implant cells that are capable of releasing trophic factors in brain-damaged area. Fibroblast which were previously modified to synthesize and secret nerve growth factor (NGF), prevented further degeneration of cholinergic neurons in animals with surgical lesions of the fimbria-fornix, Rosenberg et al., *Science* 242: 1575–78 (1988). Retroviral transfected vectors that genetically code for the synthesis of trophic factors or neurotransmitters may also be used, Gage et al, 1987, *Neuroscience* 23: 795–807. Alternatively, embryonic cells may be cografted with other cells that may exert a trophic influence on the development of the immature cells. For example, both the growth and development of grated embryonic mesencephalic neurons are enhanced when co-cultured with embryonic striatal cells (Proshiantz et al., 1979, *Proc. Natl. Acad. Sci. USA* 76: 5387–91; DiPorzio et al., 1980, *Nature* 288: 370–73; Hemmendinger et al., 1981, *Proc. Natl. Acad. Sci. USA* 78; 1264–68; Hoffman et al., 1983, *Brain Res.* 274: 275–81), striatal membranes (Prochiantz et al., 1981, *Nature* 293: 570–72) or soluble striatal extracts (Tomozawa & Appel, 1986, *Brain Res.* 399: 111–124.

Both intraventricular and intraparenchymal grafts of fetal nigral neurons survive and proliferate in the host brain. The ventricular environment is rich is cerebral spinal fluid (CSF) nutrients and is advantageous for the survival of grafted tissue. The CSF also provides minimal resistance for the expansion and growth of grafted tissue. In addition, the anatomical location of the lateral ventricles provides an excellent base from which DA grafts can readily interact with areas directly adjacent to ventricles, such as the striatum and nucleus accumbens. Furthermore, the ventricular system may act as a conduit for substances secreted from grafts and thereby extend the influence of grafts to distal periventricular regions. Although the ventricular environment favors graft survival, the ependymal wall provides a barrier for fiber outgrowth and reinnervation of the dopaminergic lacking striatum. As a result, when intraventricular grafts lack a direct reinnervation of the striatum, the beneficial effects associated with the release of DA probably are limited to the passive diffusion of DA into the adjacent striatum. Moreover, ventricular grafts often elicit host immune rejection, Freed et al., 1988, Gash & Sladek, eds. 233–41, supra.; Yurek & Sladek, supra.

Graft placement, and the extent to which the graft reinnervates the striatum are both important factors for the functional recovery of the mesostriatal DA system. In the unilaterally DA-denervated animal, cortically placed DA grafts have been shown to reduce motor asymmetry, but have little effect on sensory neglect, Björklund et al., 1980, *Brain Res.* 199:307–33; Dunnett et al, 1981, *Brain Res.* 215: 147–61. In contrast, nigral grafts placed in proximity to lateral striatum in bilaterally DA-denervated animals effectively restore sensory damage. Dunnett et al., 1983, *Acta Physiol. Scan. Suppl.* 522: 39–47. Furthermore, the reversal of akinesia in bilaterally lesioned animals is observed only when the nucleus accumbens is reinnervated by the DA graft, Dunnet et al., supra, Nadaud et al., 1984, *Brain Res.* 304: 137–41.

While the transplantation site for DA graft has most often been in proximity to the ventricular region because of the favorable CSF environment in those regions to provide for graft survival, the degree of DA degeneration in Parkinson's disease is more pronounced in the putamen than in the caudate nucleus. Dopamine levels in the putamen are often 10–15% lower than in the caudate nucleus, Bemhiemer et al., *J. Neurol. Sci.* 20: 415–55; Nyberg et al. 1983, *Neurochem. Pathol.* 1: 193–202. Additionally, the caudal putamen is more severely depleted of DA-neurons than the rostral putamen (Kish et al., 1986, *Ann. Neurol.* 20: 26–31). Of the two striatal components (caudate nucleus and putamen), the putamen received the majority of motor input via a cortical-thalamic-putamen pathway (DeLong & Georgopoulos, 1983, *Handbook of Physiology, Section I: The Nervous System*, Vol. 2, ed. Brookhard, Mountcastle, Geiger, pp. 1017–61, Bethesda, Md.: Am. Physiol. Soc.), thus, the putamen may be a more favorable site for DA grafts targeting motor disorders associated with Parkinson's disease.

B. Pharmaceutical Compositions and Dosages

Therapeutic formulations of the compositions of the invention are prepared for storage as lyophilized formulations or aqueous solutions by mixing the neural survival agent having the desired degree of purity with optional "pharmaceutically-acceptable" or "physiologically-acceptable" carriers, excipients or stabilizers typically employed in the art (all of which are termed "excipients"). For example, buffering agents, stabilizing agents, preservatives, isotonifiers, non-ionic detergents, antioxidants and other miscellaneous additives. (See *Remington's Pharmaceutical Sciences*, 16th edition, A. Osol, Ed. (1980)). Such additives must be nontoxic to the recipients at the dosages and concentrations employed.

Buffering agents help to maintain the pH in the range which approximates physiological conditions. They are preferably present at concentration ranging from about 2 mM to about 50 mM. Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, there may be mentioned phosphate buffers, histidine buffers and trimethylamine salts such as Tris.

Preservatives are added to retard microbial growth, and are added in amounts ranging from 0.2%–1% (w/v). Suitable preservatives for use with the present invention include phenol, benzyl alcohol, meta-cresol, methyl paraben, propyl paraben, octadecyidimethylbenzyl ammonium chloride, benzalconium halides (e.g., chloride, bromide, iodide), hexamethonium chloride, alkyl parabens such as methyl or propyl paraben, catechol, resorcinol, cyclohexanol, and 3-pentanol.

Isotonicifiers sometimes known as "stabilizers" are present to ensure isotonicity of liquid compositions of the present invention and include polyhydric sugar alcohols, preferably trihydric or higher sugar alcohols, such as glycerin, erythritol, arabitol, xylitol, sorbitol and mannitol. Polyhydric alcohols can be present in an amount between 0.1% to 25% by weight, preferably 1% to 5% taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, monothioglycerol and sodium thio sulfate; low molecular weight polypeptides (i.e. <10 residues); proteins such as human serum albumin, bovine serum albumin, gelatin or immunoglobulins; hydrophilic polymers, such as polyvinylpyrrolidone monosaccharides, such as xylose, mannose, fructose, glucose; disaccharides such as lactose, maltose, sucrose and trisaccacharides such as raffinose; polysaccharides such as dextran. Stabilizers can be present in the range from 0.1 to 10,000 weights per part of weight active protein.

Non-ionic surfactants or detergents (also known as "wetting agents") are present to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic® polyols, polyoxyethylene sorbitan monoethers (Tween®-20, Tween®-80, etc.). Non-ionic surfactants are present in a range of about 0.05 mg/ml to about 1.0 mg/ml, preferably about 0.07 mg/ml to about 0.2 mg/ml.

Additional miscellaneous excipients include bulking agents, (e.g. starch), chelating agents (e.g. EDTA), antioxidants (e.g., ascorbic acid, methionine, vitamin E), and cosolvents.

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coascervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences*, 16th edition, A. Osal, Ed. (1980).

The formulations to be used for in vivo administration must be sterile. This is readily accomplished, for example, by filtration through sterile filtration membranes.

Sustained-release preparations may be prepared. Suitable examples of sustained-release preparations include semipermeable matrices of solid hydrophobic polymers containing the antibody mutant, which matrices are in the form of shaped articles, e.g., films, or microcapsules. Examples of sustained-release matrices include polyesters, hydrogels (for example, poly(2-hydroxyethyl-methacrylate), or poly (vinylalcohol)), polylactides (U.S. Pat. No. 3,773,919), copolymers of L-glutamic acid and ethyl-L-glutamate, nondegradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfliydryl residues, lyophilizing from acidic solutions, controlling moisture content, using appropriate additives, and developing specific polymer matrix compositions.

The amount of therapeutic polypeptide, antibody or fragment thereof which will be effective in the treatment of a particular disorder or condition will depend on the nature of the disorder or condition, and can be determined by standard clinical techniques. Where possible, it is desirable to determine the dose-response curve and the pharmaceutical compositions of the invention first in vitro, and then in useful animal model systems prior to testing in humans. However, based on common knowledge of the art, a pharmaceutical composition effective in promoting the survival of sensory neurons may provide a local therapeutic agent concentration of between about 5 and 20 ng/ml, and, preferably, between about 10 and 20 ng/ml. In an additional specific embodiment of the invention, a pharmaceutical composition effective in promoting the growth and survival of dopaminergic or serotonergic neurons or in causing the differentiation of neuroprogenitor cells into dopaminergic or serotonergic neurons may provide a local therapeutic agent concentration of between about 10 ng/ml and 100 mg/ml.

In a preferred embodiment, an aqueous solution of therapeutic polypeptide, antibody or fragment thereof is administered by subcutaneous injection. Each dose may range from about 0.5 $\mu$g to about 50 $\mu$g per kilogram of body weight, or more preferably, from about 3 $\mu$g to about 30 $\mu$g per kilogram body weight.

The dosing schedule for subcutaneous administration may vary from once a week to daily depending on a number of clinical factors, including the type of disease, severity of disease, and the subject's sensitivity to the therapeutic agent.

FGF-4, FGF-8 or Shh protein or variant may comprise an amino acid sequence or subsequence thereof as indicated in FIGS. 9–11, active amino acid sequence derived therefrom, or functionally equivalent sequence as this subsequence is believed to comprise the functional portion of the FGF-4, FGF-8 or Shh molecule. (E.g., the N-terminal amino acid residues 1–195 of Shh).

The amount of FGF-4, FGF-8 or Shh protein or variant effective for treating the neuroprogenitor cells which will be effective in the treatment of a particular disorder or condition will depend on the nature of the disorder or condition, and can be determined by standard clinical techniques. Where possible, it is desirable to determine the dose-response curve and the pharmaceutical compositions of the invention first in vitro, and then in useful animal model systems prior to testing in humans. However, based on common knowledge of the art, a pharmaceutical composition effective in promoting the survival of sensory neurons may provide a local FGF-8 or Shh protein concentration of between about 10 and 1000 ng/ml, preferably between 100 and 800 ng/ml and most preferably between about 200 ng/ml and 600 ng/ml of FGF-8 or Shh. In an additional specific embodiment of the invention, a pharmaceutical composition effective in promoting the growth and survival of retinal neurons may provide a local FGF-8 or Shh protein concentration of between about 10 ng/ml and 1000 ng/ml. Interestingly, FGF-4 appears to be highly concentration dependent and is effective in inducing differentiation in a range of about 5–20 ng/ml.

Effective doses of additional neurotrophic factors administered in combination with FGF-4, FGF-8 or Shh, such CNTF are in the same dose ranges as the effective dose of FGF-8 or Shh described previously. The active compound of the present method, FGF-4, FGF-8 or Shh, may optionally be formulated with a second agent, such as a neurotrophic factor. Exemplary neurotrophic factors include: nerve growth factor (NGF), ciliary neurotrophic factor (CNTF), bovine-derived neurotrophic factor (BDNF), neurotrophin-3 (NT-3), neurotrophin-4 (NT-4), aFGF, IL-1$\beta$, TNF$\beta$, Insulin-like growth factor (IGF-1, IGF-2), transforming growth factor beta (TGF-$\beta$, TGF-$\beta$1) or skeletal muscle extract, may be administered in any sterile biocompatible pharmaceutical carrier, including, but not limited to, saline, buffered saline, dextrose, and water.

If the subject manifests undesired side effects such as temperature elevation, cold or flu-like symptoms, fatigue, etc., it may be desirable to administer a lower dose at more frequent intervals. One or more additional drugs may be administered in combination with FGF-4, FGF-8 or Shh to alleviate such undesired side effects, for example, an antipyretic, anti-inflammatory or analgesic agent.

The following examples are offered by way of illustration and not by way of limitation. The disclosures of all citations in the specification are expressly incorporated herein by reference.

EXAMPLES

Introduction

In the following example, Applicants show that the regions of expression overlap between Sonic hedgehog (Shh), which is expressed along the ventral neural tube, and FGF8 which is locally produced at the mid/hindbrain boundary and in the rostral forebrain, define induction sites for dopaminergic (DA) neurons in the midbrain and forebrain. Applicants further show that the regions of expression overlap (intersection) of FGF8 and Shh in combination with FGF4, which is normally expressed in the primitive streak adjacent to the posterial neural plate, creates an inductive center for serotonergic (5HT) neurons in the rostral hindbrain. Finally, Applicants show that even though the FGF-8/Shh expression overlap region marks the location of specific classes of mature neurons at the mid-hindbrain boundary, it is not required for the activation of early regional genes in the region. As a result, it can be concluded that FGF-4, FGF-8 and Shh establish multiple, local organizing centers that control late, but not early patterning events in the neural tube. Similar grids of intersecting pathways could establish organizing centers in other organs.

Results

1) DA and 5HT Neurons are specified in Small Isolated Neural Plate Explants that Express both Shh and FGF8

Neural plates from 6 somite stage (E9) rat embryos was transected (together with the underlying axial mesoderm and head mesenchyme) along the A-P axis into seven, ~50–100 um long explants. Each explant was monitored in culture for up to 7 days for expression of markers that typify the rostral forebrain, caudal forebrain, mesencephalon, hindbrain and spinal cord, and for the appearance of DA and 5HT neurons. After 2–4 days in culture, explant #1 was found to express the telencephalic transcription factor B$f$1 [Shimamura and Rubenstein (1997) *Develop.* 124: 2709–271 8; Xuan et al. (1995) *Neuron* 14: 1141–1152] as well as the fore/midbrain transcription factors Otx1 and Otx2 (Sineone et al. (1992) *Nature* 358: 687–690). Explant #2 expressed Otx1 and Otx2, but not any of the other markers examined. Explants #3 and #4 expressed the mid/hindbrain regulatory genes Engrailed 1 (En1), Engrailed 2 (En2), Wnt1, Pax2, and Pax5, [Reviewed in Bally-Cuif and Wassef(1995) *Curr. Opin. Genet. Develop.* 5: 450–458; Joyner (1996) TIG 12: 15–20] and explants #3–6 expressed the floor plate marker FP4 (Placzek et al. (1993) *Develop.* 117: 205–218) which in the intact embryo extends from the mid-diencephalon to the caudal end of the spinal cord. Explants #1, #3 and #4 also expressed Fg$f$8, which in the unperturbed neural plate is detected in the mid/hindbrain boundary and the rostral forebrain [Crossley and Martin (1995) *Develop.* 121: 4349–4358; Crossley et al. (1996) *Nature* 380: 66–68; Heikinheimo et al. (1994) *Mech. Dev.* 48: 129–138; Shimamura and Rubenstein, (1997) *Develop.* 124: 2709–2718] (See FIG. 1). All dorsal and ventral explants expressed the general neuronal marker-tubulin (data not shown), and every ventral explant (v1–v6, FIG. 1G) expressed Shh, which is normally found in the ventral aspect throughout the neural tube (reviewed in Shimamura et al. (1995) *Development* 121: 3923–33).

When assayed 0–3 days after isolation, none of the above six explants contained DA or 5HT neurons (data not shown). However, after 5 days in culture, TH$^+$, dopamine producing, DA neurons were detectable in ventral explants v1 and v3, whereas 5HT$^+$ serotonergic neurons were detected in explants v4–v6 (FIG. 1G, bottom row and data not shown). Explants derived from 0 or 3 somite embryos that were cultured either with or without the head mesenchyme (paraxial mesoderm), gave rise to the same mature neurons as their counterparts from 6 somite embryos (data not shown).

The combined expression patterns of these genes suggested that early development of the neural tube was faithfully reproduced in the explants, and together with morphological landmarks allowed us to define explant #1 as the presumptive rostral forebrain, explant #2 as presumptive caudal forebrain, explant #3 as presumptive midbrain/caudal forebrain, explants #4, #5 as presumptive hindbrain, explant and #6 as presumptive caudal hindbrain/rostral spinal cord (FIG. 1). The spatially restricted appearance of DA and 5HT neurons in these explants indicated that by the 0 somite stage, all the signals that delineate the location of DA and 5HT neurons are present in small, isolated pieces of paraxial mesoderm-free neural plate tissue, permitting ventral DA neurons to specifically and independently develop in the midbrain and rostral forebrain explants, and 5HT neurons to develop in the hindbrain explants (FIG. 1).

Consistent with the notion that the characteristic positions of DA neurons is determined by epigenetic signals, we further found that the floor plate (a specialized group of ventral neural tube midline cells [Placzek et al. (1993), supra.] can induce DA neurons in ectopic dorsal locations in both of the midbrain and rostral forebrain regions (FIGS. 2A–C) [Hynes et al., (1995) Cell 80, 95–101], but not in the caudal forebrain explants (data not shown). On the other hand, the mid/hindbrain boundary (isthmus), a known organizing center for the midbrain and hindbrain [Bally-Cuif et al. (1992) Develop. 115: 999–1009; Gardner and Barald (1991) Develop. 113: 1037–1048; Marin and Puelles (1994) Dev. Biol. 163: 19–37; Martinez et al. (1995) Mec. Dev. 51: 289–303, which is located within explants #3 and #4 (FIG. 1), could induce DA neurons in ectopic caudal forebrain explants (FIG. 2F and data not shown). Thus, floor plate- and isthmus-derived signals appear to control the position of DA neurons along the D-V and A-P axes respectively.

The floor plate has previously been shown to mediate its inductive properties, in part, via Shh [reviewed in Tanabe and Jessell (1996) Science 274: 1115–1123; Chiang et al. (1996) Nature 382: 407–413; Ericson et al. (1996) Cell 87: 661–673], whereas the isthmus has been shown to mediate its inductive properties, in part, via FGF8 (Crossley et al. (1996) Nature 380: 66–68; Lee et al. (1997) Develop. 124: 959–969. Even though the floor plate terminates in the mid-diencephalon [Dale et al., (1997), supra; Placzek et al. (1993), supra] the expression domain of SHh extends along the ventral midline into the anterior forebrain (FIG. 1G) (reviewed in Shimamura et al. (1995) Develop. 121: 3923–33. Likewise, in addition to the isthmus region, FGF8 is highly expressed in the anterior neural ridge of the rostral forebrain [Crossley and Martin (1995), supra; Crossley et al. (1996), supra; Heikinheimo et al., (1994), supra; Shimamura and Rubenstein (1997), supra. (FIGS. 1D and G). These expression patterns lead to intersections of the FGF8 and Shh signals in the ventral aspect of the mid/hindbrain boundary and the ventral aspect of the rostral forebrain, the two sites where DA neurons appear to be born (FIG. 1G). Given this striking co-localization of Shh, FGF8 and DA neurons, it became important to explore the possibility that the intersection of Shh and FGF8 signals create inductive centers for ventral DA neurons in both the midbrain and rostral forebrain.

Figures 3E, 3F, 3G, 3H:
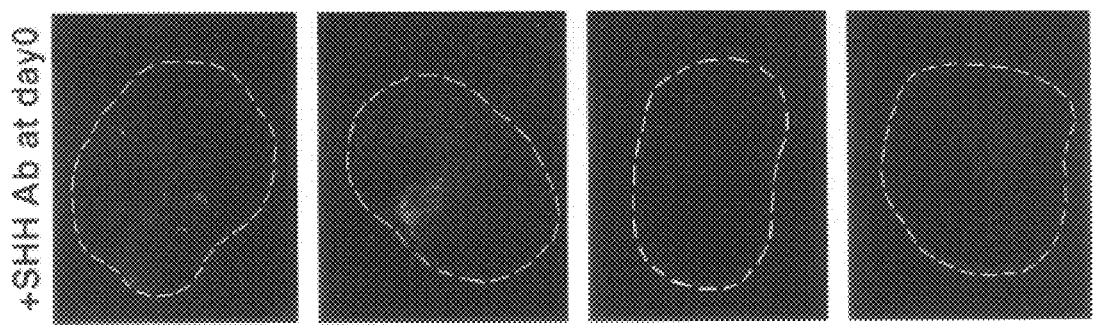
Figures 3I, 3J, 3K, 3L:
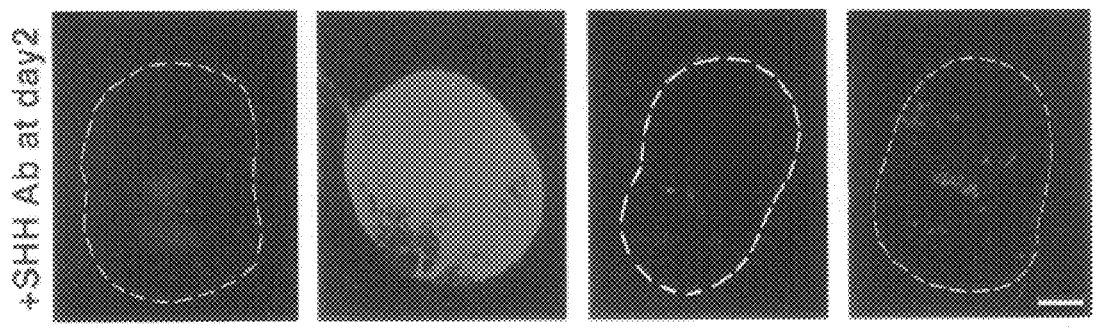

2) Shh is Necessary and Sufficient for the Induction of DA Neurons Along the D-V but not A-P Axis Shh function blocking antibody (Ericson et al. (1996) Cell 87: 661–673) and recombinant Shh protein (Hynes et al., (1995) Neuron 15: 35–44) were used to examine the role of Shh in DA neuron induction in the midbrain and rostral forebrain. E9 ventral midbrain (v3) or ventral rostral forebrain (v1) explants, containing endogenous Shh (FIG. 1G), were exposed to the Shh function blocking antibody from day 0 in culture, and monitored for the presence of DA neurons 6 days later. DA neurons were readily detected in control explants of both the midbrain and the forebrain (FIGS. 3A,B) [Hynes et al., Cell 80: 95–101 (1995); Hynes et al., Neuron 15: 35–44] but were dramatically reduced in both the v1 or v3 explants cultured in the presence of the Shh blocking antibody (FIGS. 3E,F). Shh antibody that was added to the explants after 24 or 48 h, prevented the appearance of DA in the forebrain but not in the midbrain, indicating that the critical period for Shh signaling is within the first 24 h of somitogenesis in the midbrain, and 48 h after somitogenesis begins in the forebrain (FIGS. 3I,J).

Shh is not only necessary, but appears to be sufficient for the induction of DA neurons in the midbrain and rostral forebrain, as indicated by the fact that recombinant Shh was capable of inducing ectopic DA neurons in the dorsal aspect of these two brain regions (Hynes et al., (1995) Neuron 15: 35–44 and data not shown). Shh, however, failed to induce DA neurons in ventral or dorsal caudal forebrain (v2,d2) or in hindbrain explants (v4–6, d4–6)(data not shown).

Taken together, these findings establish that Shh is physiologically required for the development of endogenous DA neurons in the ventral midbrain and ventral rostral forebrain and that Shh can control the position of DA neurons along the D-V but not A-P axis.

3) FGF8 Activity is Necessary for the Induction of DA Neurons in the Midbrain

In a manner similar to that used for Shh expression, ventral neural plate explants from the mid/hindbrain region (explants v3/4) of 0 somite rat embryos were cultured with soluble FGF receptor 3c (FGFR3-IgG), a high affinity blocking receptor for FGF8 (FGFR3 binds additional members of the FGF protein family) [MacArthur et al., (1995) Develop. 121: 3603–3613] or with soluble FGF receptor 1c (FGFR1-IgG) (a low affinity non-blocking receptor for FGF8 that binds multiple other members of the FGF protein family including FGF1, 2, 4, 5 and 6) [MacArthur et al., (1995), supra] or a soluble CD4 (CD4-IgG) (a T cell receptor used here as a negative control), and examined for the presence of DA neurons after 5 days in culture.

Figures 4A, 4B:
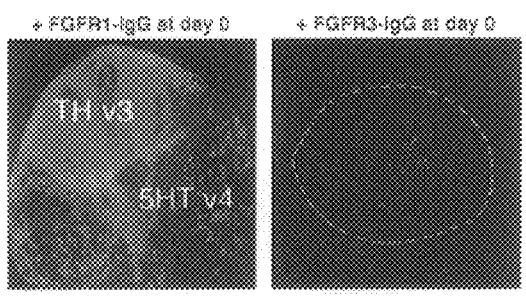

In the absence of soluble receptors, or in the presence of FGFR1-IgG or of CD4-IgG, TH$^+$, Ptx3$^+$ (a homeodomain gene that is specifically expressed in midbrain dopaminergic neurons) [Smidt et al., (1997) Proc. Natl. Acad. Sci. USA 94: 13305–13310] and Nurr1$^+$ (an orphan steroid receptor that is expressed in midbrain dopaminergic progenitors as well as in other cell types) [Law et al. (1992) Molec. Endocrin. 6: 2129–2135; Zetterstrom et al. (1997), Science 276: 248–250. DA neurons readily appeared in the mid/hindbrain explants (v3/4) (FIG. 4A and data not shown). In contrast, these neurons failed to develop in explants grown with FGFR3-IgG (FIG. 4B) and were not rescued by addition of a general mitogen (epidermal growth factor, data not shown), indicating that they require FGF8 activity. Similar results were obtained with paraxial mesoderm free explants (data not shown). Applicants further found that FGFR3-IgG blocked the development of DA neurons when added at 0, 3, and 6 somite stages, but not when added at the 24 somite stage (FIGS. 4B–D, FIG. 5 and data not shown). These findings are consistent with the idea that FGF8 is required early in the development of dopaminergic neurons and that FGF8 acts directly on this cell population shortly after it is first expressed at the 3 somite stage.

The development of other cell types in ventral midbrain explants v3, including lslet1$^+$ presumptive motoneurons [Ericson et al. (1992), Science 256: 1555–1560] Calretinin$^+$ neurons [Résibois and Rogers (1991) Neuroscience 46: 101–134; Rogers (1992) Brain Res. 587: 203–210] FP4$^+$ floor plate cells and HNF3β$^+$ ventral midline cells (Ruiz i Altaba et al., (1993) Mech. Dev. 44: 91–108; Sasaki and Hogan (1993) *Development* 118: 47–59, was not significantly affected by the presence of FGFR3-IgG (FIGS. 4E, G, H and data not shown), indicating that of the cell types examined within the midbrain, DA neurons, which are born adjacent to the mid/hindbrain boundary, are differentially sensitive to a reduction in the levels of FGF8 activity.

Since the development of DA neurons in the midbrain is preceded by expression of early regulatory genes in the midbrain and mid/hindbrain boundary, we examined whether any of these genes are also dependent on FGF8 activity. In the absence of soluble receptors or in the presence of FGFR1-IgG or of CD4-IgG, gene expression occurred normally (FIG. 5). In contrast, when mid/hindbrain neural plate explants were cultured for 4 days in the presence of FGFR3-IgG, mRNA for Fgf8 as well as mRNAs for genes that were shown to be required for the establishment of a mid/hindbrain boundary (Wnt1, Pax2, En1), or for development of the rostral hindbrain (Pax5,En2) [Reviewed in Bally-Cuif and Wassef (1995) *Curr. Opin. Genet. Develop.* 5: 450–458; Joyner (1996) TIG 12: 15–20] were eliminated or significantly reduced (FIG. 5A; lane 5). Surprisingly, when these genes were analyzed at earlier time points, we found that transcripts for Fgf8, Wnt1, En1, Pax2, and Pax5 were initially induced, persisted for the first 24 h, and only then declined (FIG. 5A; lane 3), indicating that FGF8 is required for their stable expression, but not for their induction. In contrast, the expression of En2 was not detected in the presence of FGFR3-IgG at any of the time points analyzed (FIG. 5), suggesting that FGF8 is required for its induction and that En2 may be a direct mediator in the FGF8 signal cascade. Several other genes expressed in the midbrain, ephrin A5, [Winslow et al., (1 995) *Neuron* 14: 973–981], Otx2 (Simeone et al., (1992) *Nature* 358: 687–690, protease nexin1 (PN1) (Küry et al., (1997), *Development* 124: 1251–1262) the helix-loop-helix factor Hes1 (Lobe, (1997) *Mech. Develop.* 62: 227–237), and the general cell markers G3PDH and—actin were not affected by blockade of the FGF8 signal (FIG. 5A), indicating that FGF8 is required for the induction or maintenance of only a subset of genes in the mid/hindbrain region.

Taken together, these findings support the idea that a requirement for isthmus-derived FGF8 between embryonic days 9–10 restricts the territory in which DA neurons originate along the A-P axis of the neural tube. Importantly, although FGF8 may mediate its function, in part, by inducing regulatory genes such as En2, the initial expression of several early control genes in the mid/hindbrain region is not dependent on FGF8. Thus, the information supplied by FGF8 may primarily target later patterning events, such as the specification of mature neurons. Signals other than FGF8 must provide positional information for early patterning and subdivision of this brain region.

4) FGF8 Activity is Necessary for the Induction of DA Neurons in the Rostral Forebrain We next determined whether the TH$^+$ (FIG. 1G), dopamine producing, dopamine-hydroxylase negative (data not shown) neurons in the rostral forebrain are also dependent on positional information from FGF8 activity for their development. Cephalic neural plate explants were exposed to the FGF8 blocking reagent and monitored for the appearance of DA neurons 5 days later. In control explants that were incubated with CD4-IgG or FGFR1-IgG, DA neurons developed normally (FIG. 6A). In contrast, no TH$^+$ neurons were present in cephalic explants that were grown in the presence of FGFR3-IgG (FIG. 6B). The forebrain contains multiple clusters of dopaminergic neurons (Specht et al. (1981) *J. Comp. Neurol.* 199: 255–276), and these findings indicate that they may all require FGF8 for their development. Likewise, even though multiple production sites of FGF8 exist in the forebrain, no TH$^+$ dopamine producing neurons appeared in these explants, following removal of the anterior neural ridge (ANR), the earliest expression site of FGF8 in the forebrain (FIG. 1D and data not shown). Thus, the ANR could be a physiological source of FGF8 activity and/or a major birth place for the developing DA neurons in the forebrain. FGF8 activity, which is initially detected in the ANR at the 4 somite stage (data not shown), is not only required for the development of mature neurons, but is also necessary for the expression of at least one early forebrain regulatory gene Bf1, a transcription factor which is first expressed in the 7 somite stage forebrain (data not shown), and is essential for normal development of the telencephalic and eye vesicles (Shimamura and Rubenstein, (1997) *Development* 124: 2709–271 8; Xuan et al. (1995) *Neuron* 14: 1141–1152. Thus, as before, we observed that expression of Bf1 was lost following surgical removal of the ANR (Shimamura and Rubenstein, (1997), supra (FIG. 6E), but was restored in the presence of FGF8 beads (Shimamura and Rubenstein, (1997), supra (FIG. 6F). Moreover, 3 somite stage cephalic explants that were cultured for 24 h with soluble FGFR1-IgG or with CD4-IgG (FIG. 6G and data not shown), readily gave rise to Bf1$^+$ cells, whereas similar explants that were exposed to FGFR3-IgG failed to express this gene (FIG. 6H). Consistent with the possibility that FGF8 upregulates Bf1 directly, we found that FGFR3-IgG prevented the expression of Bf1 when added to 0–3 somite stage explants, significantly reduced the number of Bf1$^+$ cells and the intensity of Bf1 expression when added at the 4–5 somite stage, but was ineffective at blocking Bf1 when added from 6 somites onward (data not shown).

Taken together these data suggest that FGF8 activity and Shh are universally required for the development of DA neurons in the anterior neural tube. Mechanistically, the findings further suggest that two distinct sets of genes are induced in response to the FGF8 activity. A set of genes that is responsible for the induction of dopaminergic neurons and is therefore common to the midbrain and forebrain, and a set of region specific genes (Bf1 in the forebrain and En2 in the midbrain), that is not associated with the dopaminergic phenotype.

5) FGF8 can Induce DA Neurons in Ectopic Anterior Neural Tube Locations Along the A-P but not the D-V Axis Given the fact that FGF8 is required for the development of DA neurons in the rostral forebrain and midbrain, we went on to examine whether it is sufficient to induce DA neurons in other locations along the A-P axis of the anterior neural tube. To this end, explants of rat caudal forebrain tissue (#2), which normally never give rise to DA neurons (FIG. 1G), were exposed to FGF8 beads, and monitored for the appearance of DA neurons after 6 days. Whereas DA neurons failed to be induced in explants that were exposed to control beads (FIG. 7A), TH$^+$, Nurr-1$^+$ and Ptx3$^+$ neurons were readily induced in the presence of FGF8 beads (FIGS. 7B&G). In addition, FGF8 was capable of inducing Fgf8 as previously reported (Crossley et al. (1996), *Nature* 380: 66–68) as well as En2, (Crossley et al., 1996, supra; Lee et al., (1997), supra.), En1, and Pax5 in ectopic caudal forebrain locations (FIG. 7G), even though it does not appear to be required for the initial activation of all these genes in the mid/hindbrain region (FIG. 5). FGF8 failed, however, to activate expression of Wnt1 or Pax2 in these explant cultures (FIG. 7G). Induction of DA neurons and En1/En2$^+$ protein was also observed in the presence of FGF4 and 6 coated beads, although neither of these factors are discretely expressed in the mid/hindbrain or telencephalic neural plate (data not shown). FGF1, 2, 5, 7 or 9, and multiple other neurotrophic factors and mitogens did not effectively induce DA neurons or any of the early midbrain markers in the caudal forebrain (data not shown).

To determine whether the ectopic induction of DA neurons by FGF8 is restricted along the dorso-ventral axis, ventral and dorsal caudal forebrain explants (explants v2 and d2) were cultured individually in the presence of FGF8 beads. FGF8 readily induced DA neurons in ventral but not dorsal caudal forebrain explants (FIGS. 7B and E). Furthermore, when v2 explants were incubated with FGF8 in combination with Shh blocking antibody, they failed to give rise to DA neurons (FIG. 7C).

Taken together, these findings support the hypothesis that FGF8 is sufficient to control the position of DA neurons along the A-P but not the D-V axis of the anterior neural tube and that it can induce DA neurons only in the presence of Shh. The fact that FGF8 was unable to induce a subset of essential mid/hindbrain regulatory genes (i.e. Pax2, Wnt1) in isolated caudal forebrain explants strengthens the idea that early patterning of the mid/hindbrain region is FGF8-independent and that FGF8 functions mainly as a source of positional information for late patterning events. The ability of FGF8 to induce a subset of mid/hindbrain regulatory genes (i.e. En1, En2, Pax5) may reflect its role in the maintenance of stable gene expression in this territory.

6) FGF8 and Shh can Cooperate to Induce DA Neurons in Ectopic Dorsal Diencephalic Locations In light of the findings that Shh and FGF8 can individually control the fate of DA neurons along the D-V and A-P axis respectively, we went on to examine whether these two factors can cooperate to specify ectopic DA neurons along both the D-V and A-P axes of the anterior neural tube. To this end, dorsal caudal forebrain explants (d2) were incubated in the presence of FGF8 and Shh and examined for the presence of DA neurons 6 days later. DA neurons were not detected in d2 explants that were cultured with Shh alone (FIG. 7D) or with FGF8 alone (FIG. 7E). In contrast, when Shh and FGF8 were added together, a large number of TH$^+$ DA neurons were readily detected (FIG. 7F). Thus, concurrent activation of two distinct signaling pathways, those of Shh and FGF8, appears to be required and sufficient for the induction of DA neurons in the anterior neural tube.

Figures 4C, 4D:
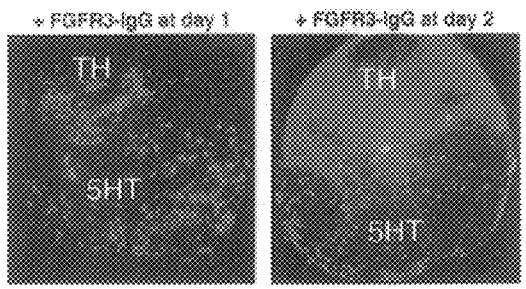
Figures 4E, 4F:
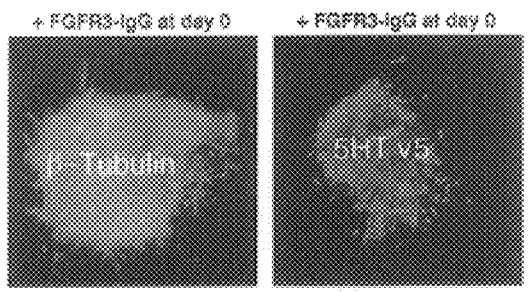
Figures 4G, 4H:
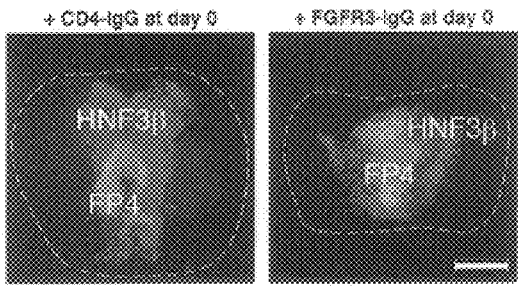

7) Intersection of the FGF8 and Shh Activity, in Conjunction with FGF4 Activity, Serves as an Induction Center for Serotonergic Neurons It is apparent that neural progenitors which give rise to rostral hindbrain serotonergic neurons should also have access to FGF8 from the isthmus and to Shh from the notochord and floor plate (FIG. 1G). To examine whether these progenitors utilize the intersecting Shh and FGF8 signals for their development, ventral hindbrain explants (v4) or mid/hindbrain explants (v3/4) were cultured in the presence of Shh blocking antibody, or the FGF8 activity blocking reagent respectively, and examined for 5HT neurons 6 days later. Irrelevant antibodies, or control IgG's (CD4-IgG and FGFR1-IgG), did not prevent normal development of 5HT neurons (FIGS. 3C and 4A). However, when similar explants were cultured with FGFR3-IgG (FIG. 4B), or with Shh function blocking antibodies (FIG. 3G), the development of 5HT neurons was effectively blocked, indicating that the intersection of FGF8 and Shh activity is used as positional information by more than a single cell type. Similar to the findings with DA neurons, FGFR3-IgG prevented the appearance of 5HT neurons when added at 0, 3, and 6 somite explants, but not when added at the 24 somite stage, indicating that FGF8 activity is required early in their development (FIGS. 4B–D). In contrast, Shh activity was found to be required 24 h later, ~48–72 h after the onset of somatogenesis (FIGS. 3G and K). Interestingly, unlike rostral hindbrain 5HT neurons (explants v3/4 or v4), the development of 5HT neurons in the caudal hindbrain (explants v5 or v6) was not inhibited by FGFR3-IgG (FIG. 4F). Thus, more caudally located 5HT neurons, which reside at a distance from the mid/hindbrain boundary, and hence the source of FGF8, do not appear to require FGF8 activity for their development. These neurons, however, failed to appear in the presence of Shh function blocking antibodies (FIGS. 3D, H, L), indicating that they are dependent on Shh for their development.

We next examined whether Shh and FGF8 are sufficient to induce 5HT neurons in ectopic locations. Ventral caudal forebrain (v2) and midbrain (v3) explants, which do not normally give rise to 5HT neurons, were cultured with FGF8 and Shh and examined for the presence of 5HT$^+$ serotonergic neurons 6 days later. Under these conditions, endogenous DA neurons developed normally in the midbrain (v3) explant and were readily induced by Shh and FGF8 in caudal forebrain (v2) explants. In contrast, 5HT neurons failed to appear in either midbrain or caudal forebrain explants (data not shown). Thus, although the development of rostral serotonergic neurons is restricted to the rostro/ventral aspect of the hindbrain because they depend on FGF8 and Shh, these two signals are not sufficient for their induction in ectopic locations.

In search for additional signal(s), which could act in conjunction with Shh/FGF8 to induce 5HT neurons, we found that FGF4 and FGF2 (but not FGF1, 5, 6, 8 or 9) can ectopically induce 5HT neurons in ventral midbrain explants (v3) (FIG. 8 and data not shown), which have endogenous sources of Shh and FGF8 (FIG. 1G), but not in dorsal midbrain explants (d3) or ventral caudal forebrain explants (v2) (data not shown). Surprisingly, the induction of 5HT neurons in the midbrain took place at the expense of DA neurons (FIGS. 8A,B), suggesting that in the presence of FGF4 activity, neural progenitors in the rostral midbrain may change their fate and become serotonergic, rather than dopaminergic neurons. The induction of 5HT neurons in the ventral midbrain occurred only when FGF4 was added before the 10 somite stage (data not shown), indicating that FGF4 must act before Shh and FGF8. Also, FGF4 was effective only within a narrow concentration range (5–20 ng/ml). At higher concentrations the development of both DA and 5HT neurons was inhibited (FIG. 8C). raising the possibility that FGF4 mimics a morphogenic gradient. Shh, FGF8 and FGF4 together, did not induce 5HT neurons in the caudal forebrain (data not shown). Thus, additional signals may be required to specify 5HT neurons in locations anterior to the midbrain or, it may be that the forebrain was pre-patterned by a local anterior organizer (Thomas and Beddington, 1996; Houart et al, 1998), and thus could no longer give rise to 5HT neurons.

Given previous reports that FGF2 may pattern the neural tube indirectly by changing the properties of paraxial mesoderm (Muhr et al., 1997), we examined whether the induction of 5HT neurons in midbrain explants is contingent on the presence of paraxial mesoderm. Following exposure to FGF2 or 4, midbrain explants from which the head mesenchyme had been enzymatically removed, still gave rise to 5HT neurons at the expense of DA neurons (FIG. 8D).

Although neither FGF2 nor FGF4 are discretely expressed in the hindbrain neural plate or mesoderm (data not shown), FGF4 is expressed in the primitive streak (a region juxtaposed to the posterior neural plate) from the early streak stage to the end of somitogenesis (Niswander and Martin, 1992 and FIG. 8E). Cell fate studies in the mouse suggest that cells from the anterior primitive streak contribute to hindbrain and spinal cord neural plate (Lawson and Pedersen, 1992). Thus, it is possible that FGF4 acts to prepattern the hindbrain by diffusion from the primitive streak, or by influencing hindbrain cells as they migrate from the primitive streak to the hindbrain region.

Jointly, these findings are consistent with the idea that at least three signals are required to establish an inductive center for rostral serotonergic neurons, and that progenitors in the rostral hindbrain assume a serotonergic, instead of a dopaminergic neuron cell fate, in response to Shh and FGF8 activity, because they were pre-patterned by FGF4 (or an FGF4-like activity).

Discussion

By simultaneously studying early markers (e.g. Pax2, Pax5, Wnt1, En1, En2, FGF8) and mature neurons (e.g. dopaminergic and serotonergic), Applicants have demonstrated that cell pattern in the neural plate is a multi-step process in which long range inducers (e.g. FGF4) that initially divide the neural plate into crude anterior and posterior compartments are later replaced by multiple local organizing centers (e.g. intersection of the Shh and FGF8 signals), that specify the identity and stereotypic locations of individual neuronal cell types, within the major brain subdivisions.

The Role of FGF8

Given the nature of our blocking reagent, we can not formally exclude the possibility that the action of FGF proteins other than FGF8 in the mid/hindbrain and forebrain regions had been inhibited, and that FGF8 may be redundant, or even irrelevant, for midbrain and forebrain development at the concentrations found in vivo. However, this possibility is unlikely for two reasons. First, soluble FGFR1 which binds multiple FGFs including FGF1, 2, 4, 5, and 6 but not FGF8 (data not shown), did not have any effect on the development of the mid/hindbrain region, nor did it block the differentiation of DA or 5HT neurons. Second, consistent with an essential role for FGF8 in the mid- and hindbrain, and with our blocking experiments, the caudal midbrain and rostral hindbrain [Meyers et al. (1998) *Nature Genetics* 18: 136–141], as well as midbrain dopaminergic neurons and transcripts for the homeodomain gene Ptx3, which marks midbrain dopaminergic neurons [Smidt et aL (1997) *Proc. Natl. Acad. Sci. USA* 94: 13305–13310] are virtually absent in mice that express severely reduced levels of FGF8, while the ventral midline marker HNF3 is still present (data not shown). Mice with a moderate reduction in the levels of FGF8 (Meyers et al. (1998), supra) do generate a population of midbrain dopaminergic neurons, but their numbers are dramatically reduced compared to normal littermates (data not shown).

It is worth noting that, even if the soluble FGF receptor does block an FGF8-like (rather than FGF8) molecule in the mid/hindbrain boundary and forebrain, the fundamental principle, that the intersections of FGF8 activity and Shh serve as inductive centers for dopaminergic and serotonergic neurons and as local late organizers in the neural plate, is valid.

In this work, we suggest that FGF8 may have a role in cell fate determination since it is both necessary and sufficient for the induction of dopaminergic neurons. However, understanding of the precise mechanism of FGF8 action (and of other factors that control development in the nervous system (e.g. Shh and the BMP's)) will require additional experiments, possibly using dissociated cell cultures.

Previous studies have shown that exogenously added FGF8 induces an ectopic midbrain in the chick diencephalon [Crossley et al., *Nature* 380: 66–68 (1996)], and activates the expression of mid/hindbrain (Crossley et al., (1996), supra; Lee et al., (1997), supra) and telencephalic (Shimamura and Rubenstein (1997), supra, specific genes. We have now extended these studies and provided evidence that endogenous FGF8 is in fact an essential patterning molecule for the midbrain, hindbrain and rostral forebrain. In the mid/hindbrain, FGF8 appears to have at least three distinct functions. First, it is necessary for the induction of at least one early regulatory gene which patterns the mid/hindbrain region (i.e. En2). Second, it is required for the sustained expression of regulatory genes which establish the isthmus (i.e. Pax2, Wnt1, En1), and third, it is essential for the induction of mature classes of neurons (DA and 5HT). FGF8, produced by the ANR, appears to perform similar functions in the rostral forebrain, as it is responsible for the activation of at least one early patterning gene Bƒ1, and for the induction of DA neurons. In addition, although we cannot exclude the possibility that the blocking of FGF8 was incomplete, our findings that only midbrain DA and rostral 5HT neurons, which are born adjacent to the isthmus, but not caudal hindbrain 5HT or Islet1$^+$ neurons, which are born away from the isthmus, required FGF8 for their development, suggests that FGF8 specifies particular classes of neurons, and that it acts as a local, rather than a long range patterning molecule. Finally, since FGF8 is able to induce DA neurons and midbrain markers in head-mesenchyme-free caudal forebrain neural plate, it's effect is not mediated by the paraxial mesoderm.

Importantly, our blocking experiments indicate that FGF8 activity is dispensable for local induction of Pax2, Wnt1 and En1 in the mid/hindbrain and, judged by that, is not essential for early patterning of the mid/hindbrain region along the A-P axis. Instead, FGF8 activity appears to be specifically targeted towards late patterning events including the stable expression of mid/hindbrain regulatory genes and the specification of mature neurons. The temporal expression pattern of Fgƒ8, which is first detected in the isthmus at the 3 somite stage, and is preceded by Pax2, Wnt1 and En1 (e.g. (Lee et al. (1997), supra; Row itch and McMahon, *Mech. Develop.* 52(1): 3–8, 1995 (1995) is consistent with a function for FGF-8 as a late patterning molecule. Such multi-level control of particular gene expression which was revealed in the mid/hindbrain, has been seen previously seen in Drosophila. For example, the segment polarity gene engrailed is initially activated by the pair-rule genes, but then requires the wingless gene product for its continued expression (e.g. Heemskerk et al. (1991) *Nature* 352: 404–410). It was shown previously that FGF8 can induce ectopic Wnt1 expression in the chick embryo (Crossley et al. (1996) *Nature* 380: 66–68), however we failed to see induction of Wnt1 in ventral caudal forebrain explants (v2). This difference could be due to the fact that the explants used here do not contain the presumptive roof plate region. Wnt1 is normally expressed in both the isthmus and the roof plate, and it is possible that in the chick embryo, only roof plate-derived Wnt1 was induced.

The Role of FGF4 in Patterning the Hindbrain

Applicants have observed that FGF4 can induce 5HT neurons in the ventral midbrain (v3), and that it does so at the expense of endogenous DA neurons. The fact that FGF4 is effective only prior to the 10 somite stage, suggests that it changes the response of midbrain progenitors to the later acting FGF8 and Shh, leading these progenitors to assume a more posterior cell identity. Caudalization of the neural tube in response to FGF2 has been previously demonstrated in the chick (Muhr et al. (1997) Neuron 19: 487–502 and frog [Cox and Hemmati-Brivanlou (1995) Development 121: 4349–4358; Kengaku and Okamoto (1995) Development 121: 3121–3 13 0; Lamb and Flarland (1995) Development 121: 3627–3636. However, our findings differ from these studies in two important aspects. First, in the chick, FGF2 was shown to caudalize the neural tube indirectly by modifying the adjacent paraxial mesoderm, whereas we demonstrate a direct action of FGF2 and FGF4 on head-mesenchyme-free midbrain. Second, in frog, early regional markers were used to monitor changes in FGF2-mediated patterning along the A-P axis. These markers cover broad domains of the neural plate which give rise to multiple classes of neurons and therefore leave open the questions as to how distinct neuronal cell types assume their characteristic positions. In contrast, we have examined changes in the specification of mature neurons and were therefore able to demonstrate that patterning along the A-P axis of the neural tube is a stepwise process, that the FGF2/4 activity is one of multiple, participating signals and that later acting signals determine the fate of mature neurons.

Neither FGF2 nor FGF4 are expressed discretely in the rostral hindbrain region in the 0–10 somite stage embryo (data not shown), indicating that they may not act as local signals. FGF4, which is structurally related to eFGF, a candidate neural posteriorizing agent in the Xenopus (Pownall et al., (1996), Development 122: 3881–3892) however, is expressed in the primitive streak of the pre-somitic embryo (Niswander and Martin (1992), Development 14: 755–768 (FIG. 8E)]. The primitive streak abuts the developing neural epithelium, and it is possible that FGF4 diffusing from this tissue would pattern the neural tube. In addition, it has been documented that cells which populate regions of the hindbrain and spinal cord neural plate migrate from the anterior primitive streak (Lawson and Pedersen (1992), Ciba Found. Symp. 165: 3–26. These cells, which were exposed to FGF4 during their migration, could influence their neighbors to, or become 5HT neurons themselves, in response to FGF8 and Shh. Finally, FGF4 may simulate the action of a yet unidentified member of the FGF protein family, which is locally expressed posterior to the isthmus, or of locally expressed cell adhesion molecules which were shown to activate the FGF signal cascade (Walsh and Doherty (1997), Ann. Rev. Cell & Develop. Biol. 13: 425–456. The narrow range of FGF4 concentrations that were effective in inducing 5HT neurons are consistent with the idea that it acts as a morphogen, possibly by diffusion from the primitive streak.

Even in the presence of FGF8, Shh and FGF4, we were unable to induce 5HT neurons in the caudal forebrain. One possible reason is that the forebrain may have been pre-patterned by an early local anterior organizer that precedes the ANR (Thomas and Beddington (1996), Current Biology 6: 1487–96; Houart et al. (1998) Nature 391: 788–792 and can no longer give rise to 5HT neurons. Alternatively, additional isthmus-derived signals may be required.

Cell Pattern in the Neural Plate

The stereotypic location of distinct neuronal cell types, and the regional expression of early cell markers, had made it clear that a Cartesian map of positional information must exist in the neural tube. Our findings illustrate in molecular terms, that a functional Cartesian grid of positional information which is composed of secreted molecules, does exist in the neural tube, and demonstrate that it acts to specify the fate and location of mature neurons. Traditional models predicted a non-dynamic, global Cartesian grid, in which the concentration of two intersecting molecules would define the fate of all cells throughout the neural tube. We, instead, have provided evidence that multiple local grids or organizing centers which overlap in time and space must exist, since: i) distinct intersections of Shh and FGF8 establish local organizing centers in the mid/hindbrain and forebrain, ii) the intersection of Shh and FGF8 specifies only a subset of neuronal classes in these brain regions, iii) FGF8 activity is not necessary to set up the initial pattern of early gene expression in the mid/hindbrain region [See also Dale et al. (1997), supra; Houart et al. (1998), supra; Thomas and Beddington (1996), supra.].

In addition, the findings that rostral hindbrain progenitors are pre-patterned by FGF4 or an FGF4-like activity, and as a consequence, assume a serotonergic as opposed to dopaminergic cell fate in response to Shh and FGF8, strengthens and extends the hypothesis that cell pattern in the neural plate is multi-step process which is sequentially controlled by distinct molecules. Thus, global organizer-derived neutralizing (e.g. chordin, noggin, follistatin, cerebrus, Xnr3, dkk1), and caudalizing (e.g. FGF2, FGF4, eFGF), molecules would induce the neural plate and divide it into anterior and posterior compartments (reviewed in Harland and Gerhart (1997), Ann. Rev. Cell Dev. Biol. 13: 611–667; Lumsden and Krumlauf, (1996), Science 274: 1109–1114. Subsequently, multiple, local organizing centers would be established as intersections of different secreted signaling molecules (e.g. Shh and FGF8). Finally, these local organizers, would specify the identity and stereotypic locations of individual neuronal cell types within the initial compartments (FIG. 8F).

Methods

Collagen Explant Cultures 0 to 6 somite stage rat embryos (Hilltop Labs, Pennsylvania) (plug day=E0) were dissected at room temperature in L15/4% horse serum into several pieces along the anterior-posterior axis (FIGS. 1D, E, G), unless specified, each explant was further divided into dorsal (d) and ventral (v) parts, and individual explants were embedded in type I collagen gel (Collaborative Biochemical Inc.), cultured in Opti-MEM with Glutamax (Gibco-BRL), 1% Penicillin/streptomycin,40 mM glucose, 0.5% Fetal Bovine Serum and 1/1000 Bovine Pituitary Extract for 1–7 days and then monitored for the appearance of region specific genes and cell types. Experiments were done on explants in which the underlying axial mesoderm (notochordal plate, etc.) and head mesenchyme were retained as well as on explants from which these mesodermal tissues were removed. To separate mesoderm and neuroectoderm, embryos were treated with 1 mg/ml dispase (BM Inc.) for 5 minutes at room temperature and then incubated in 50% horse serum/L15 for 5 minutes before dissection.

Fertilized chicken eggs were purchased from California Golden Egg Farm, and incubated at 38° C. for 2 days. 10–12 somite chick embryos were removed from the eggs and dissected at room temperature in L15/4% horse serum. Ventral rhombic isthmus explants (corresponding to the isthmic FGF8 expression domain) [Crossley et al. (1996) Nature 380: 66–68] without underlying mesodermal tissues were dissected out and used in the tissue recombination experiments described in FIGS. 2E and F.

Filter Explant Culture

Brain explants containing regions from the ANR to rostral hindbrain (FIG. 6) or regions from midbrain to rostral hindbrain (FIG. 5B) were cultured for 24 hours as described (Shimamura and Rubenstein, (1997), *Development* 124: 2709–2718. Both medial (future ventral) and lateral (future dorsal) portions were included in these explants.

In situ Hybridization and Immunostaining

In situ hybridization and immunostaining of sections and explants were performed as described in Hynes et al. (1995), *Neuron* 15: 35–44. Antibody dilutions were: rabbit anti-TH or mouse anti-TH, 1:500 (Chemicon Inc); mouse anti-FP4, 1:200; rabbit anti 5HT (IncStar Inc), 1:1000; mouse anti-β-tubulin (Chemicon Inc.): 1:1000. rabbit anti calretinin (Chemicon Inc.): 1:2000; Mouse anti Islet-1 mAb 2D6 (DSHB): 1:500; rabbit anti PAX2 (Berkeley Antibody): 1:1500; rabbit anti HNF3β: 1:2000; mouse anti chicken L1 (DSHB): 1:2000. Mouse anti-Shh function blocking antibody 5E1 (DSHB) was used at 1:200 in the blocking experiments, but at 1:1000 in the staining experiment (FIG. 1G, middle row); for staining, anti-Shh was added in the explant culture medium for 12 hours at 37° C. before fixing. Two-color, whole mount in situ hybridization was carried out as described previously (Shimamura and Rubenstein (1997), supra.

Protein Coated Beads

Heparin acrylic beads (Sigma Inc.) were soaked in 0.5–1 mg/ml protein solution overnight at 4° C., and washed 3 times in cold PBS just before use. Control beads were soaked in PBS in the absence of protein. FGF 1, 2, 4, 5, 6, 7, EGF and PDGF were purchased from R&D systems. FGF4, FGF-8 and Shh can be prepared using techniques described herein as well as standard and known techniques such as those described in Sambrook et al., infra and/or Ausubel et al, infra. A preparation for FGF-8 is described in MacArthur, C. et al, *Development* 121: 3603–3613. A preparation for Shh is described in Hynes et al., *Neuron* 15: 35–44.

IgG Fusion Proteins cDNA sequences coding for the extracellular domains (including signal peptide sequences) of CD4, FGFR1, FGFR3 were fused in frame to the SH2–SH3-hinge region of rat IgG2a, and cloned into an SV40 based expression vector. Recombinant plasmids were transiently transfected into 293T cells and conditioned media was harvested after 72 hours. IgG fusion proteins were purified from the conditioned media using T-adsorbent gels (Pierce inc.) according to the manufacturer's instruction, and used at a concentration of 60 μg/ml in explant culture medium supplemented with 1 μg/ml heparin (Sigma Inc.). Binding specificity of the IgG fusion proteins was confirmed using a filter binding assay. CD4-IgG (used as a control antibody) showed no binding to any FGF protein tested (data not shown).

RT-PCR

Total RNA was isolated from cultured explants using RNAzol B (Tel Test Inc.), and cDNA was made using MMLV RT (Gibco BRL). PCR reaction was carried out with $^{33}$P-dATP. Cycle numbers and template quantity was determined to be in the linear range for each gene. For each condition, two independent experiments were carried out with 15 explants. Three independent PCR reactions were done for each experiment.

Dopamine Measurements

Explants were assayed for dopamine content using an alumina extraction procedure and Ion-Pair reverse phase HPLC, with electrochemical detection as described in Horger et al (1995), *J. Neurochem.* 65: 770–774.

Summary

During development, distinct classes of neurons are specified in precise locations along the dorso-ventral and anterior-posterior axes of the neural tube. Herein Applicants provide evidence that intersections of Sonic hedgehog (SHh), which is expressed along the ventral neural tube, and FGF8 which is locally produced at the mid/hindbrain boundary and in the rostral forebrain, define induction sites for dopaminergic (DA) neurons in the midbrain and forebrain. We further provide evidence that the intersection of these same molecules, but in conjunction with FGF4, which is normally expressed in the primitive streak adjacent to the posterior neural plate, creates an inductive center for serotonergic (5HT) neurons in the rostral hindbrain. Finally, we show that even though the FGF8/Shh intersection marks the location of specific classes of mature neurons at the mid-hindbrain boundary, it is not required for the activation of early regional genes in this territory. These findings support the idea that FGF8, Shh and FGF4 establish multiple, local organizing centers that control late, but not early patterning events in the neural tube. Similar grids of intersecting signaling pathways could establish organizing centers in other organs.

What is claimed is:

1. A method of forming dopaminergic neurons by contacting in vitro neuroprogenitor cells with an effective amount of FGF-8 and sonic hedgehog (Shh) polypeptide wherein said FGF-8 and Shh polypeptides are encoded by nucleic acid sequences encoding polypeptides comprising SEQ ID NO:4 and SEQ ID NO:6, respectively.

2. A composition comprising a pharmaceutically-acceptable carrier and an effective amount of the FGF-8 polypeptide of SEQ ID NO:4 and the Shh polypeptide of SEQ ID NO:6 to stimulate differentiation of neuroprogenitor cells into dopaminergic neurons.

3. The method of claim 1 wherein the FGF-8 and Shh polypeptides are in the form of a composition further comprising a pharmaceutically-acceptable carrier.

* * * * *

UNITED STATES PATENT AND TRADEMARK OFFICE
CERTIFICATE OF CORRECTION

PATENT NO. : 6,277,820 B1
DATED : August 21, 2001
INVENTOR(S) : Rosenthal et al.

It is certified that error appears in the above-identified patent and that said Letters Patent is hereby corrected as shown below:

Title page,
ABSTRACT,
Line 15, delete "serotoneurigic" and insert therefor -- serotonergic --.

Column 1,
Line 16, delete "KrumIauf" and insert therefor -- Krumlauf --.
Line 27, delete "epeatedly" and insert therefor -- repeatedly --.

Column 4,
Line 17, delete "scrotonergic" and insert therefor -- serotonergic --.
Line 34, delete "to due" and insert therefor -- due to --.

Column 5,
Line 8, delete "neuroprogen itor" and insert therefor -- neuroprogenitor --.
Line 64, delete "isan E9 ratdorsal" and insert therefor -- is an E9 rat dorsal --.
Line 65, delete "mes/metencephalicexplant" and insert therefor -- mes/metencephalic explant --.

Column 6,
Line 30, delete "crown" and insert therefor -- grown --.

Column 7,
Lines 33-34, delete "proencephal on" and insert therefor -- prosencephalon --.

Column 9,
Line 16, delete "mesodern" and insert therefor -- mesoderm --.

Column 10,
Line 16, delete "T$^m$" and insert -- Tm --.
Line 33, delete "fonnamide" and insert therefor -- formamide --.
Line 34, delete "polyvinylpurrolidone" and insert therefor -- polyvinylpyrrolidone --.

Column 11,
Line 55, delete "*Absir*" and insert therefor -- *Abst.* --.
Line 55, delete "dopainine" and insert therefor -- dopamine --.
Line 56, delete "or rats" and insert therefor -- of rats --.
Line 57, delete "*Neitrosci.*" and insert therefor -- *Neurosci.* --

UNITED STATES PATENT AND TRADEMARK OFFICE
CERTIFICATE OF CORRECTION

PATENT NO. : 6,277,820 B1
DATED : August 21, 2001
INVENTOR(S) : Rosenthal et al.

It is certified that error appears in the above-identified patent and that said Letters Patent is hereby corrected as shown below:

<u>Column 13,</u>
Line 14, delete "Sam brook" and insert therefor -- Sambrook --.
Line 30, delete "suppresser" and insert therefor -- supressor --.
Line 50, delete "indigenous" and insert therefor -- endogenous --.

<u>Column 14,</u>
Line 29, delete "ofthe" and insert therefor -- of the --.

<u>Column 17,</u>
Line 14, delete "centrifug,ation" and insert therefor -- centrifugation --.
Line 47, delete "red ucing" and insert therefor -- reducing --.

Signed and Sealed this

Sixth Day of August, 2002

*Attest:*

*Attesting Officer*

JAMES E. ROGAN
*Director of the United States Patent and Trademark Office*